United States Patent
Spits et al.

(10) Patent No.: US 10,730,931 B2
(45) Date of Patent: Aug. 4, 2020

(54) RSV-SPECIFIC BINDING MOLECULES AND MEANS FOR PRODUCING THEM

(71) Applicant: MedImmune Limited, Cambridge (GB)

(72) Inventors: Hergen Spits, Amsterdam (NL); Tim Beaumont, Ouderkerk aan de Amstel (NL); Mark Jeroen Kwakkenbos, Amsterdam (NL); Etsuko Yasuda, Amsterdam (NL)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 16/042,547

(22) Filed: Jul. 23, 2018

(65) Prior Publication Data

US 2018/0327484 A1 Nov. 15, 2018

Related U.S. Application Data

(60) Continuation of application No. 15/047,306, filed on Feb. 18, 2016, now Pat. No. 10,059,757, which is a continuation of application No. 14/026,182, filed on Sep. 13, 2013, now Pat. No. 9,321,831, which is a division of application No. 12/600,950, filed as application No. PCT/NL2008/050333 on May 30, 2008, now Pat. No. 8,562,996.

(30) Foreign Application Priority Data

Jun. 1, 2007 (EP) .................................... 07109472

(51) Int. Cl.
*C07K 16/10* (2006.01)
*A61K 39/395* (2006.01)
*A61K 39/00* (2006.01)

(52) U.S. Cl.
CPC .... *C07K 16/1027* (2013.01); *A61K 2039/505* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,517,304 A | 5/1985 | Stott et al. |
| 4,526,938 A | 7/1985 | Churchill et al. |
| 4,659,563 A | 4/1987 | Dobkin |
| 4,717,766 A | 1/1988 | Dobkin |
| 4,760,026 A | 7/1988 | Lennox et al. |
| 4,800,078 A | 1/1989 | Prince et al. |
| 4,853,326 A | 8/1989 | Quash et al. |
| 4,917,893 A | 4/1990 | Okada et al. |
| 5,071,758 A | 12/1991 | Stott et al. |
| 5,128,326 A | 7/1992 | Balazs et al. |
| 5,137,804 A | 8/1992 | Greene et al. |
| 5,149,650 A | 9/1992 | Wertz et al. |
| 5,183,657 A | 2/1993 | Buurman |
| 5,194,595 A | 3/1993 | Wathen |
| 5,219,996 A | 6/1993 | Bodmer et al. |
| 5,223,254 A | 6/1993 | Paradiso et al. |
| 5,223,409 A | 6/1993 | Ladner et al. |
| 5,240,694 A | 8/1993 | Gwaltney, Jr. |
| 5,271,927 A | 12/1993 | Parker et al. |
| 5,279,935 A | 1/1994 | Nycz |
| 5,288,630 A | 2/1994 | Wathen |
| 5,290,540 A | 3/1994 | Prince et al. |
| 5,332,567 A | 7/1994 | Goldenberg |
| 5,332,805 A | 7/1994 | Carey et al. |
| 5,340,926 A | 8/1994 | Lowe et al. |
| 5,354,554 A | 10/1994 | Rhind |
| 5,391,478 A | 2/1995 | Greene et al. |
| 5,403,484 A | 4/1995 | Ladner et al. |
| 5,411,749 A | 5/1995 | Mayo et al. |
| 5,412,077 A | 5/1995 | Siber et al. |
| 5,418,136 A | 5/1995 | Miller et al. |
| 5,422,097 A | 6/1995 | Gwaltney, Jr. |
| 5,424,189 A | 6/1995 | Oberst et al. |
| 5,468,606 A | 11/1995 | Bogart et al. |
| 5,470,736 A | 11/1995 | Verma et al. |
| 5,476,997 A | 12/1995 | Kaneshima et al. |
| 5,484,893 A | 1/1996 | Parker et al. |
| 5,496,703 A | 3/1996 | Babish et al. |
| 5,506,209 A | 4/1996 | Mukerji et al. |
| 5,518,725 A | 5/1996 | Daynes et al. |
| 5,530,102 A | 6/1996 | Gristina et al. |
| 5,534,411 A | 7/1996 | Weltzin |
| 5,538,733 A | 7/1996 | Emery et al. |
| 5,538,952 A | 7/1996 | Mukerji et al. |
| 5,571,698 A | 11/1996 | Ladner et al. |
| 5,585,089 A | 12/1996 | Queen et al. |

(Continued)

FOREIGN PATENT DOCUMENTS

| AU | 713113 B2 | 11/1999 |
|---|---|---|
| AU | 2002219944 B2 | 2/2008 |

(Continued)

OTHER PUBLICATIONS

U.S. Appl. No. 09/724,396, filed Nov. 28, 2000, Young et al.
U.S. Appl. No. 13/413,609, filed Mar. 6, 2012, Young et al.
Abbas et al., 1991. *Cellular and Molecular Immunology*—Chapter 3 Antibodies and Antigens, p. 4547. W.B Saunders Company.
Abman et al., 1988. Role of Respiratory Syncytial Virus in Early Hospitalizations for Respiratory Distress of Young Infants With Cystic Fibrosis. *J Pediatr.* 113 (5):826-30.
Adams et al., 1998. Increased affinity leads to improved selective tumor delivery of single-chain Fv antibodies. 58(3):485-90.
Adams et al., 1998. Prolonged in vivo tumour retention of a human diabody targeting the extracellular domain of human HER2/neu. *Br J Cancer.* 77(9):1405-12.

(Continued)

*Primary Examiner* — Stacy B Chen
(74) *Attorney, Agent, or Firm* — Mueting, Raasch & Gebhardt, P.A.

(57) ABSTRACT

The invention provides antibodies and functional equivalents thereof which are capable of specifically binding RSV, and means and methods for producing them.

34 Claims, 34 Drawing Sheets

Specification includes a Sequence Listing.

(56) References Cited

U.S. PATENT DOCUMENTS

| | | | |
|---|---|---|---|
| 5,624,821 A | 4/1997 | Winter |
| 5,648,260 A | 7/1997 | Winter |
| 5,667,988 A | 9/1997 | Barbas et al. |
| 5,679,377 A | 10/1997 | Bernstein et al. |
| 5,693,762 A | 12/1997 | Queen et al. |
| 5,762,905 A | 6/1998 | Burton et al. |
| 5,786,464 A | 7/1998 | Seed |
| 5,811,524 A | 9/1998 | Brams et al. |
| 5,824,307 A | 10/1998 | Johnson |
| 5,840,298 A | 11/1998 | Brams et al. |
| 5,855,913 A | 1/1999 | Hanes et al. |
| 5,866,125 A | 2/1999 | Brams et al. |
| 5,874,064 A | 2/1999 | Edwards et al. |
| 5,912,015 A | 6/1999 | Bernstein et al. |
| 5,916,597 A | 6/1999 | Lee et al. |
| 5,929,212 A | 7/1999 | Jolliffe et al. |
| 5,934,272 A | 8/1999 | Lloyd et al. |
| 5,939,068 A | 8/1999 | Brams et al. |
| 5,955,364 A | 9/1999 | Brams et al. |
| 5,958,765 A | 9/1999 | Brams et al. |
| 5,985,309 A | 11/1999 | Edwards et al. |
| 5,985,320 A | 11/1999 | Edwards et al. |
| 5,989,463 A | 11/1999 | Tracy et al. |
| 6,019,968 A | 2/2000 | Platz et al. |
| 6,096,551 A | 8/2000 | Barbas et al. |
| 6,114,148 A | 9/2000 | Seed et al. |
| 6,117,980 A | 9/2000 | Gonzalez et al. |
| 6,121,022 A | 9/2000 | Presta et al. |
| 6,194,551 B1 | 2/2001 | Idusogie et al. |
| 6,277,375 B1 | 8/2001 | Ward |
| 6,413,771 B1 | 7/2002 | Brams et al. |
| 6,519,948 B2 | 2/2003 | Zorn |
| 6,528,624 B1 | 3/2003 | Idusogie |
| 6,537,809 B2 | 3/2003 | Brams et al. |
| 6,538,124 B1 | 3/2003 | Idusogie |
| 6,565,849 B2 | 5/2003 | Koenig et al. |
| 6,565,888 B1 | 5/2003 | Tracy et al. |
| 6,572,856 B1 | 6/2003 | Taylor et al. |
| 6,656,467 B2 | 12/2003 | Young et al. |
| 6,685,942 B1 | 2/2004 | Burton et al. |
| 6,699,473 B2 | 3/2004 | Raisch et al. |
| 6,737,056 B1 | 5/2004 | Presta |
| 6,818,216 B2 | 11/2004 | Young et al. |
| 6,855,493 B2 | 2/2005 | Young et al. |
| 7,083,784 B2 | 8/2006 | Dall' Acqua |
| 7,090,973 B1 | 8/2006 | Breton |
| 7,132,100 B2 | 11/2006 | Oliver et al. |
| 7,141,653 B2 | 11/2006 | Greenfeder |
| 7,179,900 B2 | 2/2007 | Young et al. |
| 7,208,162 B2 | 4/2007 | Prince et al. |
| 7,229,619 B1 | 6/2007 | Young et al. |
| 7,294,336 B2 | 11/2007 | Oliver et al. |
| 7,323,172 B2 | 1/2008 | Young et al. |
| 7,416,726 B2 | 8/2008 | Ravetch |
| 7,423,128 B2 | 9/2008 | Gazit-Bornstein et al. |
| 7,425,618 B2 | 9/2008 | Oliver et al. |
| 7,488,477 B2 | 2/2009 | Pilkington et al. |
| 7,553,489 B2 | 6/2009 | Young et al. |
| 7,635,568 B2 | 12/2009 | Young et al. |
| 7,658,921 B2 | 2/2010 | Dall' Acqua et al. |
| 7,670,600 B2 | 3/2010 | Dall' Acqua et al. |
| 7,696,334 B1 | 4/2010 | Bentwich |
| 7,700,720 B2 | 4/2010 | Tous et al. |
| 7,700,735 B2 | 4/2010 | Young et al. |
| 7,704,497 B2 | 4/2010 | Dall' Acqua et al. |
| 7,740,851 B2 | 6/2010 | Young et al. |
| 7,785,592 B2 | 8/2010 | Oliver et al. |
| 7,847,082 B2 | 12/2010 | Young et al. |
| 8,007,793 B2 | 8/2011 | Oliver et al. |
| 8,012,476 B2 | 9/2011 | Dall' Acqua et al. |
| 8,153,133 B2 | 4/2012 | Young et al. |
| 8,562,996 B2 | 10/2013 | Spits et al. |
| 2001/0034062 A1 | 10/2001 | Koenig et al. |
| 2002/0004046 A1 | 1/2002 | Johnson et al. |
| 2002/0018780 A1 | 2/2002 | Koenig et al. |
| 2002/0102257 A1 | 8/2002 | Johnson et al. |
| 2003/0194404 A1 | 10/2003 | Greenfeder et al. |
| 2003/0211100 A1 | 11/2003 | Bedian et al. |
| 2004/0002587 A1 | 1/2004 | Watkins |
| 2004/0005323 A1 | 1/2004 | Brams et al. |
| 2004/0038878 A1 | 2/2004 | Tanikawa et al. |
| 2004/0076631 A1 | 4/2004 | Brams et al. |
| 2004/0105862 A1 | 6/2004 | Pan et al. |
| 2005/0163777 A1 | 7/2005 | Rosen |
| 2005/0207977 A1 | 9/2005 | Reinl et al. |
| 2005/0208596 A1 | 9/2005 | Siegel |
| 2005/0288491 A1 | 12/2005 | Wilson et al. |
| 2006/0093599 A1 | 5/2006 | Gazit-Bornstein et al. |
| 2006/0115485 A1 | 6/2006 | Losonsky et al. |
| 2006/0140948 A1 | 6/2006 | Foltz et al. |
| 2006/0246071 A1 | 11/2006 | Green et al. |
| 2007/0122801 A1 | 5/2007 | Throsby et al. |
| 2008/0124345 A1 | 5/2008 | Rothe |
| 2009/0175883 A1 | 7/2009 | Oliver et al. |
| 2010/0098708 A1 | 4/2010 | Losonsky et al. |
| 2010/0266614 A1 | 10/2010 | Young et al. |
| 2011/0158985 A1 | 6/2011 | Losonsky et al. |
| 2011/0311454 A1 | 12/2011 | Dall' Acqua et al. |
| 2012/0039876 A1 | 2/2012 | Oliver et al. |
| 2012/0045456 A1 | 2/2012 | Oliver et al. |
| 2012/0070446 A1 | 3/2012 | Beaumont et al. |
| 2012/0070447 A1 | 3/2012 | Young et al. |
| 2012/0135006 A1 | 5/2012 | Young et al. |
| 2014/0072575 A1 | 3/2014 | Spits et al. |
| 2014/0093500 A1 | 4/2014 | Beaumont et al. |
| 2014/0377279 A9 | 12/2014 | Spits et al. |
| 2015/0366960 A1 | 12/2015 | Ulbrandt |
| 2016/0244509 A1 | 8/2016 | Spits et al. |
| 2016/0251412 A1 | 9/2016 | Beaumont et al. |
| 2016/0340414 A1 | 11/2016 | Ulbrandt et al. |

FOREIGN PATENT DOCUMENTS

| | | |
|---|---|---|
| CA | 2197684 A1 | 2/1996 |
| EP | 0327378 A1 | 8/1989 |
| EP | 0368684 A1 | 5/1990 |
| EP | 0413622 A1 | 2/1991 |
| EP | 0671927 A1 | 9/1995 |
| EP | 0682040 A1 | 11/1995 |
| EP | 0451216 B1 | 1/1996 |
| EP | 0699756 A1 | 3/1996 |
| EP | 1259547 A2 | 11/2002 |
| EP | 1265928 A1 | 12/2002 |
| EP | 1336410 A1 | 8/2003 |
| FR | 2758331 A1 | 7/1998 |
| JP | 01-268646 A | 10/1989 |
| JP | 2004-534513 A | 11/2004 |
| RU | 2160119 C2 | 12/2000 |
| WO | WO 90/07861 A1 | 7/1990 |
| WO | WO 91/05548 A1 | 5/1991 |
| WO | WO 92/05274 A1 | 4/1992 |
| WO | WO 92/19244 A2 | 11/1992 |
| WO | WO 93/05796 A1 | 4/1993 |
| WO | WO 93/15199 A1 | 8/1993 |
| WO | WO 93/15200 A1 | 8/1993 |
| WO | WO 93/19197 A1 | 9/1993 |
| WO | WO 93/20210 A1 | 10/1993 |
| WO | WO 94/06448 A1 | 3/1994 |
| WO | WO 94/27636 A1 | 12/1994 |
| WO | WO 94/29351 A2 | 12/1994 |
| WO | WO 95/04081 A1 | 2/1995 |
| WO | WO 96/05229 A1 | 2/1996 |
| WO | WO 96/20698 A2 | 7/1996 |
| WO | WO 96/40252 A1 | 12/1996 |
| WO | WO 97/32572 A2 | 9/1997 |
| WO | WO 97/34631 A1 | 9/1997 |
| WO | WO 97/44013 A1 | 11/1997 |
| WO | WO 98/23289 A1 | 6/1998 |
| WO | WO 98/31346 A1 | 7/1998 |
| WO | WO 98/31807 A1 | 7/1998 |
| WO | WO 98/33919 A2 | 8/1998 |
| WO | WO 98/34594 A1 | 8/1998 |
| WO | WO 99/15154 A1 | 4/1999 |
| WO | WO 99/20253 A1 | 4/1999 |

(56) References Cited

FOREIGN PATENT DOCUMENTS

| | | |
|---|---|---|
| WO | WO 99/28471 A2 | 6/1999 |
| WO | WO 99/51642 A1 | 10/1999 |
| WO | WO 99/66903 A2 | 12/1999 |
| WO | WO 00/29584 A1 | 5/2000 |
| WO | WO 00/42072 A2 | 7/2000 |
| WO | WO 00/56771 A1 | 9/2000 |
| WO | WO 00/69462 A1 | 11/2000 |
| WO | WO 00/73346 A1 | 12/2000 |
| WO | WO 01/55217 A1 | 8/2001 |
| WO | WO 01/58957 A2 | 8/2001 |
| WO | WO 01/64751 A2 | 9/2001 |
| WO | WO 01/77137 A1 | 10/2001 |
| WO | WO 02/43660 A2 | 6/2002 |
| WO | WO 02/060919 A2 | 8/2002 |
| WO | WO 03/052083 A2 | 6/2003 |
| WO | WO 03/054213 A2 | 7/2003 |
| WO | WO 2004/010935 A2 | 2/2004 |
| WO | WO 2004/016750 A2 | 2/2004 |
| WO | WO 2004/029207 A2 | 4/2004 |
| WO | WO 2004/035752 A2 | 4/2004 |
| WO | WO 2004/043989 A2 | 5/2004 |
| WO | WO 2004/083373 A2 | 9/2004 |
| WO | WO 2005/079479 A2 | 9/2005 |
| WO | WO 2006/034292 A2 | 3/2006 |
| WO | WO 2006/041970 A2 | 4/2006 |
| WO | WO 2006/116269 A2 | 11/2006 |
| WO | WO 2007/002543 A2 | 1/2007 |
| WO | WO 2007/067046 A1 | 6/2007 |
| WO | WO 2008/147196 A2 | 12/2008 |
| WO | WO 2009/003019 A1 | 12/2008 |
| WO | WO 2009/030237 A2 | 3/2009 |
| WO | WO 2009/114815 A1 | 9/2009 |
| WO | WO 2011/043643 A1 | 4/2011 |
| WO | WO 2014/121021 A1 | 8/2014 |
| WO | WO 2015/108967 A2 | 7/2015 |
| WO | WO 2015/108967 A3 | 9/2015 |

OTHER PUBLICATIONS

American Academy of Pediatrics Committee on Infectious Diseases: Use of Ribavirin in the Treatment of Respiratory Syncytial Virus Infection. *Pediatrics*. Sep. 1993;92(3):501-4.

*American Heritage Dictionary of the English Language*, Fourth Edition, Houghton Mifflin Company. 2000; p. 574 ("elderly"), p. 1223-4 ("old").

Ames et al., 1995. Conversion of murine Fabs isolated from a combinatorial phage display library to full length immunoglobulins. *J Immunol Methods*. 184(2):177-86.

Anderson et al., 1985. Microneutralization test for respiratory syncytial virus based on an enzyme immunoassay. *J Clin Microbiol*. 22:1050-1052.

Arbiza et al., 1992. Characterization of two antigenic sites recognized by neutralizing monoclonal antibodies directed against the fusion glycoprotein of human respiratory syncytial virus. *J Gen Virol*. 73: 2225-2234.

Balint and Larrick, 1993. Antibody engineering by parsimonious mutagenesis. *Gene*. 137(1):109-118.

Barbas III et al., 1992 "Human monoclonal Fab fragments derived from a combinatorial library bind to respiratory syncytial virus F glycoprotein and neutralize infectivity," *Proc Natl Acad Sci U S A*. 89(21):10164-8.

Barbas et al., 1996. Selection and evolution of high-affinity human antiviral antibodies. *Trends Biotech*. 14(7):230-234.

Bebbington et al., 1992, "High-level expression of a recombinant antibody from myeloma cells using a glutamine synthetase gene as an amplifiable selectable marker", *Biotechnology* (N Y), 10(2):169-75.

Beeler et al., 1989. Neutralization Epitopes of the F Glycoprotein of Respiratory Syncytial Virus: Effect of Mutation Upon Fusion Function. *J Virol*. 63(7):2941-50.

Bennett et al., 2007. Immunopathogenesis of Respiratory Syncytial Virus Bronchiolitis. *J Infect Dis*. 195(10):1532-1540.

Bentley and Rabbitts, 1980. Human immunoglobulin variable region genes—DNA Sequences of Two V Kappa Genes and a Pseudogene. *Nature* 288: 730-733.

Berzofsky and Berkower, 1993. In Paul, W.E., *Fundamental Immunology* (Raven Press), Chapter 8: Immunogenicity and antigen structure, p. 242.

Berzofsky and Berkower, 1993. In Paul, W.E., *Fundamental Immunology* (Raven Press), Chapter 9: Structure and Function of Immunoglobulins, p. 292-295.

Better et al., 1988. *Escherichia coli* secretion of an active chimeric antibody fragment. *Science*. 240(4855):1041-3.

Blake et al., 1999. Automated Kinetic Exclusion Assays to Quantify Protein Binding Interactions in Homogeneous Solution. *Analytical Biochemistry* 272: 123-134.

Boder et al., 2000. Directed evolution of antibody fragments with monovalent femtomolar antigen-binding affinity. *Proc Natl Acad Sci U S A*. 97(20):10701-5.

Boeckh et al., 2001. Phase 1 Evaluation of the Respiratory Syncytial Virus-Specific Monoclonal Antibody Palivizumab in Recipients of Hematopoietic Stem Cell Transplants. *J of Infect Dis*. 184: 350-354.

Boulianne et al., 1984. Production of functional chimaeric mouse/human antibody. *Nature* 312(5995):643-646.

Bourgeois et al., New peptides recognizing viral epitope with tropism to mucosa-useful for, e.g. diagnosing, preventing and treating viral infection(s). GENESEQ database entry for Accession No. AAW70933; Oct. 14, 1998 and alignment with Seq ID No. 12 of U.S. Appl. No. 09/771,415.

Brinkmann et al., 1995. Phage display of disulfide-stabilized Fv fragments. *J Immunol Methods*. 182(1):41-50.

Burton and Barbas, 1994. Human antibodies from combinatorial libraries. *Adv. Immunol*. 57:191-280.

Cao et al., 2003. Bispecific antibody conjugates in therapeutics. *Adv Drug Deliv Rev*. 55(2):171-97.

Carlsson et al., 1992. Human peripheral blood lymphocytes transplanted into SCID mice constitute an in vivo culture system exhibiting several parameters found in a normal humoral immune response and are a source of immunocytes for the production of human monoclonal antibodies. *J Immunol*. 148(4):1065-71.

Carson and Freimark, 1986. Human lymphocyte hybridomas and monoclonal antibodies. *Adv Immunol*. 38:275-311.

Casset et al., 2003. A peptide mimetic of an antiCD4 monoclonal antibody by rational design. *Biochem Biophys Res Commun*. 307(1): 198-205.

Chamat et al., 1999. Human monoclonal antibodies isolated from spontaneous Epstein Barr Virus—transformed tumors of Hu-SPL-SCID mice and specific for fusion protein display broad neutralizing activity toward respiratory syncytial virus. *J Infect Dis*. 180: 268-277.

Chanock et al., 1989. Respiratory syncytial virus. *Viral Infections of Humans, Epidemiology and Control*, 3rd Evans, ed., A.S. Chapter 20:525-544.

Chmura et al., 2001. Antibodies with infinite affinity. *Proc Nat Acad Sci*. 98(15):8480-8484.

Chothia et al., 1998. Structural determinants in the sequences of immunoglobulin variable domain. *J Mol Biol*. 278(2):457-79.

Chowdhury et al., 2005. Tailor-made antibody therapeutics. *Methods*. 36: 11-24.

Cleek et al., 1997. Biodegradable Polymeric Carriers for a bFGF Antibody for Cardiovascular Application. *Pro Int’l Symp Control Rel Bioact Mater*. 24: 853-854.

Colman, 1994. Effects of amino acid sequence changes on antibody-antigen interactions. *Res Immunol*. 145(1):33-6.

Connors, 1990. Chemical Kinetics: The Study of Reaction Rates in Solution. p. 152.

Conrad et al., 1987. Aerosolized ribavirin treatment of respiratory syncytial virus infection in infants hospitalized during an epidemic. *Pediatr Infect Dis J*. 6(2):152-158.

Crowe et al., 1994. Recombinant human respiratory syncytial virus (RSV) monoclonal antibody Fab is effective therapeutically when introduced directly into the lungs of RSV-infected mice. *Proc Natl Acad Sci USA*. 91:1386-1390.

(56) References Cited

OTHER PUBLICATIONS

Crowe et al., 1998. Monoclonal antibody-resistant mutants selected with a respiratory syncytial virus-neutralizing human antibody fab fragment (Fab 19) define a unique epitope on the fusion (F) glycoprotein. *Virology.* 252(2):373-5.
Cruse and Lewis, 1995. *Illustrated Dictionary of Immunology.* Boca Raton: CRC Press. pp. 18-19.
Dall'Acqua, 2002. Increasing the Affinity of a Human IgG1 for the Neonatal Fc Receptor: Biological Consequences. *J of Immunol.* 169: 5171-5180.
De Vincenzo et al., 2005. Factors Predicting Childhood Respiratory Syncytial Virus Severity—What They Indicate About Pathogenesis. *Ped Inf Dis J.* 24:S177-S183.
Delagrave et al., 1999. Effects of humanization by variable domain resurfacing on the antiviral activity of a single-chain antibody against respiratory syncytial virus. *Protein Eng.* 12(4):357-62.
DGene Database Accession No. A WJ00720, "Human antiRSV antibody light chain (VL) protein clone 744 SEQ ID:91". Dated May 14, 2009.
*Dorland's Illustrated Medical Dictionary,* 1994, 28th ed., Philadelphia: WB Saunders p. 874.
Downham et al., 1976. Breastfeeding protects against respiratory syncytial virus infections. *Br Med J.* 2(6030):274-6.
Duenas et al., 1996. In vitro immunization of naive human B cells yields high affinity immunoglobulin G antibodies as illustrated by phage display. *Immunology.* 89(1):1-7.
Duenas et al., 1996. Selection of phage displayed antibodies based on kinetic constants. *Mol Immunol.* 33(3):279-85.
Edelman et al., 1969. The Covalent Structure of an Entire gammaG Immunoglobulin Molecule. *PNAS* 63:78-85.
Egan et al., 1999. Effect of Sch 55700, a humanized monoclonal antibody to human Interleukin-5, on eosinophilic responses and bronchial hyperreactivity. *Arzneimittelforschung.* 49(9):779-790.
Ettinger et al., "Regulation of B cell differentiation and plasma cell generation by IL-21, a novel inducer of Blimp-1 and Bcl-6," Dec. 15, 2005 *J Immunol.* 175:7867-7879.
Evans, A.S., 1989. *Viral Infections of Humans, Epidemiology and Control.* 3rd ed., 525-44.
Everitt et al., 1996. The pharmacokinetics, antigenicity, and fusion-inhibition activity of RSHZ19, a humanized monoclonal antibody to respiratory syncytial virus, in healthy volunteers. *J Infect Dis.* 174:463-469.
Fahy and O'Byrne, 2001. Reactive Airways Disease. *Am J Respir Crit Care Med.* 163(4):8223.
Falsey, 1991. Noninfluenza Respiratory Virus Infection in Long-Term Care Facilities. *Infect Control Hosp Epidemiol.* 12(10):602-608.
Feigen et al., 1987. In: *Textbook of Pediatric Infectious Diseases,* WB Saunders, Philadelphia, at pp. 1653-1675; New Vaccine Development, Establishing Priorities, vol. 1, 1985, National Academy Press, Washington D.C. at pp. 397-409.
Fields et al., 1990. *Fields Virology,* 2nd Ed., vol. 1, Raven Press, NY p. 1045-1072.
Fields et al., 1996. Crystal Structure of the V-alpha domain of a T cell antigen receptor. *Immunotechnology* 2(4):270.
Fisher et al., 1999, Passive IgA monoclonal antibody is no. more effective than IgG at protecting mice from mucosal challenge with respiratory syncytial virus, *J. Infect Dis.*, 180(4):1324-7.
Foecking and Hofstetter, 1986. Powerful and versatile enhancer-promoter unit for mammalian expression vectors. *Gene.* 45:101-105.
Foote et al., 1991. Kinetic maturation of an immune response. *Nature* 352:530-532.
Foote et al., 1995. Kinetic and affinity limits on antibodies produced during immune response. *Proc Nat'l Acad Science USA.* 92:1254-1256.
Garcia-Barreno et al., 1989. Marked Differences in the Antigenic Structure of Human Respiratory Syncytial Virus F and G Glycoproteins. *J Virol.* 63(2):925-32.
Garvie and Gray, 1980. Outbreak of Respiratory Syncytial Virus Infection in the Elderly. *Br Med J.* 281(6250):1253-4.
Gilchrist, et al. 1994. National surveillance for respiratory syncytial virus, United States, 19851990. *J Infect Dis.* 170:986-990.
Gillies et al., 1989. High-level expression of chimeric antibodies using adapted cDNA variable region cassettes. *J Immunol Methods.* 125:191-202.
Glaser et al., 1992. Antibody engineering by codon-based mutagenesis in a filamentous phage vector system. *J Immunol.* 149: 3903-3913.
Glezen et al., 1981. Risk of Respiratory Syncytial Virus Infection for Infants From Low-Income Families in Relationship to Age, Sex, Ethnic Group, and Maternal Antibody Level. *J Pediatr.* 98(5):708-15.
Greenspan et al., 1999. Defining epitopes: It's not as easy as it seems. *Nature Biotechnology.* 17:936-937.
Groothuis et al., 1988. Respiratory Syncytial Virus Infection in Children with Bronchopulmonary Dysplasia. *Pediatrics.* 82(2):199-203.
Groothuis et al., 1993. Prophylactic Administration of Respiratory Syncytial Virus Immune Globulin to High-risk Infants and Young Children. The Respiratory Syncytial Virus Immune Globulin Study Group. *N Engl J Med.* 329(21):1524-1530.
Groves et al., 1987. Production of an ovine monoclonal antibody to testosterone by an interspecies fusion. *Hybridoma* 6(1):71-76.
Hacking and Hull, 2002. Respiratory syncytial virus—viral biology and the host response. *J Infect.* 45(1):18-24.
Hall et al., 1975. Nosocomial respiratory syncytial virus infections. *N. Engl. J. Med.* 293(26):1343-1346.
Hall et al., 1979. Neonatal Respiratory Syncytial Virus Infection. *N Engl J Med.* 300(8):393-6.
Hall et al., 1983. Aerosolized ribavirin treatment of infants with respiratory syncytial viral infection. A randomized double-blind study. *N Engl J Med.* 308(24):1443-1447.
Hall et al., 1985. Ribavirin treatment of respiratory syncytial viral infection in infants with underlying cardiopulmonary disease. *JAMA* 254(21):3047-3051.
Hall et al., eds., 1995. *Principles and Practice of Infectious Diseases.* 4th ed., Churchill Livingstone, New York, pp. 1501-1519.
Hall, 1987. Respiratory syncytial virus. *Textbook of Pediatric Infectious Diseases,* Feigin and Cherry, eds., WB Saunders, Philadelphia, 1653-1676.
Hall, C.B., 1993. Respiratory Syncytial Virus: What We Know Now. *Contemp Pediatrics.* 10: 92-110.
Hammerling et al., 1981. Production of Antibody-Producing Hybridomas in the Rodent Systems, in *Monoclonal antibodies and T-cell hybridomas,* Elsevier, NY. p. 563-587.
Haynes et al., 2002. Neutralizing anti-F glycoprotein and anti-substance p. antibody treatment effectively reduces infection and inflammation associated with respiratory syncytial virus infection. *J Virol.* 76(14):6873-6881.
Heard et al., 1999. Two Neutralizing Human Anti RSV Antibodies: Cloning, Expression and Characterization. *Molec. Med.* 5:35-45.
Hefta et al, 1998. Kinetic and affinity constants of epitope specific anti-carcinembryonic antigen (CEA) monoclonal antibodies for CEA and engineered CEA domain constructs. *Immunotechnology* 4:49-57.
Hellstrom et al., 1987. Antibodies for drug delivery. *Controlled Drug Delivery, Fundamentals and Applications* 2nd edition. Chapter 15: p. 623-653.
Hemming et al., 1985. Studies of Passive Immunotherapy for Infections of Respiratory Syncytial Virus in the Respiratory Tract of a Primate Model, *J Infect Dis.* 152(5):1083-7.
Hemming et al., 1986. Immunoglobulins in respiratory syncytial virus infections. *Clinical Use of Intravenous Immunoglobulins,* Morell and Nydegger., eds., Academic Press, London, pp. 285-294.
Hemming et al., 1988. Topically Administered Immunoglobulin Reduces Pulmonary Respiratory Syncytial Virus Shedding in Owl Monkeys. *Antimicrob Agents Chemother.* 32(8):1269-1270.
Henderson et al., 1979. Respiratory-Syncytial-Virus Infections, Reinfections and Immunity. A Prospective, Longitudinal Study in Young Children. *N Engl J Med.* 300(10):530-4.

(56) References Cited

OTHER PUBLICATIONS

Hertz et al., 1989. Respiratory Syncytial Virus-Induced Acute Lung Injury in Adult Patients With Bone Marrow Transplants: A Clinical Approach and Review of the Literature. *Medicine (Baltimore)*. 68(5):269-81.
Howard et al., 1989. Intracerebral Drug Delivery in Rats with Lesion-Induced Memory Deficits. *J Neurosurg*. 71(1):105-12.
Hudson and Souriau, 2003. Engineered Antibodies. *Nature Medicine* 9(1):129-34.
Ichiyoshi et al., 1995. A human anti-insulin IgG autoantibody apparently arises through clonal selection from an insulin-specific "germ-line" natural antibody template. Analysis by V gene segment reassortment and site-directed mutagenesis. *J Immunol*. 154(1):226-38.
Iverson and Borrebaeck, 1996. SCID-hu-PBL: a model for making human antibodies? *Semin Immunol*. 8(4):243-8.
Jackson et al., 1998. Antigen specificity and tumour targeting efficiency of a human carcinoembryonic antigen-specific scFv and affinity-matured derivatives. *Br. J. Cancer*. 78(2): 181-8.
Johnson et al., 1987. The G Glycoprotein of Human Respiratory Syncytial Viruses of Subgroups A and B: Extensive Sequence Divergence Between Antigenically Related Proteins. *Proc Natl Acad Sci USA*. 84(16):5625-9.
Johnson et al., 1991. Development of humanized monoclonal antibodies which neutralize respiratory syncytial virus. *J Cellular Biochem* Suppl. 15E. p. 120, Abstract No. 108.
Johnson et al., 1997 "Development of a Humanized Monoclonal Antibody (MEDI-493) With Potent In Vitro and In Vivo Activity Against Respiratory Syncytial Virus," *J Infect Dis*. 176(5):1215-24.
Johnson et al., 1999. A direct comparison of the activities of two humanized respiratory syncytial virus monoclonal antibodies: MEDI493 and RSHZ19. *J. Infect. Dis*. 180(1):35-40.
Kapikian et al., 1969. An Epidemiologic Study of Altered Clinical Reactivity to Respiratory Syncytial (RS) Virus Infection in Children Previously Vaccinated With an Inactivated RS Virus Vaccine. *Am J Epidemiol*. 89(4):405-21.
Karlsson et al., 1997. Experimental design for kinetic analysis of protein-protein Interactions with surface plasmon resonance biosensors. *J Immunol Meth*. 200:121-133.
Kettleborough et al., 1994. Isolation of tumor cell-specific Single-chain Fv from immunized mice using phage-antibody libraries and the re-construction of whole antibodies from these antibody fragments. *Eur J Immunol*. 24(4):952-8.
Kim et al., 1969. Respiratory Syncytial Virus Disease in Infants Despite Prior Administration of Antigenic Inactivated Vaccine. *Am J Epidemiol*. 89(4):422-34.
Kingston, R., 2003, "Chapter 9: Introduction of DNA into Mammalian Cells", in *Current Protocols in Molecular Biology*, John Wiley & Sons, pp. 9.0.1-9.0.5.
Kipriyanov and Little, 1999, "Generation of Recombinant Antibodies", *Mol Biotechnol.*, 12(2):173-201.
Knappik et al., 2000. Fully synthetic human combinatorial antibody libraries (HuCAL) based on modular consensus frameworks and CDRs randomized with trinucleotides. *J Mol Biol*. 296(I):57-86.
Krishnan et al., 2008. Therapeutic addition of motavizumab, a monoclonal antibody against respiratory syncytial virus (RSV), modulates epithelial cell responses to RSV infection. *Annual Interscience Conf Antimicrobial Agents Chemotherapy/Annual Meeting Infect Dis Soc Am*. 48/46 Oct. 28 Abstract V-4147.
Kudo et al., 1992. New strategies to establish human monoclonal antibodies. *Tohoku J Exp Med*. 168(2):323-327.
Kudo et al., 1993. Production of a human monoclonal antibody to a synthetic peptide by active in vivo immunization using a SCID mouse grafted with human lymphocytes. *Tohoku J Exp Med*. 171: 327-338.
Kunkel et al., 1987. Rapid and efficient site-specific mutagenesis without phenotypic selection. *Methods Enzymol*. 154:367-382.

Lagos et al., 2005. Administration of the antiRSV monoclonal antibody (Mab) Numax TM, is associated with a reduction in upper airway (UA) RSV load. *World Congress Pediatr Infect Disease*. Sep. 1-4.
Lam et al., 1997. Microencapsulation of Recombinant Humanized Monoclonal Antibody for Local Delivery. *Proc Int'l Symp Control Rel Bioact Mater*. 24:759-760.
Lamprecht et al., 1976. Role of Maternal Antibody in Pneumonia and Bronchiolitis Due to Respiratory Syncytial Virus. *J Infect Dis*. 134(3):211-7.
Landry et al., Evaluation of reconstituted lyophilized palivizumab given intravenously at 15 and 30 mg/kg. Pediatric Research, 45 (4 Pt 2: 166A, 969) *Annual Meeting of the American Pediatric Society and the Society for Pediatric Research*, San Francisco, California, USA. May 1-4, 1999 Poster Session (poster 87).
Langer and Peppas, 1983. Chemical and physical structure of polymers as carriers for controlled release of bioactive agents: a review. *J Macromol Sci.—Rev Macromol Chem Phys*. C23(1):611-26.
Langer, 1990. New methods of drug delivery. *Science*. 249:1527-1533.
Lee et al., 1998. Demonstration of IgM antibodies of high affinity within the anti-Galalphal-3Gal antibody repertoire. *Transplantation*. 66(8):1117-9.
Levy et al., 1985. Inhibition of Calcification of Bioprosthetic Heart Valves by Local Controlled-release Diphosphonate. *Science*. 228(4696):190-2.
Liu et al., 1987. Expression of mouse::human immunoglobulin heavy-chain cDNA in lymphoid cells. *Gene* 54(1):33-40.
Lobuglio et al., 1989. Mouse/human chimeric monoclonal antibody in man: kinetics and immune response. *Proc Natl Acad Sci USA*. 86(11):4220-4224.
Lonberg and Huszar, 1995. Human antibodies from transgenic mice. *Int. Rev. Immunol*. 13:65-93.
Love et al., 1993. How the anti-(metal chelate) antibody CHA255 is specific for the metal ion of its antigen: X-ray structures for two Fab'/hapten complexes with different metals in the chelate. *Biochemistry*. 32(41):10950-10959.
MacCallum et al., 1996. Antibody-antigen interactions: contact analysis and binding site topography. *J Mol Biol*. 262(5):732-45.
MacDonald et al., 1982. Respiratory Syncytial Viral Infection in Infants With Congenital Heart Disease. *N Engl J Med*. 307(7):397-400.
Malley et al., 1998. Reduction of Respiratory Syncytial Virus (RSV) in Tracheal Aspirates in Intubated Infants by Use of Humanized Monoclonal Antibody to RSV F Protein. *J of Infect Dis*. 178:1555-1561.
Marks et al., 1992. Bypassing immunization: building high affinity human antibodies by chain shuffling. *Biotechnology (NY)* 10(7):779-83.
Matsuoka et al., 2002, Characteristics of immunity induced by viral antigen or conferred by antibody via different administration routes, *Clin Exp Immunol*, 130(3):386-92.
Maynard et al., 2002. Protection against anthrax toxin by recombinant antibody fragments correlates with antigen affinity. *Nat Biotechnol*. 20(6):597-601.
McArthur-Vaughan et al., 2002. A rhesus monkey model of respiratory syncytial virus infection. *J. Med. Primatol*. 31(2):61-73.
McCall et al., 1999. Isolation and characterization of an anti-CD16 Single-chain Fv fragment and construction of an anti-HER2/neu/antiCD16 bispecific scFv that triggers CD16-dependent tumor cytolysis. *Mol Immunol*. 36(7):433-46.
Medimmune, Inc, 1999 Synagis (registered trademark) package insert, revised Dec. 2, 1999.
Medimmune, Inc. Annual Report (2001).
Medimmune, Inc's (MEDI) phase I Numax study shows potential to reduce RSV disease in upper airway of children. (Sep. 1, 2005) BioSpace Beat, Biospace.com (www.biospace.com/news.sub.--story.aspx?StoryID=21014020).
Medimmune, Inc's (MEDI) Release: Numax achieves primary endpoint in preliminary analysis of data from comparative phase 3

(56) References Cited

OTHER PUBLICATIONS trial with Synagis (Nov. 6, 2006) BioSpace Beat, Biospace.com (www.biospace.com/news.sub.--story.aspx?StoryID=36114&full=1).
Medimmune, SYNAGIS (registered trademark) package insert, last revised Oct. 23, 2002.
Meissner et al., 1999. Safety and pharmacokinetics of an intramuscular monoclonal antibody (SB 209763) against respiratory syncytial virus (RSV) in infants and young children at risk for severe RSV disease. *Antimicrob Agents Chemother*. 43(5):1183-8.
Mejias et al., 2005. Comparative Effects of Two Neutralizing Anti-Respiratory Syncytial Virus (RSV) Monoclonal Antibodies in the RSV Murine Model: Time versus Potency. *Antimicrobial Agents and Chemotherapy*. 49(11): 4700-4707.
Mejias et al., 2005. Respiratory syncytial virus infections: Old challenges and new opportunities. *Ped. Infect. Dis. J.* 24:S189-S197.
Morell et al., 1986. *Clinical Use of Intravenous Immunoglobulins*. Academic Press, London, pp. 285-294.
Morrison et al., 1984. Chimeric human antibody molecules: mouse antigen-binding Domains with human constant region domains. *Proc. Natl. Acad. Sci. USA* 81(21):6851-6855.
Morrison et al., 1985. Transfectomas provide novel chimeric antibodies. *Science* 229(4719):1202-1207.
Motavizumab vs palivizumab for RSV infections in infants, (Nov. 11, 2006) *Inpharma* vol. 1 No. 1563, p. 5.
Mullinax et al., 1992. Expression of a heterodimeric Fab antibody protein in one cloning step. *Bio Techniques*. 12:864-869.
Murphy et al., 1988. Passive Transfer of Respiratory Syncytial Virus (RSV) Antiserum Suppresses the Immune Response to the RSV Fusion (F) and Large (G) Glycoproteins Expressed by Recombinant Vaccinia Viruses. *J Virol*. 62(10):3907-10.
Murphy et al., 1991. Effect of Passive Antibody on the Immune Response of Cotton Rats to Purified F and G HG Glycoproteins of Respiratory Syncytial Virus (RSV). *Vaccine*. 9(3):185-9.
Murphy et al., 1994. An Update on Approaches to the Development of Respiratory Syncytial Virus (RSV) and Parainfluenza Virus Type 3 (PIV3) Vaccines. *Virus Res*. 32(1): 13-36.
Myszka et al., 1997. Kinetic analysis of a protein antigen-antibody interaction limited by mass transport on an optical biosensor. *Biophys Chem*. 64(13): 127-37.
Myszka et al., 1999. Survey of the 1998 optical biosensor literature. *J. Mol. Recog*. 12:390-408.
National Center for Biotechnology Information, National Library of Medicine, National Institutes of Health, GenBank Locus AF124196, Accession No. AF124196, "*Homo sapiens* clone JCOK1 kappa 1 immunoglobin light chain variable region mRNA, partial cds," [online]. Bethesda, MD [retrieved on Nov. 18, 2015]. Retrieved from the Internet: <URL:http://www.ncbi.nlm.nih.gov/nuccore/af124196>; 1 pg.
National Center for Biotechnology Information, National Library of Medicine, National Institutes of Health, GenBank Locus AF194796, Accession No. AF194796, "*Homo sapiens* clone 1536 immunoglubulin lambda light chain variable region mRNA, partial cds," [online]. Bethesda, MD [retrieved on Nov. 18, 2015]. Retrieved from the Internet: <URL:http://www.ncbi.nlm.nih.gov/nuccore/6643590>; 1 pg.
National Center for Biotechnology Information, National Library of Medicine, National Institutes of Health, GenBank Locus AY055486, Accession No. AY055486, "*Homo sapiens* isolate CLL261 immunoglubulin heavy chain variable region mRNA, partial cds," [online]. Bethesda, MD [retrieved on Nov. 18, 2015]. Retrieved from the Internet: <URL:http://www.ncbi.nlm.nih.gov/nuccore/ay055486>; 1 pg.
National Center for Biotechnology Information, National Library of Medicine, National Institutes of Health, Accession No. DA976849, "DA976849 SYNOV2 *Homo sapiens* cDNA clone SYNOV2007652 5-, mRNA sequence," [online]. Bethesda, MD [retrieved on Nov. 18, 2015]. Retrieved from the Internet: <URL:http://www.ncbi.nlm.nih.gov/nucest/da976849>; 1 pg.

National Center for Biotechnology Information, National Library of Medicine, National Institutes of Health, Accession No. DA986716, "DA986716 SYNOV2 *Homo sapiens* cDNA clone SYNOV2020051 5-, mRNA sequence," [online]. Bethesda, MD [retrieved on Nov. 18, 2015]. Retrieved from the Internet: <URL:http://www.ncbi.nlm.nih.gov/nucest/da986716>; 1 pg.
National Center for Biotechnology Information, National Library of Medicine, National Institutes of Health, GenBank Locus DQ490722, Accession No. DQ490722, "*Homo sapiens* clone SC4374 anti-West Nile virus immunoglobulin light chain variable region mRNA, partial cds," [online]. Bethesda, MD [retrieved on Nov. 18, 2015]. Retrieved from the Internet: <URL:http://www.ncbi.nlm.nih.gov/nuccore/94469906>; 1 pg.
Navas et al., 1992. Improved Outcome of Respiratory Syncytial Virus Infection in a High-Risk Hospitalized Population of Canadian children. Pediatric Investigators Collaborative Network on Infections in Canada. *J Pediatr*. 121(3):348-54.
Newman et al., 1992. 'Primatization' of recombinant antibodies for immunotherapy of human diseases: a Macaque/Human chimeric antibody against human CD4. *Biotechnol*. 10:1455-1460.
Nguyen et al., 2000. Efficient generation of respiratory syncytial virus (RSV)-neutralizing human MoAbs via human peripheral blood lymphocyte (hu-PBL)-SCID mice and scFv phage display libraries. *Clin. Exp. Immunol*. 122:85-93.
Ning et al., 1996. Intratumoral Radioimmunotherapy of a Human Colon Cancer Xenograft Using a Sustained Release Gel. *Radiotherapy and Oncology* 39: 179-89.
Norderhaug et al., 1997, "Versatile vectors for transient and stable expression of recombinant antibody molecules in mammalian cells", *J. Immunol. Methods*, 204:77-87.
O'Byrne and Postma, 1999. The Many Faces of Airway Inflammation. *Am J Respir Crit Care Med*. 159(5 Pt 2):S41-63.
Office Action for Japanese Patent Application No. 2016-172362, dated Jul. 4, 2017.
Ogra et al., 1988. Respiratory Syncytial Virus Infection and the Immunocompromised Host. *Pediatr Infect Dis J*. 7(4):246-9.
Ohno et al., 1985 "Antigen-binding specificities of antibodies are primarily determined by seven residues of VH", *Proc Natl Acad Sci USA*; 82:29452949.
Orkin and Motulsky, 1995 "Report and recommendations of the panel to assess the NIH investment in research on gene therapy," available from http://www.nih.gov/news/panelrep.html.
Ozaki et al., 2004 "Regulation of B cell differentiation and plasma cell generation by IL-21, a novel inducer of Blimp-1 and Bcl-6," *J Immunol*. 173(9):5361-71.
Padlan, 1991. A possible procedure for reducing the immunogenicity of antibody variable domains while preserving their ligand-binding properties. *Mol. Immunol*. 28(4/5):489-498.
Palomo et al., 1990. Induction of a Neutralizing Immune Response to Human Respiratory Syncytial Virus with Anti-Idiotypic Antibodies. *J. Virology* 64(9): 4199-4206.
Pakula and Sauer, "Genetic Analysis of Protein Stability and Function," *Annu Rev Genet*, 1989; 23:289-310.
Persic et al., 1997. An integrated vector system for the eukaryotic expression of antibodies or their fragments after selection from phage display libraries. *Gene*. 187(1):9-18.
*Physician's Desk Reference*, 2001, 55th ed. p. 1863-1864.
Plotnicky-Gilquin et al., 2002, Passive transfer of serum antibodies induced by BBG2Na, a subunit vaccine, in the elderly protects SCID mouse lungs against respiratory syncytial virus challenge, *Virology*, 10;303(1):130-7.
Pohl et al., 1992. Respiratory Syncytial Virus Infections in Pediatric Liver Transplant Recipients. *J Infect Dis*. 165(1): 166-9.
Press et al., 1970. The Amino Acid Sequences of the Fd Fragments of Two Human Gamma-1 Heavy chains. *Biochem J*. 117(4):641-60.
Prince et al., 1983. Mechanisms of Immunity to Respiratory Syncytial Virus in Cotton Rats. *Infect Immun*. 42(1):81-7.
Prince et al., 1985. Immunoprophylaxis and Immunotherapy of Respiratory Syncytial Virus Infection in the Cotton rat. *Virus Res*. 3(3):193-206.
Prince et al., 1985. Quantitative Aspects of Passive Immunity to Respiratory Syncytial Virus Infection in Infant Cotton Rats. *J Virol*. 55(3):517-20.

(56) References Cited

OTHER PUBLICATIONS

Prince et al., 1987. Effectiveness of Topically Administered Neutralizing Antibodies in Experimental Immunotherapy of Respiratory Syncytial Virus Infection in Cotton Rats. *J Virol.* 61(6): 1851-1854.
Prince et al., 1990. Mechanism of Antibody-mediated Viral Clearance in Immunotherapy of Respiratory Syncytial Virus Infection of Cotton Rats. *J Virol.* 64(6):309-12.
Prince et al., 1996. Treatment of parainfluenza virus type 3 bronchiolitis and pneumonia in a cotton rat model using topical antibody and glucocorticosteroid, *J. Infect. Dis.* 173:598-608.
Prince et al., 2000. Treatment of Respiratory Syncytial Virus Bronchiolitis and Pneumonia in a Cotton Rat Model with Systematically Administered Monoclonal Antibody (Palivizumab) and Glucocorticosteroid. *J Inf. Diseases* 182:1326-1330.
Prince, 1975. The Pathogenesis of Respiratory Syncytial Virus Infection in Infant Ferrets. Ph.D. Dissertation, University of California Los Angeles.
Prince, 2001. An update on respiratory syncytial virus antiviral agents. *Expert Opin Investig Drugs.* 10(2):297-308.
Raman et al., 1992. Diffusion-limited rates for monoclonal antibody binding to cytochrome. *Biochem.* 31:10370-10379.
Reljic et al., 2000 "Suppression of signal transducer and activator of transcription 3-dependent B lymphocyte terminal differentiation by BCL-6," *J Exp Med.* 192(12):1841-8.
Richter et al., 2008. Respiratory syncytial virus (RSV) therapy utilizing intranasally delivered motavizumab, a monoclonal antibody against F protein, *Annual Interscience Conf Antimicrobial Agents Chemotherapy/Annual Meed Infect Dis Soc Am.* 48/46 Oct. 28 Abstract V-4145.
Riechmann et al. 1988. Reshaping human antibodies for therapy. *Nature* 332:323-7.
Roguska et al., 1994. Humanization of murine monoclonal antibodies through variable domain resurfacing. *Proc. Natl. Acad. Sci. U.S.A.* 91(3):969-973.
Roost et al., 1995. Early high-affinity neutralizing anti-viral IgG responses without further overall improvements of affinity. *Proc. Natl. Acad. Sci. U.S.A.* 92:1257-1261.
Roskos et al., 2004, "The Clinical Pharmacology of Therapeutic Monoclonal Antibodies," *Drug Development Research* 61:108-120.
Rosok et al., 1995. A combinatorial library strategy for the rapid humanization of anticarcinoma BR 96 Fab. *J. Biol. Chem.* 271(27):22611-22618.
Rudikoff et al., 1982. Single amino acid substitution altering antigen-binding specificity. *Proc. Natl. Acad. Sci. USA* 79(6):1979-1983.
Russian Decision to Grant (translated) for RU patent application No. 2014 125 126, dated Apr. 13, 2017; 5 pages.
Ruther and Muller-Hill, 1983. Easy identification of cDNA clones. *EMBO J.* 2:1791-1794.
Ruuskanen et al., 1993. Respiratory syncytial virus. *Curr Probl Pediatr.* 23(2):50-79.
Saez-Llorens et al., 1998. Safety and pharmacokinetics of an intramuscular humanized monoclonal antibody to respiratory syncytial virus in premature infants and infants with bronchopulmonary dysplasia. *Pediatr. Infect Dis J* 17:787-91.
Saez-Llorens et al., 1997. Phase I/II open label multi dose escalation trial of a humanized respiratory syncytial virus (RSV) monoclonal antibody (Medi-493) administered intramuscularly (IM) in high risk children. *Abstracts in Non HIV virology, ICAAC* Toronto.
Sahagan et al., 1986. A genetically engineered murine/human chimeric antibody retains specificity for human tumor-associated antigen. *J. Immunol.* 137(3):1066-1074.
Sakurai et al., 1999. Human antibody responses to mature and immature forms of viral envelope in respiratory syncytial virus infection: significance for subunit vaccines. *J Virol.* 73(4):2956-2962.
Saudek et al., 1989. A Preliminary Trial of the Programmable Implantable Medication System for Insulin Delivery. *N Engl J Med.* 321(9):574-9.

Schier et al., 1996. Isolation of high-affinity monomeric human anti-c-erbB-2 single chain Fv using affinity-driven selection. *J. Mol. Biol.* 255(1):2843.
Schier et al., 1996. Isolation of picomolar affinity anti-c-erbB-2 Single-chain Fv by molecular evolution of the complementarity determining regions in the center of the antibody binding site. *J. Mol. Biol.* 263(4):551-567.
Scott et al., 1985. Cellular reactivity to respiratory syncytial virus in human colostrum and breast milk. *J Med Virol.* 17(1):83-93.
Seaver, 1994. Monoclonal antibodies in industry: More difficult than originally thought; *Genetic Engineering News*, vol. 14, No. 14, p. 10 and 21.
Sefton, 1987. Implantable Pumps. *CRC Crit. Rev. Biomed. Eng.* 14:201-240.
Sevier et al. 1981. Monoclonal antibodies in clinical immunology. *Clin Chem* 27:1797-806.
Shreder, 2000. Synthetic haptens as probes of antibody response and immunorecognition; *Methods*; 20(3):372-9.
Shvarts et al., 2002 "A senescence rescue screen identifies BCL6 as an inhibitor of anti-proliferative p19(ARF)-p53 signaling" *Genes Dev.* 16:681-686.
Sibille et al., 1997, "Mimotopes of polyreactive anti-DNA antibodies identified using phage-display peptide libraries", *Eur J Immunol*; 27:1221-1228.
Skaricic et al., 2008, "Genetic delivery of an anti-RSV antibody to protect against pulmonary infection with RSV," *Virology.* 378(1):79-85.
Smith et al., 1991. A Controlled Trial of Aerosolized Ribavirin in Infants Receiving Mechanical Ventilation for Severe Respiratory Syncytial Virus Infection, *N Engl J Med.* 325(I):24-9.
Song et al., 1995. Antibody Mediated Lung Targeting of Long-Circulating Emulsions, PDA *Journal of Pharmaceutical Science & Technology* 50: 372-77.
Sorbera et al., 1998. Palivizumab. *Drug Data Report* 20:702-703.
Sorbera et al., 1998. Palivizumab. *Drugs of the Future* 23:970-976.
Steplewski et al., 1988. Biological activity of human-mouse IgGI, IgG2, IgG3, and IgG4 chimeric monoclonal antibodies with anti-tumor specificity. *Proc. Natl. Acad. Sci. USA* 85(13):4852-4856.
Stott et al., 1984. The characterization and uses of monoclonal antibodies to respiratory syncytial virus. *Dev Biol Stand.* 57:237-44.
Studnicka et al., 1994. Human-engineered monoclonal antibodies retain full specific binding activity by preserving non-CDR complementarity-modulating residues. *Protein Eng.* 7:805-814.
Subramanian et al., 1997. Randomized double blind placebo controlled dose escalation trial of a humanized respiratory syncytial virus monoclonal antibody in high risk infants. Poster session infect. dis. 130A:768.
Subramanian et al., 1998. Safety, Tolerance and Pharmacokinetics of a Humanized Monoclonal Antibody to Respiratory Syncytial Virus in Premature Infants and Infants with Bronchopulmonary Dysplasia. *Pediatric Infect Dis J.* 17:110-115.
Sun et al. 1987. Chimeric antibody with human constant regions and mouse variable regions directed against carcinoma-associated antigen 17-1A. *Proc. Natl. Acad. Sci. USA* 84:214-218.
Takahashi et al. 1984. Rearranged immunoglobulin heavy chain variable region (VH) pseudogene that deletes the second complementarity-determining region. *Proc. Natl. Acad. Sci. USA.* 81:5194-198.
Takeda et al., 1985. Construction of chimaeric processed immunoglobulin genes containing mouse variable and human constant region sequences. *Nature* 314(6010):452-454.
Talwar et al., 1976. Isoimmunization against human chorionic gonadotropin with conjugates of processed beta-subunit of the hormone and tetanus toxoid, *Proc. Natl. Acad. Sci. USA.* 73(1):218-222.
Taylor et al., 1984. Monoclonal antibodies protect against respiratory syncytial virus infection in mice. *Immunology.* 52(1): 137-42.
Taylor et al., 1992. Protective epitopes on the fusion protein of respiratory syncytial virus recognized by murine and bovine monoclonal antibodies. *J Gen Virol.* 73 (Pt 9):2217-23.
The 65 years and older population: 2000; *Census 2000 Brief*, US Census Bureau.

(56) References Cited

OTHER PUBLICATIONS

The Impact-RSV Study Group, 1998. Palivizumab, a humanized respiratory syncytial virus monoclonal antibody, reduces hospitalization from respiratory syncytial virus infection in high-risk infants. *Pediatrics.* 102(3 Pt 1):531-537.
Thompson et al., 1996. Affinity maturation of a high-affinity human monoclonal antibody against the third hypervariable loop of human immunodeficiency virus: use of phage display to improve affinity and broaden strain reactivity. *J. Mol. Biol.* 256(1):77-88.
Traggiai et al., 2004 "An efficient method to make human monoclonal antibodies from memory B cells: potent neutralization of SARS coronavirus," *Nat. Med.* 10:871-875.
Trill et al., 1995, "Production of monoclonal antibodies in COS and CHO cells", *Curr Opin Biotechnol;* 6(5):553-60.
Tsui et al., "Progressive epitope-blocked panning of a phage library for isolation of human RSV antibodies," *Journal of Immunological Methods,* 2002, 263:123-132.
U.S. Census Bureau "Age Data" 2000 Census http://www.census.gov/population/www/socdemoiage.html (last accessed Apr. 17, 2006).
U.S. Census Bureau, Age Data, website updated May 12, 2004, http://www.census.gov/population/www/socdemo/age.html.
U.S. Department of Commerce, Economics and Statistics Administration, Bureau of the Census, "We the American Elderly," Sep. 1993.
Van Der Merwe et al., 1993 Affinity and kinetic analysis of the interaction of the cell adhesion molecules rat CD2 and CD48. *EMBO J.* 12(13):4945-4954.
Van Der Merwe et al., 1994. Human cell-adhesion molecule CD2 binds CD58 (LFA-3) with a very low affinity and an extremely fast dissociation rate but does not bind CD48 or CD59. *Biochemistry* 33(33):10149-10160.
Van Wyke Coelingh et al., 1985. Antigenic variation in the hemagglutinin neuraminidase protein of human parainfluenza type 3 virus, *Virology,* 143(2):569-582.
Vancott et al., 1994. Dissociation rate of antibody-gp 120 binding interactions is predictive of V3-mediated neutralization of HIV-I. *J. Immunol.* 153(1):449-59.
Verma et al., 1997. Gene therapy—promises, problems and prospects. *Nature.* 389:239-242.
Wald et al. 1988. In re ribavirin: a case of premature adjudication? *J. Pediatr.* 112:154-158.
Walsh et al., 1984. Protection from respiratory syncytial virus infection in cotton rats by passive transfer of monoclonal antibodies. *Infect Immun.* 43(2):756-8.
Walsh et al., 1987, Immunization with Glycoprotein Subunits of Respiratory Syncytial Virus to Protect Cotton Rats Against Viral Infection. *J Infect Dis.* 155(6):1198-204.
Ware et al., 1985. Human, rat or mouse hybridomas secrete high levels of monoclonal antibodies following transplantation into mice with severe combined immunodeficiency disease (SCID). *J Immunol Methods.* 85(2):353-61.
Warren, 1990 "Salvage Receptors: Two of a Kind?" *Cell* 62:1-2.
Watkins et al., 1997. Determination of the relative affinities of antibody fragments expressed in *Escherichia coli* by enzyme-linked immunosorbent assay. *Anal Biochem.* 253(1):37-45.
Watkins et al., 1998. Discovery of human antibodies to cell surface antigens by capture lift screening of phage-expressed antibody libraries. *Anal Biochem.* 256(2):169-77.
Weltzin et al., 1989. Binding and transepithelial transport of immunoglobulins by intestinal M cells: demonstration using monoclonal IgA antibodies against enteric viral proteins. *J Cell Biol.* 108(5):1673-85.
Weltzin et al., 1994. Intranasal Monoclonal Immunoglobulin A against Respiratory Syncytial Virus Protects against Upper and Lower Respiratory Tract Infections in Mice. *Antimicro Agents & Chemo.* 38(12):2785-2791.
Weltzin et al., 1996. Intranasal Monoclonal IgA Antibody to Respiratory Syncytial Virus Protects Rhesus Monkeys against Upper and Lower Tract Infection. *J. of Infect Dis.* 174:256-261.
Weltzin et al., 1999. Intranasal antibody prophylaxis for protection against viral disease. *Clin Microbiol Rev.* 12(3):383-93.
Whitlow et al., 1995. 1.85 A structure of anti-fluorescein 4-4-20 Fab. *Protein Eng.* 8(8):749-761.
Wilson et al., 1984. The structure of an antigenic determinant in a protein. *Cell.* 37:767-78.
Wright et al., 1982. Administration of a highly attenuated, live respiratory syncytial virus vaccine to adults and children. *Infect. Immun.* 37(1):397-400.
Wu et al, 1999. Humanization of murine monoclonal antibody by simultaneous optimization of framework and CDR residues. *J Mol Biol.* 294(1):151-62.
Wu et al., 2002. Tailoring Kinetics of Antibodies Using Focused Combinatorial Libraries chapter 13 from *Methods in Molecular Biology* vol. 207, Eds. Welschop and Krauss, Humana Press Inc., Totowa, NJ, pp. 213-233.
Wu et al., 1998. Stepwise in vitro affinity maturation of Vitaxin, an avb-specific Humanized mAb. *Proc. Natl. Acad. Sci. USA.* 95:6037-6042.
Wu et al., 2005. Ultra-potent Antibodies Against Respiratory Syncytial Virus: Effects of Binding Kinetics and binding Valence on Viral Neutralization. *J Mol Biol.* 350: 126-144.
Wu et al., 2007. Development of Motavizumab, an Ultra-potent Antibody for the Prevention of Respiratory Syncytial Virus Infection in the Upper and Lower Respiratory Trace. *J Mol Biol.* 368(3): 652-65.
Wu et al., 2008. Immunoprophylaxis of RSV Infection: Advancing from RSV-IGIV to Palivizumab and Motavizumab. *Curr Topics Microbiol Immunol.* 317:103-123.
Wyde et al., 1995 "Evaluation of the protective efficacy of reshaped human monoclonal antibody RSHZ 19 against respiratory syncytial virus in cotton rats," *Pediatr Res.* 38:543-50.
Yang et al., 1995. CDR walking mutagenesis for the affinity maturation of a potent human Anti-HIV-1 antibody into the picomolar range. *J Mol Biol.* 254:392-403.
Ye et al., 1997 "The BCL-6 proto-oncogene controls germinal-centre formation and Th2-type inflammation," *Nat. Genet.* 16:161-170.
U.S. Appl. No. 09/724,396; Office Action dated Mar. 26, 2002.
U.S. Appl. No. 09/724,396; Office Action dated Apr. 5, 2004.
U.S. Appl. No. 09/724,396; Office Action dated Jun. 3, 2003.
U.S. Appl. No. 09/724,396; Office Action dated Jul. 28, 2003.
U.S. Appl. No. 09/724,396; Office Action dated Dec. 3, 2002.
U.S. Appl. No. 09/724,531 (now U.S. Pat. No. 7,229,619); Office Action / Notice of Allowance dated Jan. 30, 2007.
U.S. Appl. No. 09/724,531 (now U.S. Pat. No. 7,229,619); Office Action / Notice of Allowance dated Aug. 22, 2006.
U.S. Appl. No. 09/724,531 (now U.S. Pat. No. 7,229,619); Office Action dated Feb. 9, 2005.
U.S. Appl. No. 09/724,531 (now U.S. Pat. No. 7,229,619); Office Action dated Feb. 21, 2003.
U.S. Appl. No. 09/724,531 (now U.S. Pat. No. 7,229,619); Office Action dated Apr. 4, 2006.
U.S. Appl. No. 09/724,531 (now U.S. Pat. No. 7,229,619); Office Action dated Jun. 4, 2004.
U.S. Appl. No. 09/724,531 (now U.S. Pat. No. 7,229,619); Office Action dated Jun. 15, 2005.
U.S. Appl. No. 09/724,531 (now U.S. Pat. No. 7,229,619); Office Action dated Oct. 21, 2003.
U.S. Appl. No. 09/771,415 (now U.S. Pat. No. 6,656,467); Office Action / Notice of Allowability dated May 6, 2003.
U.S. Appl. No. 09/771,415 (now U.S. Pat. No. 6,656,467); Office Action dated Feb. 10, 2003.
U.S. Appl. No. 09/771,415 (now U.S. Pat. No. 6,656,467); Office Action dated Jun. 18, 2002.
U.S. Appl. No. 09/796,848 (now U.S. Pat. No. 7,700,735); Office Action / Notice of Allowance dated Nov. 16, 2009.
U.S. Appl. No. 09/796,848 (now U.S. Pat. No. 7,700,735); Office Action dated Jan. 22, 2009.
U.S. Appl. No. 09/796,848 (now U.S. Pat. No. 7,700,735); Office Action dated Apr. 4, 2006.
U.S. Appl. No. 09/796,848 (now U.S. Pat. No. 7,700,735); Office Action dated Apr. 14, 2008.

(56) References Cited

OTHER PUBLICATIONS

U.S. Appl. No. 09/796,848 (now U.S. Pat. No. 7,700,735); Office Action dated Jun. 18, 2002.
U.S. Appl. No. 09/796,848 (now U.S. Pat. No. 7,700,735); Office Action dated Jul. 13, 2005.
U.S. Appl. No. 09/796,848 (now U.S. Pat. No. 7,700,735); Office Action dated Jul. 27, 2007.
U.S. Appl. No. 09/796,848 (now U.S. Pat. No. 7,700,735); Office Action dated Oct. 29, 2004.
U.S. Appl. No. 09/796,848 (now U.S. Pat. No. 7,700,735); Office Action dated Dec. 29, 2003.
U.S. Appl. No. 09/996,265 (now U.S. Pat. No. 6,855,493); Office Action / Notice of Allowability dated Mar. 31, 2004.
U.S. Appl. No. 09/996,265 (now U.S. Pat. No. 6,855,493); Office Action / Supplemental Notice of Allowability dated Jul. 13, 2004.
U.S. Appl. No. 09/996,265 (now U.S. Pat. No. 6,855,493); Office Action dated Aug. 12, 2003.
U.S. Appl. No. 09/996,288 (now U.S. Pat. No. 6,818,216); Office Action / Notice of Allowability dated Jan. 29, 2004.
U.S. Appl. No. 09/996,288 (now U.S. Pat. No. 6,818,216); Office Action / Notice of Allowability dated Jun. 30, 2004.
U.S. Appl. No. 09/996,288 (now U.S. Pat. No. 6,818,216); Office Action / Supplemental Notice of Allowability dated Jul. 28, 2004.
U.S. Appl. No. 09/996,288 (now U.S. Pat. No. 6,818,216); Office Action dated Jul. 14, 2003.
U.S. Appl. No. 10/020,354 (now U.S. Pat. No. 7,083,784); Office Action / Notice of Allowability dated Dec. 15, 2005.
U.S. Appl. No. 10/020,354 (now U.S. Pat. No. 7,083,784); Office Action dated Apr. 7, 2004.
U.S. Appl. No. 10/020,354 (now U.S. Pat. No. 7,083,784); Office Action dated Jun. 1, 2005.
U.S. Appl. No. 10/020,354 (now U.S. Pat. No. 7,083,784); Office Action dated Nov. 17, 2004.
U.S. Appl. No. 10/403,180 (now U.S. Pat. No. 7,179,900); Office Action / Notice of Allowability dated Sep. 6, 2006.
U.S. Appl. No. 10/403,180 (now U.S. Pat. No. 7,179,900); Office Action dated Mar. 30, 2006.
U.S. Appl. No. 10/403,180 (now U.S. Pat. No. 7,179,900); Office Action dated Apr. 4, 2005.
U.S. Appl. No. 10/403,180 (now U.S. Pat. No. 7,179,900); Office Action dated Oct. 19, 2005.
U.S. Appl. No. 10/461,863 (now U.S. Pat. No. 7,425,618); Office Action / Notice of Allowability dated Nov. 19, 2007.
U.S. Appl. No. 10/461,863 (now U.S. Pat. No. 7,425,618); Office Action dated Jun. 11, 2007.
U.S. Appl. No. 10/461,863 (now U.S. Pat. No. 7,425,618); Office Action dated Dec. 18, 2006.
U.S. Appl. No. 10/461,863 (now U.S. Pat. No. 7,425,618); Supplemental Notice of Allowability dated Jul. 31, 2008.
U.S. Appl. No. 10/461,904 (now U.S. Pat. No. 7,132,100); Office Action / Notice of Allowability dated May 2, 2006.
U.S. Appl. No. 10/461,904 (now U.S. Pat. No. 7,132,100); Office Action / Notice of Allowability dated Nov. 25, 2005.
U.S. Appl. No. 10/461,904 (now U.S. Pat. No. 7,132,100); Office Action dated Dec. 14, 2004.
U.S. Appl. No. 10/657,363; Interview Summary dated Oct. 8, 2009.
U.S. Appl. No. 10/657,363 (U.S. Publ. No. 2004/0131609); Office Action / Notice of Allowability dated Dec. 31, 2008.
U.S. Appl. No. 10/657,363 (U.S. Publ. No. 2004/0131609); Office Action / Notice of Allowability dated Feb. 4, 2010.
U.S. Appl. No. 10/657,363 (U.S. Publ. No. 2004/0131609); Office Action dated May 30, 2007.
U.S. Appl. No. 10/657,363 (U.S. Publ. No. 2004/0131609); Office Action dated Jul. 6, 2009.
U.S. Appl. No. 10/657,363 (U.S. Publ. No. 2004/0131609); Office Action dated Dec. 14, 2007.
U.S. Appl. No. 10/900,230 (now U.S. Pat. No. 7,635,568); Interview Summary dated Mar. 27, 2009.
U.S. Appl. No. 10/900,230 (now U.S. Pat. No. 7,635,568); Office Action / Notice of Allowance dated Jun. 17, 2009.
U.S. Appl. No. 10/900,230 (now U.S. Pat. No. 7,635,568); Office Action / Notice of Allowance dated Jun. 27, 2007.
U.S. Appl. No. 10/900,230 (now U.S. Pat. No. 7,635,568); Office Action dated Jan. 24, 2006.
U.S. Appl. No. 10/900,230 (now U.S. Pat. No. 7,635,568); Office Action dated Feb. 21, 2008.
U.S. Appl. No. 10/900,230 (now U.S. Pat. No. 7,635,568); Office Action dated Jun. 30, 2006.
U.S. Appl. No. 10/900,230 (now U.S. Pat. No. 7,635,568); Office Action dated Sep. 18, 2008.
U.S. Appl. No. 10/900,230 (now U.S. Pat. No. 7,635,568); Office Action dated Dec. 26, 2006.
U.S. Appl. No. 10/962,285 (now U.S. Pat. No. 7,323,172); Office Action / Notice of Allowability dated Sep. 6, 2007.
U.S. Appl. No. 10/962,285 (now U.S. Pat. No. 7,323,172); Office Action dated Apr. 13, 2007.
U.S. Appl. No. 10/962,285 (now U.S. Pat. No. 7,323,172); Office Action dated Oct. 26, 2006.
U.S. Appl. No. 11/263,230 (U.S. Publ. No. 2006/0115485); Office Action dated Jan. 9, 2008.
U.S. Appl. No. 11/263,230 (U.S. Publ. No. 2006/0115485); Office Action dated Mar. 30, 2009.
U.S. Appl. No. 11/263,230 (U.S. Publ. No. 2006/0115485); Office Action dated Oct. 2, 2008.
U.S. Appl. No. 11/362,267 (now U.S. Pat. No. 7,294,336); Office Action / Notice of Allowability dated Aug. 6, 2007.
U.S. Appl. No. 11/362,267 (now U.S. Pat. No. 7,294,336); Office Action dated May 4, 2007.
U.S. Appl. No. 11/397,328 (now U.S. Pat. No. 7,670,600); Office Action / Notice of Allowability dated Aug. 7, 2008.
U.S. Appl. No. 11/397,328 (now U.S. Pat. No. 7,670,600); Office Action dated Feb. 13, 2009.
U.S. Appl. No. 11/397,328 (now U.S. Pat. No. 7,670,600); Office Action dated Oct. 18, 2007.
U.S. Appl. No. 11/397,328 (now U.S. Pat. No. 7,670,600); Issue Fee Payment for dated Dec. 23, 2009.
U.S. Appl. No. 11/397,328 (now U.S. Pat. No. 7,670,600); Notice of Allowance and Fees due dated Sep. 29, 2009.
U.S. Appl. No. 11/643,982 (now U.S. Pat. No. 7,553,489); Office Action / Notice of Allowability dated Feb. 13, 2009.
U.S. Appl. No. 11/643,982 (now U.S. Pat. No. 7,553,489); Office Action dated Sep. 2, 2008.
U.S. Appl. No. 11/649,455 (now U.S. Pat. No. 7,704,497); Office Action dated Feb. 26, 2009.
U.S. Appl. No. 11/649,455 (now U.S. Pat. No. 7,704,497); Notice of Allowance and Fees due dated Nov. 24, 2009.
U.S. Appl. No. 11/906,543 (now U.S. Pat. No. 7,785,592); Office Action / Notice of Allowability dated Mar. 16, 2010.
U.S. Appl. No. 11/906,543 (now U.S. Pat. No. 7,785,592); Office Action dated Jun. 12, 2009.
U.S. Appl. No. 11/906,543 (now U.S. Pat. No. 7,785,592); Office Action dated Apr. 7, 2009.
U.S. Appl. No. 11/906,543 (now U.S. Pat. No. 7,785,592); Office Action dated Oct. 19, 2009.
U.S. Appl. No. 12/075,197 (U.S. Publ. No. 2009/0175883); Office Action / Interview Summary dated Jul. 22, 2010.
U.S. Appl. No. 12/075,197 (U.S. Publ. No. 2009/0175883); Office Action dated Mar. 26, 2010.
U.S. Appl. No. 12/075,197 (U.S. Publ. No. 2009/0175883); Office Action dated Nov. 16, 2010.
U.S. Appl. No. 12/075,197 (U.S. Publ. No. 2009/0175883); Office Action dated Apr. 28, 2011.
U.S. Appl. No. 12/476,183; Notice of Allowance and Fees due dated Jul. 14, 2010.
U.S. Appl. No. 12/559,375 (U.S. Publ. No. 2010/0098708); Office Action dated Jun. 17, 2010.
U.S. Appl. No. 12/691,433 (now U.S. Pat. No. 8,012,476); Notice of Allowability dated Apr. 28, 2011.
U.S. Appl. No. 12/691,433 (now U.S. Pat. No. 8,012,476); Office Action dated Nov. 5, 2010.
U.S. Appl. No. 12/707,527 (now U.S. Pat. No. 8,153,133); Notice of Allowability dated Dec. 2, 2011.

(56) References Cited

OTHER PUBLICATIONS

U.S. Appl. No. 12/707,527 (now U.S. Pat. No. 8,153,133); Office Action dated Feb. 25, 2011.
U.S. Appl. No. 12/707,527 (now U.S. Pat. No. 8,153,133); Office Action dated Jul. 29, 2011.
U.S. Appl. No. 12/707,527 (now U.S. Pat. No. 8,153,133); Office Action dated Dec. 9, 2010.
U.S. Appl. No. 12/777,814 (U.S. Publ. No. 2010/0266614); Office Action dated Jun. 24, 2011.
U.S. Appl. No. 12/777,814; Office Action dated Nov. 12, 2010.
U.S. Appl. No. 12/817,097 (now U.S. Pat. No. 8,007,793); Notice of Allowability dated Apr. 18, 2011.
U.S. Appl. No. 12/817,097 (now U.S. Pat. No. 8,007,793); Office Action dated Dec. 1, 2010.
U.S. Appl. No. 12/969,514 (U.S. Publ. No. 2011/0158985); Office Action dated Dec. 15, 2011.
U.S. Appl. No. 13/184,455 (U.S. Publ. No. 2012/0039876); Notice of Allowability dated Mar. 1, 2012.
International Preliminary Report on Patentability of International application No. PCT/NL2008/050333, dated Dec. 1, 2009.
International Search Report of International application No. PCT/NL2008/050333, dated Dec. 30, 2008.
Office Action of U.S. Appl. No. 12/898,325, dated Aug. 17, 2012.
Office Action of U.S. Appl. No. 12/898,325, dated Nov. 6, 2012.
Office Action dated Oct. 15, 2015 for New Zealand patent application No. 621824; 2 pgs.
Office Action dated Oct. 15, 2015 for New Zealand patent application No. 712667; 4 pgs.

Figure 5
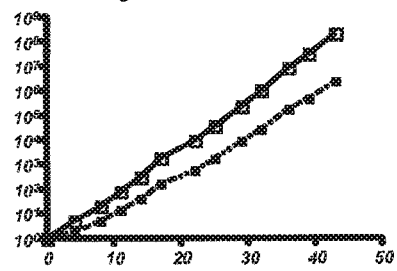
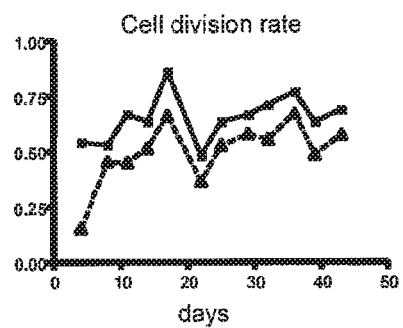
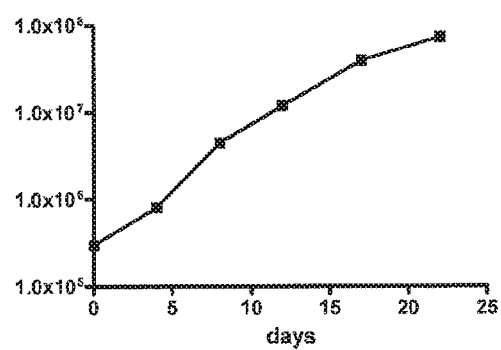

■ neg ctrl (cult sup)
■ pos ctrl (Ridascreen)
■ D25 (cult sup)

■ VSV + D25
■ VSV-G + D25
■ VSV-F + D25

Figure 11A

Anti-RSV clone B63D10-D25

Nucleotide sequence VH region (V-D-J segments) (SEQ ID NO.:9)
CAGGTGCAGCTGGTACAGTCTGGGGCTGAAGTGAAGAAGCCTGGGCTCCTCGGTGATGGTCCTGCCAGGCTCTGGAGGCCCCCTCAGAAACTAT
ATTATCAACTGGCTACGACAGGCCCCTGAGTGGATGGGAGGGATCATTCCTGTCTTGGGTACAGTACACTACGACCGAAGTTC
CAGGGCAGAGTCACGATTACCGGGGACGAATCCACAGACACAGCCTACATCCATCGATCAGCCTGAGATCTGAGGACACGGCCATGTATTACTGT
GCGACGGAAACAGCTCTGGTTGTATCTACTACCTACCACACTACTTTGACAACTGGGCCCAGGGAACCCTGGTCACCGTCTCCTCAG Amino acid sequence VH region (V-D-J segments) (SEQ ID NO.:7)
QVQLVQSGAEVKKPGSSVMVSCQASGGPLRNYIINWLRQAPGQGPEWMGGIIPVLGTVHYAPKFQGRVTITADESTDTAYIHLISLRSEDTAMYYC
ATETALVVSTTYLPHYFDNWGQGTLVTVSS Nucleotide sequence VL region (V-J segments) (SEQ ID NO.:10)
GACATCCAGATGACCCAGTCTCCATCCTCCCTGTCTGCAGCTGTAGGAGACAGAGTCACCATCACTTGCCAGGCGAGTCAGGACGTCAGGACATTGTCAACTAT
TTAAATTGGTATCAACAGAAACCAGGGAAAGCCCCTAAGCTCCTGATCTACGTTGCATCCATCCAATTTGGAGACAGGGGTCCCATCAAGGTTCAGTGGA
AGTGGATCTGGGACAGATTTAGTCTCACCATCAGCAGCCTGCAGCCTGAAGATGTTGCAACATATTATTGTCAACATATGATAATCTCCCACTC
ACATTCGGCGGAGGGACCAAGGTTGAGATCAAAAGA Amino acid sequence VL region (V-J segments) (SEQ ID NO.:8)
DIQMTQSPSSLSAAVGDRVTITCQASQDIVNYLNWYQQKPGKAPKLLIYVASNLETGVPSRFSGSGSGTDFSLTISSLQPEDVATYYCQQYDNLPL
TFGGGTKVEIKR

Figure 11B heavy chain sequence of clone B63D10-D25 compared to germline

```
             |------Fr1------|[--CDR1--]|-----Fr2-----|[---CDR2---]|------Fr3------|[------CDR3------]|---Fr4---|
VH1-69 germl. QVQLVQSGAEVKKPGSSVKVSCKASGGTFS SYAIS WVRQAPGQGLEWMG GIIPIFGTANYAQKFQG RVTITADESTSTAYMELSSLRSEDTAVYYCAR                         (SEQ ID NO.: 55)
              *    *                 ****  * ****                       ** *          *** *  *
#7. B63D10-D25 QVQLVQSGAEVKKPGSSVWVSCQASGGFLR NYIIN WLRQAPGQGPEWMG GIIPVLGTVHYAPKFQG RVTITADESTDTAYIHLLSLRSEDTAMYYCAT ETALVSTYLPHYFDN WGQGTLVTVSS
                                                                                                                           (SEQ ID NO.: 7)
```

V name is IGHV1-69*01
D name is IGHD5-5*01
J name is IGHJ4*02

Figure 11C light chain sequence of clone B63D10-D25 compared to germline

```
             |-----Fr1-----|[---CDR1---]|-----Fr2-----|[-CDR2-]|------Fr3------|[---CDR3---]|---Fr4---|
VkI 08/018   DIQMTQSPSSLSASVGDRVTITC QASQDISNYLN WYQQKPGKAPKLLIY DASNLET GVPSRFSGSGSGTDFTFTISSLQPEDIATYYC QQYDNLP                      (SEQ ID NO.: 57)
              *                                                                     *
#7. B63D10-D25 DIQMTQSPSSLSAAVGDRVTIC QASQDIVNYLN WYQQKPGKAPKLLIY VASNLET GVPSRFSGSGSGTDFSLTISSLQPEDVATYYC QQYDNLP LTFGGGTKVEIKRTV
                                                                                                                (SEQ ID NO.: 8)
```

V name is IGKV1-33*01
J name is IGKJ4*01

Figure 12

VH region codon optimization:

```
                         1                                                50
RSV#D25-IGVH1-69         CAGGTGCAGCTGGTACAGTCTGGGGCTGAAGTGAAGAAGCCTGGGTCCTC
RSV#D25-VH Optimized     CAGGTGCAGCTGGTGCAGAGCGGAGCCGAGGTGAAGAAACCCGGCAGCAG 51                                               100
RSV#D25-IGVH1-69         GGTGATGGTCTCCTGCCAGGCCTCTGGAGGCCCCCTCAGAAACTATATTA
RSV#D25-VH Optimized     CGTGATGGTGTCCTGCCAGGCCAGCGGCGGACCCCTGCGGAACTACATCA 101                                              150
RSV#D25-IGVH1-69         TCAACTGGCTACGACAGGCCCCTGGACAAGGCCCTGAGTGGATGGGAGGG
RSV#D25-VH Optimized     TCAACTGGCTGCGGCAGGCCCCAGGCCAGGGCCCTGAGTGGATGGGCGGC 151                                              200
RSV#D25-IGVH1-69         ATCATTCCTGTCTTGGGTACAGTACACTACGCACCGAAGTTCCAGGGCAG
RSV#D25-VH Optimized     ATCATCCCCGTGCTGGGCACCGTGCACTACGCCCCCAAGTTCCAGGGCCG 201                                              250
RSV#D25-IGVH1-69         AGTCACGATTACCGCGGACGAATCCACGGACACAGCCTACATCCATCTGA
RSV#D25-VH Optimized     GGTGACCATCACCGCCGACGAGAGCACCGACACCGCCTACATCCACCTGA 251                                              300
RSV#D25-IGVH1-69         TCAGCCTGAGATCTCAGGACACGGCCATGTATTACTGTGCGACGGAAACA
RSV#D25-VH Optimized     TCAGCCTGCGGAGCGAGGACACCGCCATGTACTACTGCGCCACCGAGACC 301                                              350
RSV#D25-IGVH1-69         GCTCTGGTTGTATCTACTACCTACCTACCACACTACTTTGACAACTGGGG
RSV#D25-VH Optimized     GCCCTGGTGGTGTCCACCACCTACCTGCCCCACTACTTCGACAACTGGGG 351             378
RSV#D25-IGVH1-69         CCAGGGAACCCTGGTCACCGTCTCCTCA     (SEQ ID NO.: 139)
RSV#D25-VH Optimized     CCAGGGCACCCTGGTGACAGTCTCGAGT     (SEQ ID NO.: 140)
```

VL region codon optimization:

```
                         1                                                50
RSV#D25-IGKV1-33         GACATCCAGATGACCCAGTCTCCATCCTCCCTGTCTGCAGCTGTAGGAGA
RSV#D25-VL Optimized     GACATCCAGATGACCCAGAGCCCCAGCAGCCTGTCTGCCGCCGTGGGCGA 51                                               100
RSV#D25-IGKV1-33         CAGAGTCACCATCACTTGCCAGGCGAGTCAGGACATTGTCAACTATTTAA
RSV#D25-VL Optimized     CCGGGTGACCATCACCTGCCAGGCCAGCCAGGACATCGTGAACTACCTGA 101                                              150
RSV#D25-IGKV1-33         ATTGGTATCAACAGAAACCAGGGAAAGCCCCTAAGCTCCTGATCTACGTT
RSV#D25-VL Optimized     ACTGGTATCAGCAGAAGCCCGGCAAGGCCCCCAAGCTGCTGATCTACCTC 151                                              200
RSV#D25-IGKV1-33         GCATCCAATTTGGAGACAGGGGTCCCATCAAGGTTCAGTGGAAGTGGATC
RSV#D25-VL Optimized     GCCAGCAACCTGGAAACCGGCGTGCCCAGCCGGTTTAGCGGCAGCGGCTC 201                                              250
RSV#D25-IGKV1-33         TGGGACAGATTTTAGTCTCACCATCAGCAGCCTGCAGCCTGAAGATGTTC
RSV#D25-VL Optimized     CGGCACCGACTTCAGCCTGACCATCAGCAGCCTGCAGCCCGAGGACGTGG 251                                              300
RSV#D25-IGKV1-33         CAACATATTATTGTCAACAATATGATAATCTCCCACTCACATTCGGCGGA
RSV#D25-VL Optimized     CCACCTACTACTGCCAGCAGTACGACAACCTGCCCCTGACCTTTGGCGGC 301             326
RSV#D25-IGKV1-33         GGGACCAAGGTTGAGATCAAAAGAAC      (SEQ ID NO.: 141)
RSV#D25-VL Optimized     GGAACAAAGGTGGAGATCAAGCGGAC      (SEQ ID NO.: 142)
```

Figure 13A
Table 3
| 5 mice p/g | 5 mice p/g |
|---|---|
| 2 mg/kg | ctrl IgG1 |
|  | Synagis |
|  | D25 |
| 1 mg/kg | D25 |
| 0,5 mg/kg | D25 |
day  0  5
 ↑   ↑  ↑
 Ig virus analysis
Figure 13B
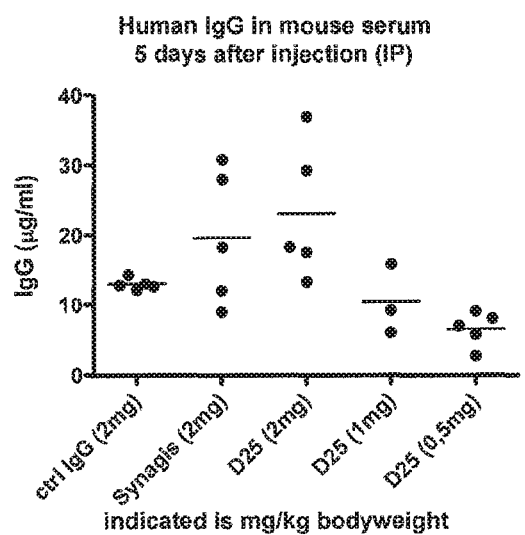
Figure 13C
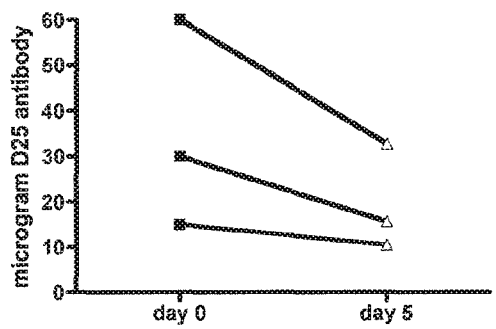

10X magnification. The arrow indicates cellular infiltration into the lungs, which is mostly Seen around the bronchi. Below are another set of histology pictures taken from difference mice treated with Synagis or D25.

Figure 13G
Muis 6 Synagis 2mg
10x
50x
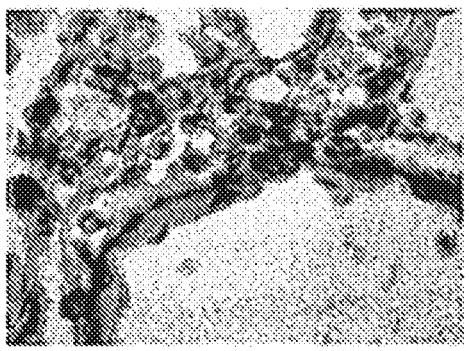
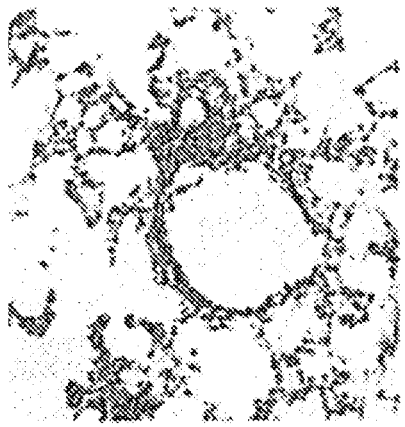
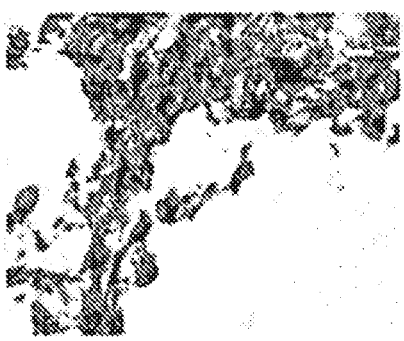
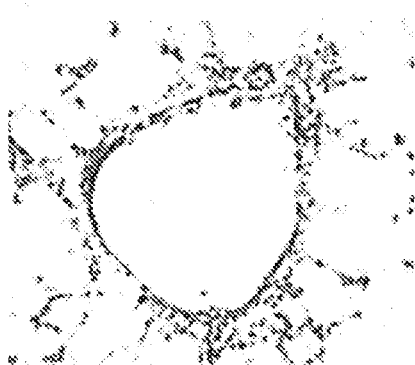
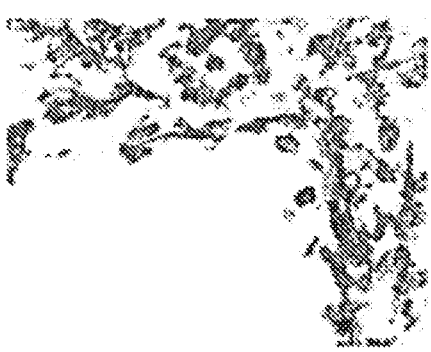

Muis 9 Synagis 2mg

Figure 13J
Muis 14 D10-D25 2mg
10x              50x
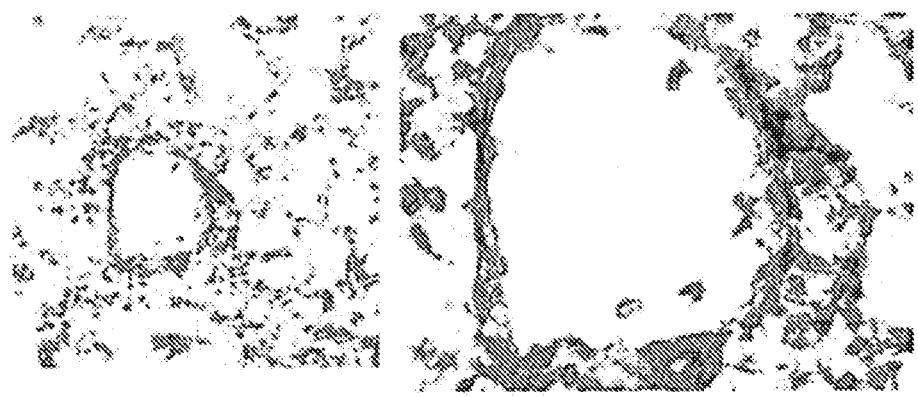
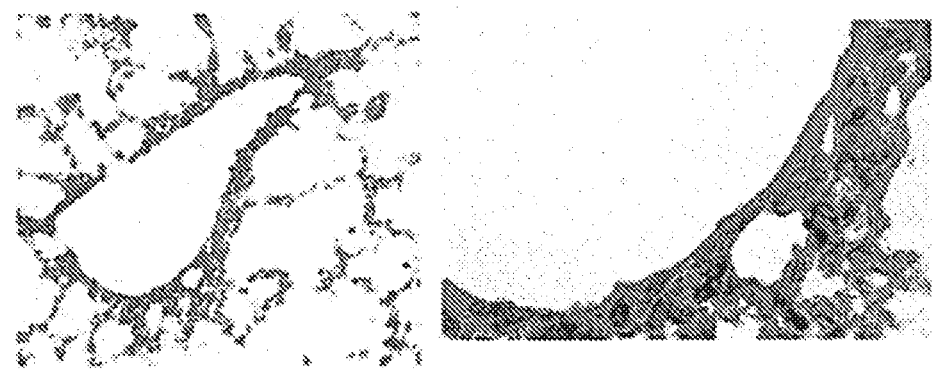

Figure 14A

Anti-RSV clone AM14

Nucleotide sequence VH region AM14 (V-D-J segments)
GAGGTGCAGCTGGTGGAGTCTGGGGGAGGCGTGGTCCAGCCTGGGAGGTCCCTGAGACTCTCCTGTGCGGCCTCTGGATTCAGTTCAGTCACTAT
GCCATGCACTGGGTCCGCCAGGCTCCAGGCAAGGGACTGGAGTGGGTGGCAGTTATATCTTATGATGGAGAAAATACATATTACGCAGACTCCGTG
AAGGGCCGATTCTCCATCTCCAGAGACAATTCCAAGAACACAGTGTCTCTGCAAATGAACAGCCTGAGAACTGAGGACACGGCTCTATATTACTGT
GCGAGAGACCGCATAGTGGACGACTACTACTACGGTATGGACGTCTGGGGCCAAGGGACCACGGTCACCGTCTCCTCA (SEQ ID NO.:101)

Amino acid sequence VH region AM14 (V-D-J segments)
EVQLVESGGGVVQPGRSLRLSCAASGFSFSHYAMHWVRQAPGKGLEWVAVISYDGENTYYADSVKGRFSISRDNSKNTVSLQMNSLRTEDTALYYC
ARDRIVDDYYYGMDVWGQGATVTVSS (SEQ ID NO.:78)

Nucleotide sequence VL region AM14 (V-J segments)
GACATCCAGATGACCCAGTCTCCATCTTCCCTGTCTGCATCTGTAGGAGACAGAGTCACCATCACTTGCCAGGCGAGTCAGGACATTAAGAAGTAT
TTAAATTGGTATCATCAGAAACCAGGGAAAGTCCCTGAGCTCCTGATGCACGATGCATCCAATTTGGAAACAGGGGTCCCATCAAGGTTCAGTGGC
AGGGGATCTGGGACAGATTTTACTCTCACCATTAGCAGCCTGCAGCCTGAAGATATTGGAACAGTATTACTGTCAACAGTATGATAATCTGCCTCCG
CTCACTTTCGGCGGAGGGACCAAGGTGGAGATCAAACGAACTGTG (SEQ ID NO.:108)

Amino acid sequence VL region AM14 (V-J segments)
DIQMTQSPSSLSASVGDRVTITCQASQDIKKYLNWYHQKPGKVPELLMHDASNLETGVPSRFSGRGSGTDFTLTISSLQPEDIGTYYCQQYDNLPP
LTFGGGTKVEIKRTV (SEQ ID NO.:79)

Figure 14B heavy chain sequence of clone AM14 compared to germline

```
                    -----Fr1-------    [-CDR1-]    -----Fr2------    [-CDR2-]    -----------------Fr3-----------------    [---CDR3----] ----Fr4---
IGHV3-30 germl.    QVQLVESGGGVVQPGRSLRLSCAAS  GFTFSSYG  MHWVRQAPGKGLEWVAV  ISYDGSNK  YYADSVKGRFTISRDNSKNTLYLQMNSLRAEDTAVYYC  AR              (SEQ ID NO: 147)
                    *                                                                  *         *                *                *
AM14 VH            EVQLVESGGGVVQPGASLRLSCAAS  GFSFSHYA  MHWVRQAPGKGLEWVAV  ISYDGENT  YYADSVKGRFSISRDNSKNTVSLQMNSLRPEDTALYYC  ARDRIVDDYYYGMDV WGQGATVTVSS
                                                                                                                                       (SEQ ID NO: 78)
```

V gene: IGHV3-30*04
D gene: IGHD5-12*01
J gene: IGHJ6*02 light chain sequence of clone AM14 compared to germline

```
                    --------Fr1---------    [CDR1]    ------Fr2------    [CDR2]   ----------------Fr3----------------    [---CDR3---] ----Fr4---
IGKV1-33 germl.    DIQMTQSPSSLSASVGDRVTITCQAS  QDISNY  LNWYQQKPGKAPKLLIY  DAS      NLETGVPSRFSGSGSGTDFTFTISSLQPEDIATYYC  QQYDNLP LT  (SEQ ID NO: 148)
                    *                          **                        **       **                                    *
AM14 VL            DIQMTQSPSSLSASVGDRVTITCQAS  QDIKKY  LNWYKQKPGNVPELLMH  DAS      NLETGVPSRFSGRGSGTDFTWTISSLQPEDIGTGYYC  QQYDNLP LT  FGGGTKVEIKKRTV
                                                                                                                                       (SEQ ID NO: 79)
```

V gene: IGKV1-33*01
J gene: IGKJ4*01

Figure 14C

CDR sequences of AM14

| | |
|---|---|
| heavy chain CDR1 sequence | GFSFSHYA (SEQ ID NO.: 173) |
| heavy chain CDR2 sequence | ISYDGENT (SEQ ID NO.: 74) |
| heavy chain CDR3 sequence | ARDRIVDDYYYYGMDV (SEQ ID NO.: 75) |
| light chain CDR1 sequence | QDIKKY (SEQ ID NO.: 76) |
| light chain CDR2 sequence | DAS |
| light chain CDR3 sequence | QQYDNLPPLT (SEQ ID NO.: 77) |

Nucleotide sequence VHeavy region AM14 (V-D-J segments)

FR1:
GAGGTGCAGCTGGTGGAGTCTGGGGGAGGCGTGGTCCAGCCTGGGAGGTCCCTGAGACTCTC
CTGTGCGGCCTCT (SEQ ID NO.: 94)

CDR1:
GGATTCAGCTTCAGTCACTATGCC (SEQ ID NO.: 95)

FR2:
ATGCACTGGGTCCGCCAGGCTCCAGGCAAGGGACTGGAGTGGGTGGCAGTT (SEQ ID NO.: 96)

CDR2:
ATATCTTATGATGGAGAAAATACA (SEQ ID NO.: 97)

FR3:
TATTACGCAGACTCCGTGAAGGGCCGATTCTCCATCTCCAGAGACAATTCCAAGAACACAGT
GTCTCTGCAAATGAACAGCCTGAGACCTGAGGACACGGCTCTATATTACTGT (SEQ ID NO.: 98)

CDR3:
GCGAGAGACCGCATAGTGGACGACTACTACTACTACGGTATGGACGTC (SEQ ID NO.: 99)

FR4:
TGGGGCCAAGGGGCCACGGTCACCGTCTCCTCAG (SEQ ID NO.: 100)

Figure 14D

Nucleotide sequence VLight region AM14 (V-J segments)

FR1:
GACATCCAGATGACCCAGTCTCCATCTTCCCTGTCTGCATCTGTAGGAGACAGAGTCACCAT
CACTTGCCAGGCGAGT (SEQ ID NO.: 102)

CDR1:
CAGGACATTAAGAAGTAT (SEQ ID NO.: 103)

FR2:
TTAAATTGGTATCATCAGAAACCAGGGAAAGTCCCTGAGCTCCTGATGCAC (SEQ ID NO.: 104)

CDR2:
GATGCATCC

FR3:
AATTTGGAAACAGGGGTCCCATCAAGGTTCAGTGGCAGGGGATCTGGGACAGATTTTACTCT
CACCATTAGCAGCCTGCAGCCTGAAGATATTGGAACATATTACTGT (SEQ ID NO.: 105)

CDR3:
CAACAGTATGATAATCTGCCTCCGCTCACT (SEQ ID NO.: 106)

FR4:
TTCGGCGGAGGGACCAAGGTGGAGATCAAAC (SEQ ID NO.: 107)

Figure 14E

Anti-RSV clone AM16

Nucleotide sequence VH region AM16 (V-D-J segments)
GAGGTGCAGCTGGTGGAGTCGGGGGGAGGCGGGGGAGGCCTGGCCCAGCCTGGGGGGTCCCTGAGACTCTCCTGTGCAGCCTCTGGATTCACATTCAGTAGTTAT
AACATGAACTGGGTCCGCCAGGCTCCAGGGAAGGGGCTGGAGTGGGTCTCACACATTAGTGCGGGTAGTAGTTACATATACTACTCAGACTCAGTG
AAGGGCCGATTCACCGTCTCCAGAGACAACGTCAGGAACTCAGTATATCTGCAAATGAACAGCCTGAGAGCCGTGACGGCTGTGTATTACTGT
GCGAGAGAGGATTATGGTCCGGGAAATTATTATAGTCCTAACTGGTTCGACCCCTGGGGCCAGGGAACCCTGGTCACCGTCTCCTCA
(SEQ ID NO.: 116)

Amino acid sequence VH region AM16 (V-D-J segments)
EVQLVETGGGLAQPGGSLRLSCAASGFTFSSYNMNWVRQAPGKGLEWVSHISAGSSYIYYSDSVKGRFTVSRDNVRNSVYLQMNSLRAADTAVYYC
AREDYGPGNYYSPNWFDPWGQGTLVTVSS (SEQ ID NO.: 85)

Nucleotide sequence VL region AM16 (V-J segments)
CAGTCTGTGCTGACGCAGCCGCCCTCAGTGTCTGGGGCCCCAGGGCAGAGAGTCACCATCTCCTGCACTGGGAGCAGCTCCAACATCGGGGCAGGT
TATGATGTACACTGGTACCAGCAGCTTCCAGGAACAGCCCCAAACTCCTCATCTATGGCAACACTAATCGGCCCTCAGGGGTCTCCGACCGATTC
TCTGGCTCCAAGTCTGGCACCTCAGCTCGCCTCAGCCTCCCTGGCCATCACTGGACTCCAGGCTGAGGATGAGGCTGATTATTACTGCCACTCCTATGACAGAAGC
CTGAGTGGTTCAGTATTCGGCGGAGGGACCAAGCTGACCGTC (SEQ ID NO.: 123)

Amino acid sequence VL region AM16 (V-J segments)
QSVLTQPPSVSGAPGQRVTISCTGSSSNIGAGYDVHWYQQLPGTAPKLLIYGNTNRPSGVSDRFSGSKSGTSASLAITGLQAEDEADYYCHSYDRS
LSGSVFGGGTKLTV (SEQ ID NO.: 86)

Figure 14F heavy chain sequence of clone AM16 compared to germline

```
                   ------Fr1---------  [-CDR1-]  --------Fr2--------  [-CDR2-]  -------------Fr3---------------                        [---CDR3---]  ----Fr4----
IGHV3-21 germl.    EVQLVESGGGLVKPGGSLRLSCAAS GFTFSSYS MNWVRQAPGKGLEWVSS ISSSSSYI YYADSVKGRFTISRDNAKNSLYLQMNSLRAEDTAVYYC AR                            (SEQ ID NO: 153)
AM16 VH            EVQLVETGGGLAQPGGSLRLSCAAS GFTFSSYN MNWVRQAPGKGLEWVSH ISSAGSSYI YYSDSVKGRFTVSRDNVRNSVYLQMRSLRAACTAVYYC AREDYGPGNYISPNWFDP WGQGTLVTVSS
                                                                              *                                                                    (SEQ ID NO: 85)
```

V gene: IGHV3-21*01
D gene: IGHD3-10*01
J gene: IGHJ5*02 light chain sequence of clone AM16 compared to germline

```
                   ---------Fr1--------  [-CDR1-]  -----Fr2------  [CDR2]  ----------------Fr3----------------  [-CDR3-]  ---Fr4---
IGLV1-40 germl.    QSVVTQPPSVSGAPGQRVTISCTGS SSNIGAGYD VHWYQQLPGTAPKLLIY GNS  NRPSGVPDRFSGSKSGTSASLAITGLQAEDEADYYC QSYDSSLSG                (SEQ ID NO: 154)
AM16 VL            QSVVTQPPSVSGAPGQRVTISCTGS SSNIGAGYD VHWYQQLPGTAPKLLIY GNT  NRPSGVSDRFSGSKSGTSASLAITGLQAEDEADYYC HSYDRSLSG SVRGGGTKLTV
                                                                           *                                                           (SEQ ID NO: 86)
```

V gene: IGLV1-40*02
J gene: IGLJ2*01

Figure 14G

CDR sequences of AM16

| heavy chain CDR1 sequence | GFTFSSYN (SEQ ID NO. 80) |
| --- | --- |
| heavy chain CDR2 sequence | ISAGSSYI (SEQ ID NO. 81) |
| heavy chain CDR3 sequence | AREDYGPGNYYSPNWFDP (SEQ ID NO 82) |
| light chain CDR1 sequence | SSNIGAGYD (SEQ ID NO 83) |
| light chain CDR2 sequence | GNT |
| light chain CDR3 sequence | HSYDRSLSG (SEQ ID NO 84) |

Nucleotide sequence VHeavy region AM16 (V-D-J segments)

FR1:
GAGGTGCAGCTGGTGGAGACCGGGGGAGGCCTGGCCCAGCCTGGGGGGTCCCTGAGACTCTC
CTGTGCAGCCTCT (SEQ ID NO 109)

CDR1:
GGATTCACATTCAGTAGTTATAAC (SEQ ID NO 110)

FR2:
ATGAACTGGGTCCGCCAGGCTCCAGGGAAGGGGCTGGAGTGGGTCTCACAC (SEQ ID NO. 111)

CDR2:
ATTAGTGCGGGTAGTAGTTACATA (SEQ ID NO.: 112)

FR3:
TACTACTCAGACTCAGTGAAGGGCCGATTCACCGTCTCCAGAGACAACGTCAGGAACTCAGT
ATATCTGCAAATGAACAGCCTGAGAGCCGCTGACACGGCTGTGTATTACTGT (SEQ ID NO 113)

CDR3:
GCGAGAGAGGATTATGGTCCGGGAAATTATTATAGTCCTAACTGGTTCGACCCC (SEQ ID NO 114)

FR4:
TGGGGCCAGGGAACCCTGGTCACCGTCTCCTCAG (SEQ ID NO 115)

Figure 14H

Nucleotide sequence VLight region AM16 (V-J segments)

FR1:
CAGTCTGTCGTGACGCAGCCGCCCTCAGTGTCTGGGGCCCCAGGGCAGAGAGTCACCATCTC
CTGCACTGGGAGC (SEQ ID NO.: 117)

CDR1:
AGCTCCAACATCGGGGCAGGTTATGAT (SEQ ID NO.: 118)

FR2:
GTACACTGGTACCAGCAGCTTCCAGGAACAGCCCCCAAACTCCTCATCTAT (SEQ ID NO.: 119)

CDR2:
GGCAACACT

FR3:
AATCGGCCCTCAGGGGTCTCCGACCGATTCTCTGGCTCCAAGTCTGGCACCTCAGCCTCCCT
GGCCATCACTGGACTCCAGGCTGAGGATGAGGCTGATTATTACTGC (SEQ ID NO.: 120)

CDR3:
CACTCCTATGACAGAAGCCTGAGTGGT (SEQ ID NO.: 121)

FR4:
TCAGTATTCGGCGGAGGGACCAAGCTGACCGTCCTAG (SEQ ID NO.: 122)

Figure 141

Anti-RSV clone AM23

Nucleotide sequence VH region AM23 (V-D-J segments)
GAGGTGCAGCTGGTGGAGTCTGGGGGAGGCGTGGTCAAGCCTGGGGGGTCCCTGAGACTCTCCTGTGCAGCTTCTGGATTCAACTTCCATAACTAC
GGCATGAACTGGGTCCGCCAGGCTCCAGGGAAGGGGCTGGAGTGGGTGGCGGTTGTTGTTTGGTATGATGGAAGTAAGAAATACTATGCAGACTCCGTG
ACGGGCCGATTCGCCATCTCCAGAGACAATTCCAAGAACACTCTCTATCTGCAAATGAACAGCCTGAGAGTCGAGGACACGGCTGTTTATTATTGT
GTGAGAGATAAAGTGGACCGACTCCCTACTTTGACTCTCTGGGGCCAGGGAACCCTGGTCACCGTCTCGAGT (SEQ ID NO.: 131)

Amino acid sequence VH region AM23 (V-D-J segments)
EVQLVESGGGVVKPGGSLRLSCAASGFNFHNYGMNWVRQAPGKGLEWVAVVWYDGSKKYYADSVTGRFAISRDNSKNTLYLQMNSLRVEDTAVYYC
VRDKVGPTPYFDSWGQGTLVTVSS (SEQ ID NO.: 92)

Nucleotide sequence VL region AM23 (V-J segments)
TCCTATGTGCTGACTCAGCCCCCCTCGGTGTCACTGGCCCCAGGAGGACGGCCGGATCACCTGTGGAAGAAACACATTGGAAGTGAAACTGTG
CACTGGTACCAGCAGAAGCCAGGCCAGGCCCCTGTGCTGGTCGTCTATGATGATGATGATAGGACCGGATCCCTCAGGGATCCTGAGGCGATTCTCTGGCTCC
AACTCTGGGAACACAGCCGCCACCCTGACCATCAGCAGGGCCGACTATTACTGTCAGGTCTGGGATAGCAGTAATTATCAT
CAGGTATTCGGCGGAGGGACCAAGCTGACCGTC (SEQ ID NO.: 138)

Amino acid sequence VL region AM23 (V-J segments)
SYVLTQPPSVSLAPGGTAIITCGRNNIGSETVHWYQQKPGQAPVLVVYDDDDRPSGIPERFSGSNSGNTATLTISRVEAGDEADYYCQVWDRSNYH
QVFGGGTKLTV (SEQ ID NO.: 93)

Figure 14J heavy chain sequence of clone AM23 compared to germline

```
             |----Fr1----------|  |-CDR1-|  |----Fr2---------|  |-CDR2-|  |----Fr3--------------------------------------------|  |---CDR3---|  |--Fr4---
IGHV3-33 germl. QVQLVESGGGVVQPGRSLRLSCAAS  GFTFSSYG  MHWVRQAPGKGLEWVAV  IWYDGSNK  YYADSVKGRFTISRDNSKNTLYLQMNSLRAEDTAVYYC  AR            (SEQ ID NO.: 159)
AM23 VH         EVQLVESGGGVVRPGTSLRLSCAAT  GFMFERYG  MHKVRQAPGKGLSWVAV  VWYDGSKK  YYADSVTGRFAISRDNGKNTLYLQMNSLRVEDTAVYYC  VRGKVGTPYEDS MGQSTVVTSS
                                                                                                                                         (SEQ ID NO.: 92)
```

V gene: IGHV3-33*01
D gene: IGHD1-26*01
J gene: IGHJ4*02 light chain sequence of clone AM23 compared to germline

```
             |----Fr1---------------|  [CDR1]   |---Fr2--------|  [CDR2]  |--------Fr3--------------------------------|  [--CDR3---]  --Fr4---
IGLV3-21 germl. SYVLTQPPSVSVAPGQTARITCGGN  NIGSKS  VHWYQQKPGQAPVLVVY  DDS     DRPSGIPERFSGSNSGNTATLTISRVEAGDEADYYC  QVWDSSSDHV (SEQ ID NO.: 160)
AM23 VL         SYVLTQPSVSLAPGGTARITCGRV  NIGSET  VHWYQQKPGKAPVLVVT  DDD     DRPSGIPERFSGSNSGNTAPLTISRVEAGDEADYYC  QVWDKSNYRQV EGGTKLYV
                                                                                                                                 (SEQ ID NO.: 93)
```

V gene: IGLV3-21*02
J gene: IGLJ2*01

Figure 14K

CDR sequences of AM23

| heavy chain CDR1 sequence | GFNFHNYG (SEQ ID NO.: 87) |
|---|---|
| heavy chain CDR2 sequence | VWYDGSKK (SEQ ID NO.: 88) |
| heavy chain CDR3 sequence | VRDKVGPTPYFDS (SEQ ID NO.: 89) |
| light chain CDR1 sequence | NIGSET (SEQ ID NO.: 90) |
| light chain CDR2 sequence | DDD |
| light chain CDR3 sequence | QVWDRSNYHQV (SEQ ID NO.: 91) |

Nucleotide sequence VHeavy region AM23 (V-D-J segments)

FR1:
CAGGTGCAACTGGTGGAGTCTGGGGGAAATGTGGTCAAGCCTGGGACGTCCCTGAGACTGTC
CTGTGCAGCGACT (SEQ ID NO.: 124)

CDR1:
GGATTCAACTTCCATAACTACGGC (SEQ ID NO.: 125)

FR2:
ATGAACTGGGTCCGCCAGGCTCCAGGCAAGGGGCTGGAGTGGGTGGCGGTT (SEQ ID NO.: 126)

CDR2:
GTTTGGTATGATGGAAGTAAGAAA (SEQ ID NO.: 127)

FR3:
TACTATGCAGACTCCGTGACGGGCCGATTCGCCATCTCCAGAGACAATTCCAAGAACACTCT
GTATCTGCAAATGAACAGCCTGAGAGTCGAGGACACGGCTGTTTATTATTGT (SEQ ID NO.: 128)

CDR3:
GTGAGAGATAAAGTGGGACCGACTCCCTACTTTGACTCC (SEQ ID NO.: 129)

FR4:
TGGGGCCAGGGAACCCTGGTCACCGTATCCTCAG (SEQ ID NO.: 130)

Figure 14L

Nucleotide sequence VLight region AM23 (V-J segments)

FR1:
TCCTATGTGCTGACTCAGCCACCCTCGGTGTCACTGGCCCCAGGAGGGACGGCCGCGATCAC
CTGTGGAAGAAAC (SEQ ID NO.: 132)

CDR1:
AACATTGGAAGTGAAACT (SEQ ID NO.: 133)

FR2:
GTGCACTGGTACCAGCAGAAGCCAGGCCAGGCCCCTGTGCTGGTCGTCTAT (SEQ ID NO.: 134)

CDR2:
GATGATGAC

FR3:
GACCGGCCCTCAGGGATCCCTGAGCGATTCTCTGGCTCCAACTCTGGGAACACGGCCACCCT
GACCATCAGCAGGGTCGAGGCCGGGGATGAGGCCGACTATTACTGT (SEQ ID NO.: 135)

CDR3:
CAGGTGTGGGATAGGAGTAATTATCATCAGGTA (SEQ ID NO.: 136)

FR4:
TTCGGCGGAGGGACCAAGTTGACCGTCCTAG (SEQ ID NO.: 137)

RSV-SPECIFIC BINDING MOLECULES AND MEANS FOR PRODUCING THEM

This application is a continuation of U.S. patent application Ser. No. 15/047,306, filed on Feb. 18, 2016, which is a continuation of U.S. patent application Ser. No. 14/026,182, filed Sep. 13, 2013, which is a divisional application of U.S. patent application Ser. No. 12/600,950, which is the § 371 US national phase application of International Patent Application No. PCT/NL2008/050333, filed on May 30, 2008, which claims priority to European Patent Application No. 07109472.6, filed Jun. 1, 2007, each of which is incorporated herein by reference.

SEQUENCE LISTING

This application contains a Sequence Listing electronically submitted to the United States Patent and Trademark Office via EFS-Web as an ASCII text file entitled "490-00010104_SequenceListing_ST25.txt" having a size of 68 kilobytes and created on Jul. 17, 2018. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

The invention relates to the fields of biology and medicine.

Respiratory Syncytial Virus (RSV) is a common cold virus belonging to the family of paramyxovirus. RSV is virulent, easily transmissible and the most common cause of lower respiratory tract disease in children of less than 2 years of age. Up to 98% of children attending day care will be infected in a single RSV season. Between 0.5% and 3.2% of children with RSV infection require hospitalization. Approximately 90,000 hospital admissions and 4500 deaths per year were reported in United States. Major risk factors for hospitalization due to RSV are premature birth, chronic lung disease, congenital heart disease, compromised immunity, and age younger than 6 weeks in otherwise healthy children. No effective treatment of RSV positive bronchiolitis beside supportive care in the form of adequate nutrition and oxygen therapy is available. Antiviral therapies such as Ribavirin have not been proven to be effective in RSV infection. One monoclonal antibody, Palivizumab (also called Synagis), is registered for prophylaxis against RSV infection. Palivizumab is a genetically engineered (humanized) monoclonal antibody to the fusion protein of RSV. However, Palivizumab is not always effective. Therefore, there is a need in the art for alternative antibodies and therapies against RSV.

It is an object of the present invention to provide means and methods for counteracting and/or preventing an RSV-related disease. It is a further object of the invention to provide alternative and/or improved antibodies against RSV, or functional equivalents of such antibodies, and to provide stable cells capable of producing antibodies—or functional equivalents thereof—against RSV.

The present invention provides antibodies and functional equivalents thereof which are capable of specifically binding RSV. Such antibodies and/or functional equivalents, also called herein "anti-RSV antibodies" or "RSV-specific antibodies", are capable of specifically binding at least one component of RSV, such as for instance an epitope of an RSV protein. Non-specific sticking is not encompassed by the term "specifically binding". Anti-RSV antibodies and functional equivalents according to the present invention are particularly suitable for counteracting and/or at least in part preventing an RSV-infection and/or adverse effects of an RSV infection. One particularly preferred anti-RSV antibody according to the present invention is the antibody designated "D25", which has a heavy chain region and a light chain region as depicted in FIGS. 11A-C. The CDR sequences of D25, which in particular contribute to the antigen-binding properties of D25, are depicted in FIGS. 11B and 11C. Antibody D25 appears to have superior characteristics as compared to the registered anti-RSV antibody Palivizumab (FIG. 8). For instance, D25 has an IC50 value of about 0.4-1.5 ng/ml in an in vitro neutralization assay wherein HEp-2 cells are infected with RSV, whereas Palivizumab has an IC50 value of about 453 ng/ml.

A functional equivalent of an antibody is defined herein as a functional part, derivative or analogue of an antibody.

A functional part of an antibody is defined as a part which has at least one same property as said antibody in kind, not necessarily in amount. Said functional part is capable of binding the same antigen as said antibody, albeit not necessarily to the same extent. A functional part of an antibody preferably comprises a single domain antibody, a single chain antibody, a single chain variable fragment (scFv), a Fab fragment or a F(ab')$_2$ fragment.

A functional derivative of an antibody is defined as an antibody which has been altered such that at least one property—preferably an antigen-binding property—of the resulting compound is essentially the same in kind, not necessarily in amount. A derivative is provided in many ways, for instance through conservative amino acid substitution, whereby an amino acid residue is substituted by another residue with generally similar properties (size, hydrophobicity, etc), such that the overall functioning is likely not to be seriously affected.

A person skilled in the art is well able to generate analogous compounds of an antibody. This is for instance done through screening of a peptide library or phage display library. Such an analogue has essentially at least one same property as said antibody in kind, not necessarily in amount.

As is well known by the skilled person, a heavy chain of an antibody is the larger of the two types of chains making up an immunoglobulin molecule. A heavy chain comprise constant domains and a variable domain, which variable domain is involved in antigen binding. A light chain of an antibody is the smaller of the two types of chains making up an immunoglobulin molecule. A light chain comprises a constant domain and a variable domain. The variable domain is, together with the variable domain of the heavy chain, involved in antigen binding.

Complementary-determining regions (CDRs) are the hypervariable regions present in heavy chain variable domains and light chain variable domains. The CDRs of a heavy chain and the connected light chain of an antibody together form the antigen-binding site.

Now that the present invention provides the insight that the CDR sequences depicted in FIG. 11 provide desired RSV-binding characteristics, a skilled person is well capable of generating variants comprising at least one altered CDR sequence. For instance, conservative amino acid substitution is applied. Conservative amino acid substitution involves substitution of one amino acid with another with generally similar properties (size, hydrophobicity, etc), such that the overall functioning is likely not to be seriously affected.

It is also possible to change at least one CDR sequence depicted in FIG. 11 in order to generate a variant antibody, or a functional equivalent thereof with at least one altered property as compared to D25. Preferably, an antibody or functional equivalent is provided comprising a CDR sequence which is at least 70% identical to a CDR sequence as depicted in FIG. 11, so that the favorable binding characteristics of D25 are at least in part maintained or even improved. A CDR sequence as depicted in FIG. 11 is preferably altered such that the resulting antibody or functional equivalent comprises at least one improved property, such as for instance an improved binding affinity, selectivity and/or stability, as compared to D25. Variant antibodies or functional equivalents thereof comprising an amino acid sequence which is at least 70% identical to a CDR sequence as depicted in FIG. 11 are therefore within the scope of the present invention. Various methods are available in the art for altering an amino acid sequence. For instance, a heavy chain or light chain sequence with a desired CDR sequence is artificially synthesized. Preferably, a nucleic acid sequence encoding a CDR sequence is mutated, for instance using random—or site-directed—mutagenesis.

In a first aspect the invention thus provides an isolated, synthetic or recombinant antibody or a functional equivalent thereof which is capable of specifically binding Respiratory Syncytial Virus and which comprises:
- a heavy chain CDR1 sequence comprising a sequence which is at least 70% identical to the sequence NYIIN (SEQ ID NO: 1), and/or
- a heavy chain CDR2 sequence comprising a sequence which is at least 75% identical to the sequence GIIPVLGTVHYAPKFQG (SEQ ID NO: 2), and/or
- a heavy chain CDR3 sequence comprising a sequence which is at least 70% identical to the sequence ETALVVSTTYLPHYFDN (SEQ ID NO: 3), and/or
- a light chain CDR1 sequence comprising a sequence which is at least 85% identical to the sequence QASQDIVNYLN (SEQ ID NO: 4), and/or
- a light chain CDR2 sequence comprising a sequence which is at least 70% identical to the sequence VASNLET (SEQ ID NO: 5).

Preferably, said antibody also comprises a light chain CDR3 sequence comprising a sequence which is at least 70% identical to the sequence QQYDNLP (SEQ ID NO: 6).

Preferably, an antibody or a functional equivalent according to the invention comprises a CDR sequence which is at least 75%, more preferably at least 80%, more preferably at least 85%, more preferably at least 90% identical to at least one of the CDR sequences depicted in FIG. 11A. Most preferably, an antibody or a functional equivalent according to the invention comprises a CDR sequence which is at least 95% identical to at least one of the CDR sequences depicted in FIG. 11A. The particularly preferred antibody D25, described above, comprises CDR sequences which consist of the CDR sequences depicted in FIG. 11A. A particularly preferred embodiment according to the invention thus provides an isolated, synthetic or recombinant antibody or a functional equivalent thereof which is capable of specifically binding Respiratory Syncytial Virus and which comprises:
- a heavy chain CDR1 sequence comprising the sequence NYIIN (SEQ ID NO: 1), and/or
- a heavy chain CDR2 sequence comprising the sequence GIIPVLGTVHYAPKFQG (SEQ ID NO: 2), and/or
- a heavy chain CDR3 sequence comprising the sequence ETALVVSTTYLPHYFDN (SEQ ID NO: 3), and/or
- a light chain CDR1 sequence comprising the sequence QASQDIVNYLN (SEQ ID NO: 4), and/or
- a light chain CDR2 sequence comprising the sequence VASNLET (SEQ ID NO: 5).

Preferably, said antibody also comprises a light chain CDR3 sequence comprising the sequence QQYDNLP (SEQ ID NO: 6).

In one embodiment an antibody or functional equivalent is provided which comprises the three heavy chain CDR sequences and the three light chain CDR sequences as depicted in FIGS. 11B and 11C, or sequences that are at least 70%, preferably at least 80%, more preferably at least 85% identical thereto. Further provided is therefore an isolated, synthetic or recombinant antibody or a functional equivalent thereof which comprises a heavy chain CDR1 sequence comprising a sequence which is at least 70% identical to the sequence NYIIN (SEQ ID NO: 1) and a heavy chain CDR2 sequence comprising a sequence which is at least 70% identical to the sequence GIIPVLGTVHYAPKFQG (SEQ ID NO: 2) and a heavy chain CDR3 sequence comprising a sequence which is at least 70% identical to the sequence ETALVVSITYLPHYFDN (SEQ ID NO: 3) and a light chain CDR1 sequence comprising a sequence which is at least 70% identical to the sequence QASQDIVNYLN (SEQ ID NO: 4) and a light chain CDR2 sequence comprising a sequence which is at least 70% identical to the sequence VASNLET (SEQ ID NO: 5), and a light chain CDR3 sequence comprising a sequence which is at least 70% identical to the sequence QQYDNLP (SEQ ID NO: 6). Said antibody or functional equivalent preferably comprises CDR sequences which are at least 75%, more preferably at least 80%, more preferably at least 85%, more preferably at least 90%, most preferably at least 95% identical to the heavy chain CDR sequences and the light chain CDR sequences as depicted in FIGS. 11B and 11C. An antibody or functional equivalent comprising the above mentioned heavy chain CDR1, CDR2 and CDR3 sequences as well as the above mentioned light chain CDR1, CDR2 and CDR3 sequences is also provided.

Antibodies or functional equivalents thereof comprising a variable heavy chain amino acid sequence which is at least 70% identical to the heavy chain sequence as depicted in FIG. 11 is also provided. Such heavy chain sequences provide desired RSV-binding properties, as evidenced by antibody D25. Further provided is therefore an antibody or a functional equivalent thereof; having a heavy chain sequence comprising a sequence which is at least 70% identical to the sequence QVQLVQSOAEVKKPGSSVMVSCQASGGPLRNYIINWLRQAPGQGPEWMOGII PVLGTVHYAPKFQGRVTITADESTDTAYIHLISLRSEDTAMYYCATETALVVST TYLPHYFDNWGQGTLVTVSS (SEQ ID NO: 7). Moreover, variable light chain amino acid sequences which are at least 70% identical to the light chain sequence as depicted in FIG. 11 also provide desired RSV-binding properties, as evidenced by antibody D25. An antibody, or a functional equivalent thereof having a light chain sequence which is at least 70% identical to the sequence DIQMTQSPSSLSAAVGDRVTITCQASQDIVNYLNWYQQKPGKAPKLLIYVASNLETG VPSRFSGSGSGTDFSLTISSLQPEDVATYYCQQYDNLPLTFGGGTKVEIKRTV (SEQ ID NO: 8) is therefore also provided. An antibody or functional part according to the invention preferably comprises a variable heavy chain sequence and/or a variable light chain sequence which is at least 75%, more preferably at least 80%, more preferably at least 85%, more preferably at least 90%, most preferably at least 95% identical to the heavy chain sequence and/or the light chain sequence as depicted in FIG. 11. The higher the homology, the more closely said antibody or functional part resembles antibody D25. An antibody or functional part according to the invention preferably comprises a heavy chain as well as a light chain which resemble the heavy and light chain of D25. Further provided is therefore an antibody or functional part comprising a heavy chain sequence and a light chain sequence which are at least 70%, more preferably at least 80%, more preferably at least 85%, more preferably at least 90%, most preferably at least 95% identical to the heavy chain sequence and the light chain sequence as depicted in FIG. 11.

One embodiment provides an antibody or functional equivalent thereof comprising a heavy chain sequence consisting of the heavy chain sequence as depicted in FIG. 11, and a light chain sequence consisting of the light chain sequence as depicted in FIG. 11. Alternatively, as is well known by the skilled person, it is possible to generate a shortened heavy chain or light chain sequence while maintaining a binding property of interest. Preferably, such a shortened heavy chain or light chain is generated which has a shorter constant region, as compared to the original heavy or light chain. The variable domain is preferably maintained. For instance, a Fab fragment or F(ab')$_2$ fragment based on a heavy chain sequence or light chain sequence depicted in FIG. 11 is produced. A functional equivalent of an antibody comprising at least a functional part of a sequence as depicted in FIG. 11 is therefore also provided. Said functional part has a length of at least 20 amino acids and comprises a sequence which is at least 70% identical to the heavy chain CDR1 sequence depicted in FIGS. 11B and 11C, and/or a sequence which is at least 75% identical to the heavy chain CDR2 sequence depicted in FIGS. 11B and 11C, and/or a sequence which is at least 70% identical to the heavy chain CDR3 sequence depicted in FIGS. 11B and 11C, and/or a sequence which is at least 85% identical to the light chain CDR1 sequence depicted in FIGS. 11B and 11C, and/or a sequence which is at least 70% identical to the light chain CDR2 sequence depicted in FIGS. 11B and 11C. Preferably, said functional part also comprises a sequence which is at least 70% identical to the light chain CDR3 sequence depicted in FIGS. 11B and 11C.

Another particularly preferred anti-RSV antibody according to the present invention is the antibody designated "AM14", which has a heavy chain region and a light chain region as depicted in FIG. 14A. The CDR sequences of AM14, which in particular contribute to the antigen-binding properties of AM14, are also depicted in FIG. 14A.

Now that the present invention provides the insight that the CDR sequences depicted in FIG. 14C provide desired RSV-binding characteristics, a skilled person is well capable of generating variants comprising at least one altered CDR sequence. For instance, conservative amino acid substitution is applied. Conservative amino acid substitution involves substitution of one amino acid with another with generally similar properties (size, hydrophobicity, etc), such that the overall functioning is likely not to be seriously affected.

It is also possible to change at least one CDR sequence depicted in FIG. 14C in order to generate a variant antibody, or a functional equivalent thereof, with at least one altered property as compared to AM14. Preferably, an antibody or functional equivalent is provided comprising a CDR sequence which is at least 70% identical to a CDR sequence as depicted in FIG. 14C so that the favorable binding characteristics of AM14 are at least in part maintained or even improved. A CDR sequence as depicted in FIG. 14C is preferably altered such that the resulting antibody or functional equivalent comprises at least one improved property, such as for instance an improved binding affinity, selectivity and/or stability, as compared to AM14. Variant antibodies or functional equivalents thereof comprising an amino acid sequence which is at least 70% identical to a CDR sequence as depicted in FIG. 14C are therefore within the scope of the present invention. Various methods are available in the art for altering an amino acid sequence. For instance, a heavy chain or light chain sequence with a desired CDR sequence is artificially synthesized. Preferably, a nucleic acid sequence encoding a CDR sequence is mutated, for instance using random—or site-directed—mutagenesis.

In one aspect the invention thus provides an isolated, synthetic or recombinant antibody or a functional part, derivative and/or analogue thereof which is capable of specifically binding Respiratory Syncytial Virus and which comprises:
- a heavy chain CDR1 sequence comprising a sequence which is at least 70% identical to the sequence GFSFSHYA (SEQ ID NO: 73), and/or
- a heavy chain CDR2 sequence comprising a sequence which is at least 70% identical to the sequence ISYDGENT (SEQ ID NO; 74), and/or
- a heavy chain CDR3 sequence comprising a sequence which is at least 70% identical to the sequence ARDRIVDDYYYYGMDV (SEQ ID NO: 75), and/or
- a light chain CDR1 sequence comprising a sequence which is at least 70% identical to the sequence QDIKKY(SEQ ID NO: 76), and/or
- a light chain CDR2 sequence comprising a sequence which is at least 70% identical to the sequence DAS, and/or
- a light chain CDR3 sequence comprising a sequence which is at least 70% identical to the sequence QQYDNLPPLT (SEQ ID NO: 77).

Preferably, an antibody or a functional equivalent according to the invention comprises a CDR sequence which is at least 75%, more preferably at least 80%, mote preferably at least 85%, more preferably at least 90% identical to at least one of the CDR sequences depicted in FIG. 14C. Most preferably, an antibody or a functional equivalent according to the invention comprises a CDR sequence which is at least 95% identical to at least one of the CDR sequences depicted in FIG. 14C. The particularly preferred antibody AM14, described above, comprises CDR sequences which consist of the CDR sequences depicted in FIG. 14C. A particularly preferred embodiment according to the invention thus provides an isolated, synthetic or recombinant antibody or a functional equivalent thereof which is capable of specifically binding Respiratory Syncytial Virus and which comprises:
- a heavy chain CDR1 sequence comprising the sequence GPSFSHYA (SEQ ID NO: 73), and/or
- a heavy chain CDR2 sequence comprising the sequence ISYDGENT (SEQ ID NO: 74), and/or
- a heavy chain CDR3 sequence comprising the sequence ARDRIVDDYYYYGMDV (SEQ ID NO: 75), and/or
- a light chain CDR1 sequence comprising the sequence QDIKKY (SEQ ID NO: 76), and/or
- a light chain CDR2 sequence comprising the sequence DAS, and/or
- a light chain CDR3 sequence comprising the sequence QQYDNLPPLT (SEQ ID NO: 77).

In one embodiment an antibody or functional equivalent is provided which comprises the three heavy chain CDR sequences and the three light chain CDR sequences as depicted in FIG. 14C, or sequences that are at least 70% identical thereto. Further provided is therefore an isolated, synthetic or recombinant antibody or a functional equivalent thereof which comprises a heavy chain CDR1 sequence comprising a sequence which is at least 70% identical to the sequence GFSFSHYA (SEQ ID NO: 73) and a heavy chain CDR2 sequence comprising a sequence which is at least 70% identical to the sequence ISYDGENT (SEQ ID NO: 74) and a heavy chain CDR3 sequence comprising a sequence which is at least 70% identical to the sequence ARDRIVDDYYYYGMDV (SEQ ID NO: 75) and a light chain CDR1 sequence comprising a sequence which is at least 70% identical to the sequence QDIKKY (SEQ ID NO: 76) and a light chain CDR2 sequence comprising a sequence which is at least 70% identical to the sequence DAS, and a light chain CDR3 sequence comprising a sequence which is at least 70% identical to the sequence QQYDNLPPLT (SEQ ID NO: 77). Said antibody or functional equivalent preferably comprises CDR sequences which are at least 75%, more preferably at least 80%, more preferably at least 85%, more preferably at least 90%, most preferably at least 95% identical to the heavy chain CDR sequences and the light chain CDR sequences as depicted in FIG. 14C. An antibody or functional equivalent comprising the above mentioned heavy chain CDR1, CDR2 and CDR3 sequences of FIG. 14C as well as the above mentioned light chain CDR1, CDR2 and CDR3 sequences of FIG. 14C is also provided.

Antibodies or functional equivalents thereof comprising a heavy chain amino acid sequence which is at least 70% identical to a heavy chain sequence as depicted in FIG. 14A is also provided. Such heavy chain sequences provide desired RSV-binding properties, as evidenced by antibody AM14. Further provided is therefore an antibody or a functional equivalent thereof, having a heavy chain sequence comprising a sequence which is at least 70% identical to the sequence EVQLVESGGGVVQPGRSLRLS-CAASGFSFSHYAMHWVRQAPGKGLEWVAVIS YDGENTYYADSVKGRFSISRDNSKNTVSLQMNSL-RPEDTALYYCARDRIVDD YYYYGMDVWGQGATVT-VSS (SEQ ID NO: 78). Moreover, light chain amino acid sequences which are at least 70% identical to a light chain sequence as depicted in FIG. 14A also provide desired RSV-binding properties, as evidenced by antibody AM14. An antibody, or a functional equivalent thereof having a light chain sequence which is at least 70% identical to the sequence DIQMTQSPSSLSASVGDRVTITCQASQDIK-KYLNWYHQKPGKVPLLMHDASNLETG VPSRF-SORGSGTDFTLTISSLQPEDIGTYYCQQYDNLPPLT-FOGGTKVEIKRTV (SEQ ID NO: 79) is therefore also provided. An antibody or functional part according to the invention preferably comprises a variable heavy chain sequence and/or a variable light chain sequence which is at least 75%, more preferably at least 80%, more preferably at least 85%, more preferably at least 90%, most preferably at least 95% identical to a heavy chain sequence and/or a light chain sequence as depicted in FIG. 14A. The higher the homology, the more closely said antibody or functional part resembles antibody AM14. An antibody or functional part according to the invention preferably comprises a heavy chain as well as a light chain which resemble the heavy and light chain of AM14. Further provided is therefore an antibody or functional part comprising a heavy chain sequence and a light chain sequence which are at least 70%, more preferably at least 80%, more preferably at least 85%, more preferably at least 90%, most preferably at least 95% identical to the heavy chain sequence and the light chain sequence as depicted in FIG. 14A.

One embodiment provides an antibody or functional equivalent thereof comprising a heavy chain sequence consisting of the heavy chain sequence as depicted in FIG. 14A, and a light chain sequence consisting of the light chain sequence as depicted in FIG. 14A. Alternatively, as is well known by the skilled person, it is possible to generate a shortened heavy chain or light chain sequence while maintaining a binding property of interest. Preferably, such a shortened heavy chain or light chain is generated which has a shorter constant region, as compared to the original heavy or light chain. The variable domain is preferably maintained. For instance, a Fab fragment or F(ab')$_2$ fragment based on a heavy chain sequence or light chain sequence depicted in FIG. 14A is produced. A functional equivalent of an antibody comprising at least a functional part of a sequence as depicted in FIG. 14A is therefore also provided. Said functional part has a length of at least 20 amino acids and comprises a sequence which is at least 70% identical to at least one of the CDR sequences depicted in FIG. 14A.

Another particularly preferred anti-RSV antibody according to the present invention is the antibody designated "AM16", which has a heavy chain region and a light chain region as depicted in FIG. 14E. The CDR sequences of AM16, which in particular contribute to the antigen-binding properties of AM16, are also depicted in FIG. 14G.

Now that the present invention provides the insight that the CDR sequences depicted in FIG. 14G provide desired RSV-binding characteristics, a skilled person is well capable of generating variants comprising at least one altered CDR sequence. For instance, conservative amino acid substitution is applied. Conservative amino acid substitution involves substitution of one amino acid with another with generally similar properties (size, hydrophobicity, etc), such that the overall functioning is likely not to be seriously affected.

It is also possible to change at least one CDR sequence depicted in FIG. 14G in order to generate a variant antibody, or a functional equivalent thereof, with at least one altered property as compared to AM16. Preferably, an antibody or functional equivalent is provided comprising a CDR sequence which is at least 70% identical to a CDR sequence as depicted in FIG. 14G, so that the favorable binding characteristics of AM16 are at least in part maintained or even improved. A CDR sequence as depicted in FIG. 14G is preferably altered such that the resulting antibody or functional equivalent comprises at least one improved property, such as for instance an improved binding affinity, selectivity and/or stability, as compared to AM16. Variant antibodies or functional equivalents thereof comprising an amino acid sequence which is at least 70% identical to a CDR sequence as depicted in FIG. 14G are therefore within the scope of the present invention. Various methods are available in the art for altering an amino acid sequence. For instance, a heavy chain or light chain sequence with a desired CDR sequence is artificially synthesized. Preferably, a nucleic acid sequence encoding a CDR sequence is mutated, for instance using random—or site-directed-mutagenesis.

In one aspect the invention thus provides an isolated, synthetic or recombinant antibody or a functional part, derivative and/or analogue thereof which is capable of specifically binding Respiratory Syncytial Virus and which comprises:
a heavy chain CDR1 sequence comprising a sequence which is at least 70% identical to the sequence GFTF-SSYN (SEQ ID NO: 80), and/or
a heavy chain CDR2 sequence comprising a sequence which is at least 70% identical to the sequence ISAGSSYI (SEQ ID NO: 81), and/or
a heavy chain CDR3 sequence comprising a sequence which is at least 70% identical to the sequence AREDYGPGNYYSPNWFDP (SEQ ID NO: 82), and/or
a light chain CDR1 sequence comprising a sequence which is at least 70% identical to the sequence SSNI-GAGYD (SEQ ID NO: 83), and/or a light chain CDR2 sequence comprising a sequence which is at least 70% identical to the sequence GNT, and/or a light chain CDR3 sequence comprising a sequence which is at least 70% identical to the sequence HSY-DRSLSG (SEQ ID NO: 84).

Preferably, an antibody or a functional equivalent according to the invention comprises a CDR sequence which is at least 75%, more preferably at least 80%, more preferably at least 85%, more preferably at least 90% identical to at least one of the CDR sequences depicted in FIG. 14G. Most preferably, an antibody or a functional equivalent according to the invention comprises a CDR sequence which is at least 95% identical to at least one of the CDR sequences depicted in FIG. 14G. The particularly preferred antibody AM16, described above, comprises CDR sequences which consist of the CDR sequences depicted in FIG. 14G. A particularly preferred embodiment according to the invention thus provides an isolated, synthetic or recombinant antibody or a functional equivalent thereof which is capable of specifically binding Respiratory Syncytial Virus and which comprises:

a heavy chain CDR1 sequence comprising the sequence GFTFSSYN (SEQ ID NO: 80), and/or a heavy chain CDR2 sequence comprising the sequence ISAGSSYI (SEQ ID NO: 81), and/or a heavy chain CDR3 sequence comprising the sequence AREDYGPGNYYSPNWFDP (SEQ ID NO: 82), and/or a light chain CDR1 sequence comprising the sequence SSNIGAGYD (SEQ ID NO: 83), and/or a light chain CDR2 sequence comprising the sequence GNT, and/or a light chain CDR3 sequence comprising the sequence HSYDRSLSG (SEQ ID NO: 84).

In one embodiment an antibody or functional equivalent is provided which comprises the three heavy chain CDR sequences and the three light chain CDR sequences as depicted in FIG. 14G, or sequences that are at least 70% identical thereto. Further provided is therefore an isolated, synthetic or recombinant antibody or a functional equivalent thereof which comprises a heavy chain CDR1 sequence comprising a sequence which is at least 70% identical to the sequence GFTFSSYN (SEQ ID NO: 80) and a heavy chain CDR2 sequence comprising a sequence which is at least 70% identical to the sequence ISAGSSYI (SEQ ID NO: 81) and a heavy chain CDR3 sequence comprising a sequence which is at least 70% identical to the sequence AREDYG-PGNYYSPNWFDP (SEQ ID NO: 82) and a light chain CDR1 sequence comprising a sequence which is at least 70% identical to the sequence SSNIGAGYD (SEQ ID NO: 83) and a light chain CDR2 sequence comprising a sequence which is at least 70% identical to the sequence GNT, and a light chain CDR3 sequence comprising a sequence which is at least 70% identical to the sequence HSYDRSLSG (SEQ ID NO: 84). Said antibody or functional equivalent preferably comprises CDR sequences which are at least 75%, more preferably at least 80%, more preferably at least 85%, more preferably at least 90%, most preferably at least 95% identical to the above mentioned heavy chain CDR sequences and the above mentioned light chain CDR sequences as depicted in FIG. 14G. An antibody or functional equivalent comprising the above mentioned heavy chain CDR1, CDR2 and CDR3 sequences of FIG. 14G as well as the above mentioned light chain CDR1, CDR2 and CDR3 sequences of FIG. 14G is also provided.

Antibodies or functional equivalents thereof comprising a heavy chain amino acid sequence which is at least 70% identical to a heavy chain sequence as depicted in FIG. 14E is also provided. Such heavy chain sequences provide desired RSV-binding properties, as evidenced by antibody AM16. Further provided is therefore an antibody or a functional equivalent thereof, having a heavy chain sequence comprising a sequence which is at least 70% identical to the sequence EVQLVETQGGLAQPGOSLRLS-CAASGFTFSSYNMNWVRQAPGKGLEWVSHISAGSS YIYYSDSVKGRFTVSRDNVRNSVYLQMNSLRAAD-TAVYYCAREDYGPGNYYSPNW FDPWGQGTLVTVSS (SEQ ID NO: 85). Moreover, light chain amino acid sequences which are at least 70% identical to a light chain sequence as depicted in FIG. 14E also provide desired RSV-binding properties, as evidenced by antibody AM16. An antibody, or a functional equivalent thereof having a light chain sequence which is at least 70% identical to the sequence QSVVTQPPSVSGAPGQRVTISCTGSSSNI-GAGYDVHWYQQLPGTAPKLLIYGNTNRPS GVSDRF-SGSKSGTSASLAITGLQAEDEADYYCHSYDRSLSGS-VFGGGTKLTV (SEQ ID NO: 86) is therefore also provided. An antibody or functional part according to the invention preferably comprises a variable heavy chain sequence and/or a variable light chain sequence which is at least 75%, more preferably at least 80%, more preferably at least 85%, more preferably at least 90%, most preferably at least 95% identical to the heavy chain Sequence and/or the light chain sequence as depicted in FIG. 14E. The higher the homology, the more closely said antibody or functional part resembles antibody AM16. An antibody or functional part according to the invention preferably comprises a heavy chain as well as a light chain which resemble the heavy and light chain of AM16. Further provided is therefore an antibody or functional part comprising a heavy chain sequence and a light chain sequence which are at least 70%, more preferably at least 80%, more preferably at least 85%, more preferably at least 90%, most preferably at least 95% identical to the heavy chain sequence and the light chain sequence as depicted in FIG. 14E.

One embodiment provides an antibody or functional equivalent thereof comprising a heavy chain sequence consisting of the heavy chain sequence as depicted in FIG. 14E, and a light chain sequence consisting of the light chain sequence as depicted in FIG. 14E. Alternatively, as is well known by the skilled person, it is possible to generate a shortened heavy chain or light chain sequence while maintaining a binding property of interest. Preferably, such a shortened heavy chain or light chain is generated which has a shorter constant region, as compared to the original heavy or light chain. The variable domain is preferably maintained. For instance, a Fab fragment or F(ab')$_2$ fragment based on a heavy chain sequence or light chain sequence depicted in FIG. 14B is produced. A functional equivalent of an antibody comprising at least a functional part of a sequence as depicted in FIG. 14E is therefore also provided. Said functional part has a length of at least 20 amino acids and comprises a sequence which is at least 70% identical to at least one of the CDR sequences depicted in FIG. 14G.

Another particularly preferred anti-RSV antibody according to the present invention is the antibody designated "AM23", which has a heavy chain region and a light chain region as depicted in FIG. 14I. The CDR sequences of AM23, which in particular contribute to the antigen-binding properties of AM23, are also depicted in FIG. 14K.

Now that the present invention provides the insight that the CDR sequences depicted in FIG. 14K provide desired RSV-binding characteristics, a skilled person is well capable of generating variants comprising at least one altered CDR sequence. For instance, conservative amino acid substitution is applied. Conservative amino acid substitution involves substitution of one amino acid with another with generally similar properties (size, hydrophobicity, etc), such that the overall functioning is likely not to be seriously affected.

It is also possible to change at least one CDR sequence depicted in FIG. 14K in order to generate a variant antibody, or a functional equivalent thereof, with at least one altered property as compared to AM23. Preferably, an antibody or functional equivalent is provided comprising a CDR sequence which is at least 70% identical to a CDR sequence as depicted in FIG. 14K, so that the favorable binding characteristics of AM23 are at least in part maintained or even improved. A CDR sequence as depicted in FIG. 14K is preferably altered such that the resulting antibody or functional equivalent comprises at least one improved property, such as for instance an improved binding affinity, selectivity and/or stability, as compared to AM23. Variant antibodies or functional equivalents thereof comprising an amino acid sequence which is at least 70% identical to a CDR sequence as depicted in FIG. 14K are therefore within the scope of the present invention. Various methods are available in the art for altering an amino acid sequence. For instance, a heavy chain or light chain sequence with a desired CDR sequence is artificially synthesized. Preferably, a nucleic acid sequence encoding a CDR sequence is mutated, for instance using random—or site-directed—mutagenesis.

In one aspect the invention thus provides an isolated, synthetic or recombinant antibody or a functional part, derivative and/or analogue thereof which is capable of specifically binding Respiratory Syncytial Virus and which comprises:
  a heavy chain CDR1 sequence comprising a sequence which is at least 70% identical to the sequence GFNFHNYG (SEQ ID NO: 87), and/or
  a heavy chain CDR2 sequence comprising a sequence which is at least 70% identical to the sequence VWYDGSKK (SEQ ID NO: 88), and/or
  a heavy chain CDR3 sequence comprising a sequence which is at least 70% identical to the sequence VRDKVGPTPYFDS (SEQ ID NO: 89), and/or
  a light chain CDR1 sequence comprising a sequence which is at least 70% identical to the sequence NIGSET (SEQ ID NO: 90), and/or
  a light chain CDR2 sequence comprising a sequence which is at least 70% identical to the sequence DDD, and/or
  a light chain CDR3 sequence comprising a sequence which is at least 70% identical to the sequence QVWDRSNYHQV (SEQ ID NO: 91).

Preferably, an antibody or a functional equivalent according to the invention comprises a CDR sequence which is at least 75%, more preferably at least 80%, more preferably at least 85%, mote preferably at least 90% identical to at least one of the CDR sequences depicted in FIG. 14C. Most preferably, an antibody or a functional equivalent according to the invention comprises a CDR sequence which is at least 95% identical to at least one of the CDR sequences depicted in FIG. 14C. The particularly preferred antibody AM23, described above, comprises CDR sequences which consist of the CDR sequences depicted in FIG. 14C. A particularly preferred embodiment according to the invention thus provides an isolated, synthetic or recombinant antibody or a functional equivalent thereof which is capable of specifically binding Respiratory Syncytial Virus and which comprises:
  a heavy chain CDR1 sequence comprising the sequence GFNFHNYG (SEQ ID NO: 87), and/or
  a heavy chain CDR2 sequence comprising the sequence VWYDGSKK (SEQ ID NO: 88), and/or
  a heavy chain CDR3 sequence comprising the sequence VRDKVGPTPYFDS (SEQ ID NO: 89), and/or
  a light chain CDR1 sequence comprising the sequence NIGSET (SEQ ID NO: 90), and/or
  a light chain CDR2 sequence comprising the sequence DDD, and/or
  a light chain CDR3 sequence comprising the sequence QVWDRSNYHQV (SEQ ID NO: 91).

In one embodiment an antibody or functional equivalent is provided which comprises the three heavy chain CDR sequences and the three light chain CDR sequences as depicted in FIG. 14K, or sequences that are at least 70% identical thereto. Further provided is therefore an isolated, synthetic or recombinant antibody or a functional equivalent thereof which comprises a heavy chain CDR1 sequence comprising a sequence which is at least 70% identical to the sequence GFNFHNYG (SEQ ID NO: 87) and a heavy chain CDR2 sequence comprising a sequence which is at least 70% identical to the sequence VWYDQSKK (SEQ ID NO: 88) and a heavy chain CDR3 sequence comprising a sequence which is at least 70% identical to the sequence VRDKVGPTPYFDS (SEQ ID NO: 89) and a light chain CDR1 sequence comprising a sequence which is at least 70% identical to the sequence NIGSET (SEQ ID NO: 90) and a light chain CDR2 sequence comprising a sequence which is at least 70% identical to the sequence DDD, and a light chain CDR3 sequence comprising a sequence which is at least 70% identical to the sequence QVWDRSNYHQV (SEQ ID NO: 91). Said antibody or functional equivalent preferably comprises CDR sequences which are at least 75%, more preferably at least 80%, more preferably at least 85%, more preferably at least 90%, most preferably at least 95% identical to the above mentioned heavy chain CDR sequences and the above mentioned light chain CDR sequences as depicted in FIG. 14K. An antibody or functional equivalent comprising the above mentioned heavy chain CDR1, CDR2 and CDR3 sequences of FIG. 14K as well as the above mentioned light chain CDR1, CDR2 and CDR3 sequences of FIG. 14K is also provided.

Antibodies or functional equivalents thereof comprising a heavy chain amino acid sequence which is at least 70% identical to a heavy chain sequence as depicted in FIG. 14I is also provided. Such heavy chain sequences provide desired RSV-binding properties, as evidenced by antibody AM23. Further provided is therefore an antibody or a functional equivalent thereof, having a heavy chain sequence comprising a sequence which is at least 70% identical to the sequence EVQLVESGGNVVKPGTSLRLSCAATGFNFHNYGMNWVRQAPGKGLEWVAVVWYDOSKKYYADSVTORFAISRDNSKNTLYLQMNSLRVEDTAVYYCVRDKVGPTPYFDSW GQGTLVTVSS (SEQ ID NO: 92). Moreover, light chain amino acid sequences which are at least 70% identical to a light chain sequence as depicted in FIG. 14I also provide desired RSV-binding properties, as evidenced by antibody AM23. An antibody, or a functional equivalent thereof having a light chain sequence which is at least 70% identical to the sequence SYVLTQPPSVSLAPGGTAAITCGRNNIGSETVHWYQQKPGQAPVLWYDDDDRPSGIP ERFSGSNSGNTATLTISRVEAGDEADYYCQVWDRSNYHQVFGGGTKLTV (SEQ ID NO: 93) is therefore also provided. An antibody or functional part according to the invention preferably comprises a variable heavy chain sequence and/or a variable light chain sequence which is at least 75%, more preferably at least 80%, more preferably at least 85%, more preferably at least 90%, most preferably at least 95% identical to the heavy chain sequence and/or the light chain sequence as depicted in FIG. 14I. The higher the homology, the more closely said antibody or functional part resembles antibody AM23. An antibody or functional part according to the invention preferably comprises a heavy chain as well as a light chain which resemble the heavy and light chain of AM23. Further provided is therefore an antibody or functional part comprising a heavy chain sequence and a light chain sequence which are at least 70%, more preferably at least 80%, more preferably at least 85%, more preferably at least 90%, most preferably at least 95% identical to the heavy chain sequence and the light chain sequence as depicted in FIG. 14I.

One embodiment provides an antibody or functional equivalent thereof comprising a heavy chain sequence consisting of the heavy chain sequence as depicted in FIG. 14I, and a light chain sequence consisting of the light chain sequence as depicted in FIG. 14I. Alternatively, as is well known by the skilled person, it is possible to generate a shortened heavy chain or light chain sequence while maintaining a binding property of interest. Preferably, such a shortened heavy chain or light chain is generated which has a shorter constant region, as compared to the original heavy or light chain. The variable domain is preferably maintained. For instance, a Fab fragment or F(ab')$_2$ fragment based on a heavy chain sequence or light chain sequence depicted in FIG. 14I is produced. A functional equivalent of an antibody comprising at least a functional part of a sequence as depicted in FIG. 14I is therefore also provided. Said functional part has a length of at least 20 amino acids and comprises a sequence which is at least 70% identical to at least one of the CDR sequences depicted in FIG. 14K.

The present invention provides RSV-specific antibodies or functional equivalents thereof having improved properties as compared to prior art antibodies. The inventors have succeeded in generating RSV-specific antibodies with low IC$_{50}$ values. Such antibodies have a particular high or strong affinity for RSV and are therefore particularly suitable for counteracting and/or at least in part preventing an RSV-infection and/or adverse effects of an RSV infection. One embodiment provides an antibody which has an IC$_{50}$ value of less than 10 ng/ml in an in vitro neutralization assay wherein HEp-2 cells are infected with RSV, and a functional equivalent of said antibody. Said antibody or functional equivalent preferably has an IC$_{50}$ value of less than 5 ng/ml, more preferably less than 2 ng/ml. The preferred antibody D25 has an IC$_{50}$ value of about 0.5-1.5 ng/ml in the in vitro neutralization assay described in the examples (see FIG. 8).

An antibody according to the invention is preferably a human antibody. The use of human antibodies for human therapy diminishes the chance of side-effects due to an immunological reaction in a human individual against non-human sequences. In another preferred embodiment an antibody or functional part, derivative or analogue according to the invention is a chimeric antibody. This way, sequences of interest, such as for instance a binding site of interest, can be included into an antibody or functional equivalent according to the invention.

The invention further provides an isolated, synthetic or recombinant nucleic acid sequence, or a functional part, derivative or analogue thereof encoding an antibody or functional equivalent according to the invention. Such nucleic acid is for instance isolated from a B-cell which is capable of producing an antibody according to the invention, as outlined in more detail below. A preferred embodiment provides a nucleic acid sequence comprising a sequence which is at least 70% homologous to at least a functional part of a nucleic acid sequence as depicted in FIGS. 11A-11C, FIG. 12, and/or FIGS. 14A-14L. Said nucleic acid sequence preferably comprises a sequence which is at least 75%, more preferably at least 80%, more preferably at least 85%, more preferably at least 90%, most preferably at least 95% homologous to at least a functional part of a nucleic acid sequence as depicted in FIGS. 11A-11C, FIG. 12, and/or FIGS. 14A-14L. Said functional part has a length of at least 30 nucleotides, preferably at least 50 nucleotides, more preferably at least 75 nucleotides. Preferably, said functional part encodes at least one nucleic acid sequence as depicted in FIGS. 11A-11C, FIG. 12, and/or FIGS. 14A-14L. Said sequence is preferably a CDR sequence.

An antibody or functional equivalent according to the invention is particularly suitable for use as a medicine or prophylactic agent. An antibody according to the invention, or a functional part, derivative or analogue thereof, for use as a medicament and/or prophylactic agent is therefore also herewith provided. In a particularly preferred embodiment said antibody comprises antibody D25, AM14, AM16 and/or AM23, or a functional part, derivative or analogue thereof. Said medicament or prophylactic agent is preferably used for counteracting or at least in part preventing an RSV-infection or for counteracting or at least in part preventing adverse effects of an RSV-infection. A use of an antibody, functional part, derivative or analogue according to the invention for the preparation of a medicament and/or prophylactic agent for at least in part treating and/or preventing a RSV-related disorder is therefore also provided, as well as a method for at least in part treating or preventing an RSV-related disorder, the method comprising administering to an individual in need thereof a therapeutically effective amount of an antibody or functional equivalent according to the invention. Said antibody preferably comprises antibody D25, AM14, AM16 and/or AM23, or a functional part, derivative or analogue thereof.

In order to counteract RSV, an antibody or functional equivalent according to the invention is preferably administered to an individual before an RSV-infection has taken place. Alternatively, an antibody or functional equivalent according to the invention is administered when an individual is already infected by RSV. Said antibody or functional equivalent is preferably administered to individuals with an increased risk of RSV-related disorders, such as for instance children with premature birth, individuals with chronic lung disease, congenital heart disease and/or compromised immunity, and children with an age younger than 6 weeks. Also elderly people have an increased risk of RSV-related disorders. Antibodies or functional equivalents according to the invention are preferably administered orally or via one or more injections. Dose ranges of antibodies and/or functional equivalents according to the invention to be used in the therapeutic applications as described herein before are designed on the basis of rising dose studies in the clinic in clinical trials for which rigorous protocol requirements exist. Typical doses are between 0.1 and 10 mg per kg body weight. For therapeutic application, antibodies or functional equivalents according to the invention are typically combined with a pharmaceutically acceptable carrier, adjuvant, diluent and/or excipient. Examples of suitable carriers for instance comprise keyhole limpet haemocyanin (KLH), serum albumin (e.g. BSA or RSA) and ovalbumin. Many suitable adjuvants, oil-based and water-based, are known to a person skilled in the art. In one embodiment said adjuvant comprises Specol. In another embodiment, said suitable carrier comprises a solution like for example saline.

In yet another embodiment a nucleic acid encoding an antibody or functional part according to the invention is used. Upon administration of such nucleic acid, antibodies or functional equivalents are produced by the host's machinery. Produced antibodies or functional equivalents are capable of preventing and/or counteracting RSV-infection and/or the adverse effects of an RSV-infection. A nucleic acid sequence, functional part, derivative and/or analogue according to the invention for use as a medicament and/or prophylactic agent is therefore also herewith provided. Said nucleic acid is preferably used for counteracting RSV. Further provided is therefore a use of a nucleic acid sequence, functional part, derivative and/or analogue according to the invention for the preparation of a medicament and/or prophylactic agent for at least in part treating and/or preventing a RSV-related disorder.

By at least a functional part of a nucleic acid of the invention is meant a part of said nucleic acid, at least 30 base pairs long, preferably at least 50 base pairs long, more preferably at least 100 base pairs long, comprising at least one expression characteristic (in kind not necessarily in amount) as a nucleic acid of the invention. Said functional part at least encodes an amino acid sequence comprising a sequence which is at least 70% identical to a CDR sequence as depicted in FIGS. 11A-11C, FIG. 12, and/or FIGS. 14A-14L.

The invention furthermore provides an isolated antibody producing cell capable of producing an antibody, functional part, derivative or analogue according to the invention. Possible (but not limiting) ways of obtaining such antibody producing cells are outlined in detail in the examples. The inventors have developed and used a new method in order to improve the stability of RSV-specific antibody producing cells. Using this method, RSV-specific antibody producing cells are generated which are stable for at least six months. An RSV-specific antibody producing cell according to the invention, which is stable for at least nine weeks, preferably for at least three months, more preferably for at least six months is therefore also herewith provided.

The present inventors have used their insight that the stability of an RSV-specific antibody producing cell is influenced by influencing the amount of BCL6 and/or Blimp-1 expression product within said antibody producing cell. The amount of BCL6 and/or Blimp-1 expression product is either directly or indirectly influenced. Preferably the amounts of both BCL6 and Blimp-1 expression products within said antibody producing cell are regulated, since both expression products are involved in the stability of an antibody producing cell. The stability of an antibody producing cell is defined as the capability of said antibody producing cell to remain in a certain developmental stage (preferably after said cell has been brought into said stage). Different developmental stages of a cell involve at least one different characteristic of said cell. For instance, a memory B cell is known to differentiate upon stimulation into an antibody-secreting plasma cell via a stage which some researchers call a plasmablast. A memory B cell, a plasmablast and a plasma cell are different developmental stages of a B cell, wherein the B cell has different characteristics. A memory B cell exhibits low proliferation and antibody secretion. A plasmablast exhibits both higher proliferation and higher antibody secretion levels as compared to a memory B cell, whereas a plasma cell secretes high antibody levels but is not capable of proliferating. With a method of the present inventors it has become possible to regulate the replicative life span of an antibody producing cell. A replicative life span of an antibody producing cell is defined herein as the time span wherein a B cell and its progeny cells are capable of replicating while maintaining their capability of producing antibody and/or developing into a cell that produces antibody. Preferably the replicative life span of an antibody producing cell is prolonged, meaning that said antibody producing cell will not terminally differentiate—or only after a longer period as compared to the same kind of antibody producing cells that are currently used—and continue to proliferate in vitro. According to the inventors it is possible to regulate the amount of BCL6 and/or Blimp-1 expression product in an antibody producing cell to such extent that the antibody producing cell is brought into, and/or kept in, a predetermined developmental state in which the cells continue to proliferate. With a method of the inventors it has therefore become possible to increase the replicative life span of an antibody producing cell since it is possible to maintain a B cell in a certain developmental stage wherein replication occurs. Reference is made to PCT/NL2006/000625, filed by the same applicant. The present invention provides means and methods for producing stable RSV-specific antibody producing cells.

An antibody producing cell is defined as a cell which cell is capable of producing and/or secreting antibody or a functional equivalent thereof, and/or which cell is capable of developing into a cell which is capable of producing and/or secreting antibody or a functional equivalent thereof. An RSV-specific antibody producing cell is defined herein as a cell capable of producing and/or secreting antibodies or functional equivalents thereof which are capable of specifically binding RSV and/or a component of RSV, such as for instance an epitope of the RSV F (fusion) protein, the RSV G (attachment) protein or RSV SH (small hydrophobic) protein. Preferably, said RSV-specific antibody producing cell comprises a B cell and/or a B cell-derived plasma cell. A B cell is called herein an antibody producing cell, even when the B cell is in a stage wherein antibody production is low or not present at all, such as a naïve B cell or a memory B cell, being activated or not, because such cells are capable of developing into cells that produce antibody, such as a plasmablast and/or plasma cell.

An RSV-specific antibody producing cell according to the invention preferably comprises a mammalian cell. Non-limiting examples include antibody producing cells derived from a human individual, rodent, rabbit, llama, pig, cow, goat, horse, ape, gorilla. Preferably, said antibody producing cell comprises a human cell, a murine cell, a rabbit cell and/or a llama cell.

BCL6 encodes a transcriptional repressor which is required for normal B cell and T cell development and maturation and which is required for the formation of germinal centers. (Ye, 1997). BCL6 is highly expressed in germinal center B cells whereas it is hardly expressed in plasma cells. BCL6 inhibits differentiation of activated B cells into plasma cells. The transcriptional repressor B lymphocyte induced maturation protein-1 (Blimp-1) is required for development of a B cell into a plasma cell. The human variant of Blimp-1 is named Prdm1. As used herein, any reference to Blimp-1 includes a reference to Prdm1. Blimp-1 drives plasma cell differentiation. BCL6 and Blimp-1 repress expression of the other; thus in a natural situation when one reaches an higher expression level than the other, the stage of differentiation is enforced. In the human body, differentiation of plasma cells from activated naïve or memory B cells involves downregulation of BCL6 and upregulation of Blimp-1. In germinal center cells BCL6 expression is high and Blimp-1 expression is low. In resting memory cells expression of BCL6 and Blimp-1 are low.

Signals that trigger differentiation cause an upregulation of Blimp-1, and this Blimp-1 counteracts the expression of BCL6. The stage where both BCL6 and Blimp-1 are expressed is short-lived and is called a plasmablast. With progressively increasing Blimp-1 levels, BCL6 expression is extinguished, resulting in a plasma cell.

In one embodiment of the present invention, an RSV-specific antibody producing cell is provided wherein BCL6 and Blimp-1 are co-expressed (meaning that both BCL6 and Blimp-1 are expressed in said antibody producing cell for at least 1 day, preferably at least one week, more preferably at least six weeks, most preferably at least three months. Said RSV-specific antibody producing cell is capable of proliferating when an appropriate signal is provided. It has been found that co-expression of BCL6 and Blimp-1 results in an antibody producing cell which is capable of both proliferating and producing antibody. BCL6 and Blimp-1 are preferably co-expressed in a B cell, preferably a human B cell. Co-expression of BCL6 and Blimp-1 in a B cell results in stabilization of said B cell in a plasmablast-like stage. Plasmablasts, like plasma cells, are capable of secreting antibody. However, plasmablasts are still capable of proliferating, whereas plasma cells have lost their capability of proliferating. Plasma cells are therefore unsuitable for culturing antibody-producing cell lines.

One preferred embodiment provides an RSV-specific antibody producing cell comprising an exogenous nucleic acid sequence encoding BCL6 or a functional part, derivative and/or analogue thereof. An exogenous nucleic acid is defined herein as a nucleic acid sequence which does not naturally belong to the genome of a cell. With such exogenous nucleic acid molecule it is possible to regulate a BCL6 concentration in an antibody producing cell independently from expression of endogenous BCL6. Hence, even if expression of endogenous BCL6 is low or absent, for instance caused by Blimp-1, an exogenous nucleic acid sequence encoding BCL6 or a functional part, derivative and/or analogue thereof is still capable of producing a concentration of BCL6 which is sufficient for influencing the stability of an antibody producing cell. Preferably, said nucleic acid sequence encoding BCL6 or a functional part, derivative and/or analogue thereof is constitutively active, so that BCL6 expression is maintained even when endogenous BCL6 expression of said cell is inhibited by an endogenous repressor such as Blimp-1. Most preferably, expression of said nucleic acid sequence encoding BCL6 or a functional part, derivative and/or analogue thereof is regulated by an exogenous inducer of repressor, so that the extent of BCL6 expression is regulated at will.

Preferably, as outlined below in more detail, an RSV-specific antibody producing cell according to the invention comprises an exogenous nucleic acid sequence encoding Bcl-xL or a functional part, derivative and/or analogue thereof. If Bcl-xL or a functional part, derivative and/or analogue thereof is present, it is possible to grow plasmablasts under conditions of low cell density. Expression of said nucleic acid sequence encoding Bcl-xL or a functional part, derivative and/or analogue thereof is preferably regulated by an exogenous inducer of repressor, so that the extent of Bcl-xL expression is regulated at will. A preferred embodiment therefore provides an RSV-specific antibody producing cell comprising:
an exogenous nucleic acid sequence encoding BCL6 or a functional part, derivative and/or analogue thereof and/or
an exogenous nucleic acid sequence encoding Bcl-xL or a functional part, derivative and/or analogue thereof.

Said RSV-specific antibody producing cell preferably comprises both an exogenous nucleic acid sequence encoding BCL6- or a functional part, derivative and/or analogue thereof- and an exogenous nucleic acid sequence encoding Bcl-xL—or a functional part, derivative and/or analogue thereof. Preferably, expression of said nucleic acid sequence encoding BCL6, Bcl-xL or a functional part, derivative and/or analogue of BCL6 or Bcl-xL is regulated by an activator and/or repressor that is inducible by an exogenous compound. For instance, an inducible promoter system is used such as a Tet-on or Tet-off system.

A stable RSV-specific antibody producing cell according to the invention is preferably generated by co-expressing BCL6 and Blimp-1 in an RSV-specific antibody producing cell. An RSV-specific antibody producing cell is preferably obtained from an individual who has been exposed to RSV. Methods for isolating antibody producing cells are well known in the art. For instance, RSV-derived compounds that are marked with a label and/or tag are incubated with a sample of an individual who has been exposed to RSV, which sample comprises antibody producing cells. RSV-specific antibody producing cells that recognize the tagged RSV-derived compounds are isolated while unbound cells are washed away. The resulting RSV-specific antibody producing cells are subsequently stabilized by co-expressing BCL6 as well as Blimp-1.

One embodiment involves first stabilizing total antibody-producing cells from an RSV exposed donor and then isolating cells that recognize the tagged RSV-derived compound. In another embodiment antibody producing cells are equipped with a (fluorescent) marker downstream their B cell receptor (BCR, membrane expressed form of the antibody) that signals when the antibody producing cell binds an un-tagged/unlabeled antigen via the BCR. Antibody producing cells in which the marker is turn are selected and are subsequently stabilized by co-expressing BCL6 as well as Blimp-1. In another embodiment, when there are no antigen-derived compounds available but when there are assays available to screen for unique antibodies, total/bulk antibody producing cells are stabilized by co-expressing BCL6 as well as Blimp-1 and, optionally, also Bcl-XL. According to this embodiment, cells are cultured at low densities, preferably between 10 and 100 cells per 96-well, in the presence of L-cells (mini bulk cultures, MBC). Culture supernatants can be used directly in screenings assays, like ELISA, Western blot or functional assays like ELISPOT, neutralization assays or cell migration assays.

In one embodiment MBC are selected and, to obtain monoclonal cell lines of the antibody producing cell of interest, limiting dilution cultures are preformed and, preferably 2-3 weeks later, supernatants of those cultures are screened again in the preferred assay.

As is well known by the skilled person, many alternative methods are available in the art. The above mentioned embodiments are non-limiting.

Further provided is therefore a method for producing an antibody producing cell, which is stable for at least three months and which is capable of producing RSV-specific antibodies or functional equivalents thereof, the method comprising:
increasing an expression level of Blimp-1 in a cell which is capable of producing RSV-specific antibodies or functional equivalents thereof, and
increasing and/or maintaining a BCL6 expression level in said cell.

With a method according to the invention it has become possible to convert an RSV-specific memory B cell into a plasmablast-like cell and to stabilize said cell, so that rapid differentiation into a plasma cell does not occur. This is contrary to natural development of plasma cells, wherein expression of Blimp-1 in a memory B cell results in rapid development into a plasma cell, thereby inhibiting BCL6 expression so that the resulting plasma cell hardly expresses BCL6. One embodiment of the present invention thus involves co-expression of both BCL6 and Blimp-1 in an RSV-specific B cell, resulting in a cell that is capable of both proliferating and producing antibody. The BCL6 expression level in said RSV-specific B-cell is preferably brought to, and maintained at, essentially the same level or at a higher level as compared to a plasmablast. This way a stable culture of RSV-specific B cells is generated, which cells remain capable of producing RSV-specific antibodies. These RSV-specific B cells that co-express BCL6 and Blimp-1 are preferably further stabilized through the addition of the anti-apoptotic gene Bcl-xL. With the introduction of Bcl-xL it is now possible to grow plasmablasts under conditions of low cell density. Hence, the invention also provides a method to culture plasmablasts under conditions of low cell density comprising generating an RSV-specific antibody producing cell with expression levels of BCL6, Blimp-1 and Bcl-xL with any of the herein described methods.

The amount of BCL6 expression product (preferably a BCL6 protein) in an RSV-specific antibody producing cell is regulated in a variety of ways.

In one embodiment an antibody producing cell is provided with a compound capable of directly or indirectly influencing BCL6 expression. An antibody producing cell is preferably provided with a compound capable of enhancing BCL6 expression, in order to counteract downregulation of BCL6 during expression of Blimp-1. Such compound preferably comprises a Signal Transducer of Activation and Transcription 5 (STAT5) protein or a functional part, derivative and/or analogue thereof, and/or a nucleic acid sequence coding therefore. STAT5 is a signal transducer capable of enhancing BCL6 expression. There are two known forms of STAT5, STAT5a and STAT5b, which are encoded by two different, tandemly linked genes. Administration and/or activation of STAT5 results in enhanced BCL6 levels. Hence, downregulation of BCL6 by Blimp-1 is at least in part compensated by upregulation expression of BCL6 by STAT5 or a functional part, derivative and/or analogue thereof. Hence, STAT5 or a functional part, derivative and/or analogue thereof is capable of directly influencing BCL6 expression. It is also possible to indirectly influence BCL6 expression. This is for instance done by regulating the amount of a compound which in turn is capable of directly or indirectly activating STAT5 and/or regulating STAT5 expression. Hence, in one embodiment the expression and/or activity of endogenous and/or exogenous STAT5 is increased. It is for instance possible to indirectly enhance BCL6 expression by culturing an antibody producing cell in the presence of interleukin (IL) 2 and/or IL 4 which are capable of activating STAT5.

In one embodiment, an RSV-specific antibody producing cell is provided with a nucleic acid sequence encoding STAT5 or a functional part, derivative and/or analogue thereof, wherein said nucleic acid sequence is constitutively active, meaning that STAT5 is continuously expressed, independent of the presence of (endogenous) regulators. In case that endogenous STAT5 expression is low, or absent, an exogenous constitutively active nucleic acid sequence encoding STAT5 or a functional part, derivative and/or Analogue thereof is preferably applied resulting in a concentration of STAT5 or a functional part, derivative and/or analogue thereof which is sufficient to enhance BCL6 expression. Most preferably, an RSV-specific antibody producing cell is provided with a nucleic acid sequence encoding a compound comprising STAT5 or a functional part, derivative and/or analogue thereof, preferably a fusion protein, whose activity is regulated by an exogenous inducer of repressor, so that the extent of activation of BCL6 expression is regulated at will. Another system that allows for induction of BCL-6 is provided by a Tet-on system in which addition of tetracycline and/or derivatives of tetracycline induce activity of a transactivator that induced BCL6 gene transcription followed by BCL protein synthesis. In one preferred embodiment, an antibody producing cell is provided with a nucleic acid sequence encoding an estrogen receptor (ER) and STAT5 as a fusion protein ER-STAT5. This fusion protein is inactive because it forms a complex with heat shock proteins in the cytosol. This way, STAT5 is unable to reach the nucleus and BCL6 expression is not enhanced. Upon administration of the exogenous inducer 4 hydroxy-tamoxifen (4HT), the fusion protein ER-STAT5 dissociates from the heat shock proteins, so that STAT5 is capable of entering the nucleus and activating BCL6 expression.

Additionally, or alternatively, BCL6 expression in an RSV-specific antibody producing cell is enhanced by culturing said antibody producing cell in the presence of a compound capable of directly or indirectly enhancing BCL6 expression.

One embodiment therefore provides a method for producing an RSV-specific antibody producing cell comprising:
providing an RSV-specific antibody producing cell with a compound capable of directly or indirectly enhancing BCL6 expression; and/or
culturing an RSV-specific antibody producing cell in the presence of a compound capable of directly or indirectly enhancing BCL6 expression. Said compound capable of directly or indirectly enhancing BCL6 expression preferably comprises STAT5 or a functional part, derivative and/or analogue thereof. Provided is therefore a method according to the invention comprising providing said RSV-specific antibody producing cell with STAT5 or a functional part, derivative and/or analogue thereof, or with a nucleic acid sequence encoding STAT5 or a functional part, derivative and/or analogue thereof. In one embodiment said antibody producing cell is cultured after introduction of a nucleic acid sequence encoding STAT5 or a functional part, derivative and/or analogue thereof into said cell. Said nucleic acid sequence is for instance introduced into said cell by transfection and/or virus-mediated gene transfer. Many alternative methods for introducing a nucleic acid sequence into a cell are available in the art which need no further explanation here.

With a compound capable of directly or indirectly enhancing BCL6 expression it is possible to enhance expression of endogenous BCL6. In one preferred embodiment however an antibody producing cell is provided with a nucleic acid sequence encoding BCL6 or a functional part, derivative and/or analogue thereof. As explained herein before, an exogenous nucleic acid encoding BCL6 is preferred because this allows regulation of a BCL6 concentration within a cell independently from expression of endogenous BCL6. Hence, even if expression of endogenous BCL6 is low or absent, for instance caused by Blimp-1, an exogenous nucleic acid sequence encoding BCL6 or a functional part, derivative and/or analogue thereof is still capable of producing a concentration of BCL6 which is sufficient for influencing the stability of an antibody producing cell. Also provided is therefore a method according to the invention comprising providing an RSV-specific antibody producing cell with a nucleic acid sequence encoding BCL6 or a functional part, derivative and/or analogue thereof. Preferably, said antibody producing cell is provided with a constitutively active nucleic acid sequence encoding BCL6 or a functional part, derivative and/or analogue thereof, so that BCL6 expression is maintained even when endogenous BCL6 expression of said cell is inhibited by an endogenous repressor such as Blimp-1. Most preferably, expression of said nucleic acid sequence encoding BCL6 or a functional part, derivative and/or analogue thereof is regulated by an exogenous inducer of repressor, so that the extent of BCL6 expression is regulated at will. For instance, an inducible promoter system is used such as a Tet-on or Tet-off system, as already described.

In another preferred embodiment the invention provides a method wherein the amount of BCL6 is indirectly regulated by providing an RSV-specific antibody producing cell with a nucleic acid sequence encoding E47 or a functional part, derivative and/or analogue thereof. E47 encodes a transcription factor that belongs to a family of helix-loop-helix proteins, named E-proteins. There are four E-proteins, E12, E47, E2-2 and HEB, which are involved in lymphocyte development. E12 and E47 are encoded by one gene, named E2A, which is spliced differently. E-proteins can be inhibited by the E protein inhibitor Id2, and Id3, and by ABF-1 (Mathas S., 2006). E proteins have been described as tumor suppressors and overexpression has been shown to induce apoptosis. One of the specific targets of E47 are the Socs1 and Socs3 genes. Those Socs genes are known as negative regulators of STAT5b and thus indirectly of BCL6. In other words, expression of E47 within a B cell enhances Blimp-1 expression which results in B-cell differentiation towards an antibody producing phenotype (plasmacell).

The amount of Blimp-1 expression in an RSV-specific antibody producing cell is also regulated in a variety of ways. In one embodiment an RSV-specific antibody producing cell is provided with a compound capable of directly or indirectly influencing Blimp-1 expression. Additionally, or alternatively, an antibody producing cell is cultured in the presence of a compound capable of directly or indirectly influencing Blimp-1 expression, Further provided is therefore a method according to the invention comprising providing an RSV-specific antibody producing cell with a compound capable of directly or indirectly influencing Blimp-1 expression. Further provided is a method according to the invention comprising culturing said antibody producing cell in the presence of a compound capable of directly or indirectly influencing Blimp-1 expression. Preferably, a compound is used that is capable of enhancing Blimp-1 expression in order to counteract downregulation of Blimp-1 during expression of BCL6. Said compound most preferably comprises IL-21.

In one preferred embodiment said compound capable of directly or indirectly influencing Blimp-1 expression comprises a Signal Transducer of Activation and Transcription 3 (STAT3) protein or a functional part, derivative and/or analogue thereof, and/or a nucleic acid sequence coding therefore. STAT3 is a signal transducer which is involved in B cell development and differentiation. STAT3 is capable of upregulating Blimp-1 expression. Further provided is therefore a method according to the invention wherein said compound capable of directly or indirectly influencing Blimp-1 expression comprises STAT3 or a functional part, derivative and/or analogue thereof or a nucleic acid sequence encoding STAT3 or a functional part, derivative and/or analogue thereof. Most preferably, expression of said nucleic acid sequence encoding STAT3 or a functional part, derivative and/or analogue thereof is regulated by an exogenous inducer of repressor, so that the extent of STAT3 expression is regulated at will. For instance, an inducible promoter system is used such as for instance a Tet-on or Tet-off system. In one embodiment a fusion product comprising of STAT3, a derivative or analogue, and ER is introduced in said cell allowing regulation of STAT3 expression by hydroxytamoxifen.

Since STAT3 is capable of influencing Blimp-1 expression, it is also possible to indirectly regulate Blimp-1 expression by administering a compound capable of directly or indirectly regulating the activity and/or expression of STAT3. In one embodiment an antibody producing cell is provided with a compound that is capable of enhancing the activity of STAT3, so that Blimp-1 expression is indirectly enhanced as well. Further provided is therefore a method according to the invention, wherein an antibody producing cell is provided with a compound capable of directly or indirectly enhancing activity of STAT3.

Hence, in one embodiment an antibody producing cell is provided with a compound capable of directly or indirectly activating STAT3, in order to enhance Blimp-1 expression.

STAT3 is activated in a variety of ways. Preferably, STAT3 is activated by providing an antibody producing cell with a cytokine. Cytokines, being naturally involved in B cell differentiation, are very effective in regulating STAT proteins. Very effective activators of STAT3 are IL-21 and IL-6, but also IL-2, IL-7, IL-10, IL-15 and IL-27 are known to activate STAT3. Moreover, Toll-like receptors (TLRs) which are involved in innate immunity are also capable of activating STAT3. One embodiment therefore provides a method of the invention, wherein said compound capable of directly or indirectly influencing Blimp-1 expression comprises IL-21, IL-2, IL-6, IL-7, IL-10, IL-15 and/or IL-27. Most preferably IL-21 is used, since IL-21 is particularly suitable for influencing the stability of an antibody producing cell. IL-21 is capable of upregulating Blimp-1 expression even when Blimp-1 expression is counteracted by BCL6.

Additionally, or alternatively a mutated Janus kinase (JAK) is used in order to activate STAT3. Naturally, a JAK is capable of phosphorylating STAT3 after it has itself been activated by at least one cytokine. A mutated Janus kinase capable of activating STAT3, independent of the presence of cytokines, is particularly suitable in a method according to the present invention.

As already explained before, a compound capable of enhancing Blimp-1 expression in one embodiment comprises a nucleic acid sequence encoding STAT3 or a functional part, derivative and/or analogue thereof. The presence of an exogenous nucleic acid sequence encoding STAT3 or a functional part, derivative and/or analogue thereof allows for a continuous presence of STAT3 or a functional part, derivative and/or analogue thereof even when expression of endogenous STAT3 is very low or absent.

It is also possible to decrease expression and/or activity of STAT5 in order to upregulate Blimp-1. If the amount and/or activity of STAT5 is decreased, activation of BCL6 expression is decreased as well, which results in a decreased amount of BCL6 expression product. Since BCL6 and Blimp-1 counteract each other's expression, a decreased amount of BCL6 expression product results in an increased amount of Blimp-1 expression product. Compounds capable of downregulating the activity of STAT5 are thus capable of indirectly upregulating Blimp-1. Such compounds for instance comprise members of the suppressor of cytokine signalling (SOCS) proteins. In one embodiment the amount of Blimp-1 expression product in an RSV-specific antibody producing cell is therefore upregulated by providing said cell with a SOCS protein, and/or by activating a SOCS protein within said cell.

In one preferred embodiment the expression and/or activity of STAT5 is decreased when an RSV-specific antibody-producing cell is provided with a nucleic acid sequence encoding E47 or a functional part, derivative and/or analogue thereof. Expression of E47 within B cells expressing high levels of STAT5b intervenes with differentiation and proliferation, i.e. blocking of STAT5 via E47 and SOCS results in decreased BCL6 levels and subsequently in increased Blimp-1 levels. Upregulated levels of Blimp-1 result in a decreased proliferation and in a differentiation of the involved cell towards an antibody-producing cell. In other words, expression of E47 within a B cell enhances Blimp-1 expression which results in B-cell differentiation towards an antibody producing phenotype (plasma cell).

By at least a functional part of a STAT5 protein, a STAT3 protein, Bcl-xL and/or BCL6 is meant a proteinaceous molecule that has the same capability—in kind, not necessarily in amount—of influencing the stability of an antibody producing cell as compared to a STAT5 protein, a STAT3 protein, Bcl-xL and/or BCL6, respectively. A functional part of a STAT5 protein or a STAT3 protein is for instance devoid of amino acids that are not, or only very little, involved in said capability. A derivative of a STAT5 protein, a STAT3 protein, Bcl-xL and/or BCL6 is defined as a protein which has been altered such that the capability of said protein of influencing the stability of an antibody producing cell is essentially the same in kind, not necessarily in amount. A derivative is provided in many ways, for instance through conservative amino acid substitution wherein one amino acid is substituted by another amino acid with generally similar properties (size, hydrophobicity, etc), such that the overall functioning is likely not to be seriously affected. A derivative for instance comprises a fusion protein, such as a STAT5-ER or STAT3-BR fusion protein whose activity depends on the presence of 4 hydroxy-tamoxifen (4HT). An analogue of a STAT5 protein, a STAT3 protein, Bcl-xL and/or BCL6 is defined as a molecule having the same capability of influencing the stability of an antibody producing cell in kind, not necessarily in amount. Said analogue is not necessarily derived from said STAT5 protein, STAT3 protein, Bcl-xL and/or BCL6.

In one preferred embodiment said RSV-specific antibody producing cell is cultured in the presence of IL-21 before said antibody producing cell is provided with a nucleic acid sequence encoding BCL6 or a functional part, derivative and/or analogue thereof. Culturing RSV-specific antibody producing cells, preferably B cells, in the presence of IL-21 before said cell is provided with a nucleic acid sequence encoding BCL6 or a functional part, derivative and/or analogue thereof is preferred, because in these embodiments stability, proliferation and/or antibody production is particularly well improved.

In a preferred embodiment, the invention provides a method for influencing the stability of an RSV-specific antibody producing cell as described herein, further comprising directly or indirectly increasing the amount of Bcl-xL expression product within said antibody producing cell. This is for example accomplished by providing said antibody producing cell with a nucleic acid sequence encoding Bcl-xL or a functional part, derivative and/or analogue thereof or with nucleic acid sequences encoding other anti-apoptotic genes including but not limited to Bcl-2. In yet another embodiment this is accomplished by providing said antibody producing cell with a compound capable of directly or indirectly enhancing Bcl-xL expression, preferably said compound comprises APRIL, BAFF, CD40, BCR stimulation, cytokines, growth factors or downstream effectors like JNK and AKT (PKB).

Bcl-xL is a member of the anti-apoptotic Bcl-2 family, Bcl2-proteins interact with and counteract so-called Bcl-2 homology domain 3 (BH3)-only family members such as Bax, Bak, Bim, and Bad, which induce cytochome c release following intrinsic death stimuli (Boise, L. H., 1993). Thus, protection of mitochondrial membrane integrity through proteins like Bcl-xL is critical for cell survival.

STAT5 activation has been shown to protect cells from cell death. STAT5 has been shown to regulate the expression of Bcl-xL, supporting an anti-apoptotic role for STAT5. STAT5 positively regulates the Bcl-xL expression through STAT binding elements within the Bcl-xL promoter. In vivo, Bcl-xL expression is absent in bone marrow of STAT5A/B-doubly deficient mice. Furthermore, STAT5-mediated erythroblast survival is dependent upon upregulation of Bcl-xL. Recently, it has been shown that transgenic overexpression of Bcl-xL in mouse B cells promotes B cell survival and nonmalignant plasma cell foci.

A method according to the invention is particularly suitable for producing a cell culture comprising RSV-specific antibody producing cells that are capable of proliferating and secreting antibody. In one embodiment, an RSV-specific memory B cell is used in order to produce an ex vivo B cell culture. Said memory B cell is preferably human so that human antibodies are produced. Said B cell preferably originates from an individual, which individual had been previously exposed to Respiratory Syncytial Virus. In one embodiment RSV-specific B cells are isolated from a peripheral blood sample and/or a tonsil sample, using methods known in the art. Memory B cells are for instance isolated by selection (magnetic beads sorting) for the B cell marker CD 19 and/or CD22 and (subsequent) selection for cell surface IgG and/or CD27 and/or by negative selection for IgM, IgD and/or IgA. In a germinal center B cell, BCL6 expression is high whereas Blimp-1 expression is low. Natural development into an antibody secreting cell involves upregulation of Blimp-1 expression. Since Blimp-1 represses BCL6 expression, upregulation of Blimp-1 results in downregulation of BCL6 in a natural situation. In a preferred embodiment of the present invention however, Blimp-1 expression is upregulated while BCL6 expression is at least in part maintained. This results in an RSV-specific antibody producing cell wherein BCL6 and Blimp-1 are co-expressed. Said RSV-specific antibody producing cell is capable of proliferating and secreting anti-RSV antibodies and is therefore suitable for use in an ex vivo B cell culture. In a further preferred embodiment, said antibody producing cell is protected by apoptosis by Bcl-xL. An RSV-specific antibody producing cell according to the present invention provides the advantage that it is stable and does not undergo terminal differentiation during a prolonged period. Said antibody producing cell according to the invention is stable for at least one week, preferably for at least one month, more preferably for at least three months, most preferably for at least six months. A B cell according to the invention is preferably cultured in the presence of CD40L since replication of most B cells is favoured by CD40L.

In one embodiment BCL6 expression is maintained at essentially the same level, or at a higher level, as compared to a germinal center B cell since a significant BCL6 expression, together with Blimp-1 expression, results in an antibody producing cell with preferred proliferation and antibody production properties and/or stability. In a preferred embodiment, said BCL6 expression and/or Blimp-1 expression are accompanied by Bcl-xL expression, resulting in even more preferred proliferation and antibody production properties and/or stability.

One embodiment therefore provides a method for producing an RSV-specific antibody producing cell which is stable for at least one week, preferably for at least one month, more preferably for at least three months, more preferably for at least six months, the method comprising:
providing an RSV-specific memory B cell;
increasing an expression level of Blimp-1 in said cell; and
increasing and/or maintaining a BCL6 expression level in said cell. An ex vivo method for producing an RSV-specific antibody producing cell comprising increasing an expression level of Blimp-1 in an RSV-specific memory B cell and increasing and/or maintaining a BCL6 expression level in said cell is also provided. Said BCL6 and Blimp-1 expression levels are preferably brought to, and/or maintained at, essentially the same level, or at a higher level, as compared to a plasmablast. In a preferred embodiment said B cell is transduced with BCL6 and Bcl-xL. Further provided is therefore a method for producing an RSV-specific antibody producing cell which is stable for at least three months, comprising:
providing a B cell capable of producing RSV-specific antibodies with BCL6, or a functional part, derivative and/or analogue thereof, and
providing said B cell with Bcl-xL or a functional part, derivative and/or analogue thereof; and
culturing said B cell.

Said B cell is preferably provided with a nucleic acid sequence encoding BCL6, or a functional part, derivative and/or analogue thereof; and with a nucleic acid sequence Bcl-xL or a functional part, derivative and/or analogue thereof.

Said B cell is preferably cultured in the presence of a compound capable of enhancing Blimp-1 expression, such as for instance IL-21, IL-2, IL-6, IL-7, IL-10, IL-15, IL-27, or a mutated Janus kinase. Preferably, IL-21 is used because this cytokine is particularly suitable for enhancing Blimp-1 expression and stabilizing an antibody producing cell with a method according to the present invention. Moreover, in order to enhance transduction efficacy, said B cell is preferably cultured in the presence of IL-21 before said B cell is transduced with a nucleic acid sequence encoding BCL6 and/or Bcl-xL, or a functional part, derivative and/or analogue thereof.

In one embodiment said B cell is provided with a SOCS protein or a functional part, derivative and/or analogue thereof, or a nucleic acid coding therefore, since a SOCS protein or a functional part, derivative and/or analogue thereof is capable of indirectly enhancing Blimp-1 expression. In another alternative or additional embodiment, said B-cell is provided with E47 or a functional part, derivative and/or analogue thereof, or a nucleic acid coding therefore. As already outlined earlier, as a result of an increased level of B47 or a functional part, derivative and/or analogue thereof, SOCS protein function is enhanced and Blimp-1 expression is indirectly increased.

In the Examples particularly preferred embodiments are shown. According to one particularly preferred embodiment, RSV-specific B cells are firstly cultured in the presence of IL-21. Subsequently the B cells are subjected to a transduction reaction using a nucleic acid encoding BCL6 and a nucleic acid encoding Bcl-xL. Preferably spin transduction is used. Most preferably, B cells and virus comprising at least one nucleic acid of interest are mixed, where after the mixture is spinned in order to achieve a high transduction efficacy. After transduction, the B cells are cultured in the absence of IL-21 and in the presence of IL-4 and L-cells during 3-5 days in order to allow BCL6 expression. Subsequently, according to this preferred embodiment, the B cells are subjected again to a transduction reaction using a nucleic acid encoding BCL6 and a nucleic acid encoding Bcl-xL. Afterwards, the B cells are again cultured in the absence of IL-21 and in the presence of IL-4 and L-cells during 3-5 days in order to allow BCL6 expression. Subsequently, cells expressing BCL6 and Bcl-xL are isolated and IL-21 is administered again to the culture in order to enhance replication and antibody production. Antibodies that are secreted by Bcl-6, Blimp 1 and Bcl-XL expressing cells in the culture supernatant are preferably screened for in vitro neutralizing capacity/activity/reactivity to RSV. Antibody producing cells that produce those antibodies are preferably further selected, for instance by limiting dilution culture. Stable RSV-specific B cells are thus obtained wherein BCL6 and Blimp-1 are co-expressed. Said B cells are capable of replicating and producing antibody in an in vitro culture during at least six months.

One embodiment provides a method according to the invention further comprising selecting and/or isolating an RSV-specific antibody or a functional equivalent thereof. In one embodiment IgM producing cells and IgG producing cells are selected and/or isolated. Preferably an IgG producing cell is selected and/or isolated.

RSV-specific antibody producing cells generated with a method according to the invention are suitable for producing antibodies against RSV. In one preferred embodiment however, the genes encoding the Ig heavy and/or light chains are isolated from said cell and expressed in a second cell, such as for instance cells of a Chinese hamster ovary (CHO) cell line or 293(T) cells. Said second cell, also called herein a producer cell, is preferably adapted to commercial antibody production. Proliferation of said producer cell results in a producer cell line capable of producing RSV-specific antibodies. Preferably, said producer cell line is suitable for producing compounds for use in humans. Hence, said producer cell line is preferably free of pathogenic agents such as pathogenic microorganisms.

A method according to the invention is preferably used for generating an antibody producing cell that is stable for at least one week, preferably at least one month, more preferably at least three months, more preferably at least six months so that commercial antibody production has become possible. Most preferably a stable cell line capable of producing monoclonal antibodies is produced. This is preferably performed by using memory B cells that have for instance been isolated from a sample by selection for CD 19 and/or CD22 (B cell marker) and cell surface IgG and/or CD27 (to mark memory cells) and/or by negative selection for IgM, IgD and/or IgA. Furthermore, an RSV-specific antibody producing cell is for instance selected in a binding assay using RSV or a component derived from RSV, such as for instance the RSV F protein, 0 protein and/or SH protein. Subsequently, according to this preferred embodiment Blimp-1 and BCL6 are co-expressed in said RSV-specific antibody producing cell, resulting in a culture of cells capable of specifically binding (a component of) RSV. In yet another preferred embodiment, said B cell is further provided with Bcl-xL or a functional part, derivative and/or analogue thereof.

If only one memory cell is used, a cell line according to the invention which produces monoclonal antibodies is obtained. It is also possible to generate a monoclonal antibody producing cell line starting with B cells capable of producing antibodies against RSV. After a stable B cell culture has been produced with a method according to the invention, a B cell capable of producing antibodies against a specific antigen of RSV is isolated and at least a functional part of a gene encoding the Ig heavy chain and/or light chain from said B cell is preferably expressed in a second cell line. Preferably at least a functional part of the gene encoding the Ig heavy chain and at least a functional part of the gene encoding the Ig light chain from said B cell are expressed in a second cell line.

In one embodiment an antibody producing cell, preferably but not necessarily a memory B cell, that has been obtained from an individual which had been previously exposed to RSV, is used in a method according to the invention. This way, it has become possible to produce human antibodies of interest ex vivo.

Further provided is therefore a method for producing antibodies which are capable of specifically binding and/or neutralizing Respiratory Syncytial Virus, the method comprising:
producing an antibody producing cell capable of producing RSV-specific antibodies with a method according to the invention; and
obtaining antibodies produced by said antibody producing cell.

An isolated or recombinant antibody, as well as an isolated or recombinant antibody producing cell, obtainable by a method according to the invention, or a functional equivalent thereof, is also provided. Said antibody preferably comprises antibody D25, AM14, AM16 and/or AM23, or a functional part, derivative or analogue thereof.

Once an RSV-specific antibody producing cell according to the invention is obtained, at least a functional part of a gene encoding the Ig heavy chain and/or light chain of said cell is preferably isolated and/or generated artificially. In one embodiment a nucleic acid sequence comprising at least a functional part of a nucleic acid sequence as depicted in FIG. 11A, FIG. 12, and/or FIGS. 14A-14L is provided. Said functional part preferably comprises at least one nucleic acid sequence as depicted in FIG. 11A, FIG. 12, and/or FIGS. 14A-14L. Said functional part preferably encodes at least one CDR as depicted in FIGS. 11B and 11C, FIG. 12, FIG. 14C, FIG. 14G and/or FIG. 14K.

Further provided is an isolated, synthetic or recombinant nucleic acid sequence comprising a heavy chain sequence which is at least 70%, preferably at least 80%, more preferably at least 90% homologous to at least part of the sequence CAGGTGCAGCTGGTACAGTCTGGGGCTGAAGTGAAGAAGCCTGGGTCCTCGGTGATGGTCTCCTGCCAGGCCTCTGGAGGCCCCCTCAGAA (SEQ ID NO: 59), ACTATATTATCAAC (SEQ ID NO: 60), TGGCTACGACAGGCCCCTGGACAAGGCCCTGAGTGATGGGA (SEQ ID NO: 61), GGGATCATTCCTGTCTTGGGTACAGTACACTACGCACCGAAGTTCCAGGGC (SEQ ID NO: 62), AGAGTCACGATTACCGCGGACGAATCCACAGACACAGCCTACATCCATCTGATCAGCCTGAG ATCTGAGGACACGGCCATGTATTACTGTGCGACG (SEQ ID NO: 63), GAAACAGCTCTGGTTGTATCTACTACCTACCTACCACACTACTTTGACAAC (SEQ ID NO: 64), TGGGGCCAGGGAACCCTGGTCACCGTCTCCTCAG (SEQ ID NO: 65), and/or CAGGTGCAGCTGGTACAGTCTGGGGCTGAAGTGAAGAAGCCTGGGTCCTCGGTGATGGTCTC CTGCCAGGCCTCTGGAGGCCCCCTCAGAAACTATATTATCAACTGGCTACGACAGGCCCCTG GACAAGGCCCTGAGTGATGGGAGGGATCATTCCTGTCTTGGGTACAGTACACTACGCACCG AAGTTCCAGGGCAGAGTCACGATTACCGCGGACGAATCCACAGACACAGCCTACATCCATCT GATCAGCCTGAGATCTGAGGACACGGCCATGTATTACTGTGCGACGGAAACAGCTCTGGTTG TATCTACTACCTACCTACCACACTACTTTGACAACTGGGGCCAGGGAACCCTGGTCACCGTC TCCTCAG (SEQ ID NO: 9), said part having at least 15 nucleotides. Said heavy chain sequence is preferably derived from antibody D25. Said heavy chain sequence preferably comprises a sequence which is at least 70%, preferably at least 80%, more preferably at least 90% homologous to a sequence as depicted in FIG. 11A. An isolated, synthetic or recombinant nucleic acid sequence comprising a heavy chain sequence consisting of any of the above mentioned heavy chain sequences is also herewith provided.

An isolated, synthetic or recombinant nucleic acid sequence comprising a light chain sequence which is at least 70%, preferably at least 80%, more preferably at least 90% homologous to a least part of the sequence GACATCCAGATGACCCAGTCTCCATCCTCCCTGTCTGCAGCTGTAGGAGACAGAGTCACCAT CACTTGC (SEQ ID NO: 66), CAGGCGAGTCAGGACATTGTCAACTATTTAAAT (SEQ ID NO: 67), TGGTATCAACAGAAACCAGGGAAAGCCCCTAAGCTCCTGATCTAC (SEQ ID NO: 68), GTTGCATCCAATTTGGAGACA (SEQ ID NO: 69), GGGGTCCCATCAAGGTTCAGTGGAAGTGGATCTGGGACAGATTTTAGTCTCACCATCAGCAG CCTGCAGCCTGAAGATGTTGCAACATATTATTGT (SEQ ID NO: 70), CAACAATATGATAATCTCCCA (SEQ ID NO: 71), CTCACATTCGGCGGAGGGACCAAGGTTGAGATCAAAAGA (SEQ ID NO: 72) and/or GACATCCAGATGACCCAGTCTCCATCCTCCCTGTCTGCAGCTGTAGGAGACAGAGTCACCAT CACTTGCCAGGCGAGTCAGGACATTGTCAACTATTTAAATTGGTATCAACAGAAACCAGGGA AAGCCCCTAAGCTCCTGATCTACGTTGCATCCAATTTGGAGACAGGGGTCCCATCAAGGTTC AGTGGAAGTGGATCTGGGACAGATTTTAGTCTCACCATCAGCAGCCTGCAGCCTGAAGATGT TGCAACATATTATTGTCAACAATATGATAATCTCCCACTCACATTCGGCGGAGGGACCAAGG TTGAGATCAAAAGA (SEQ ID NO: 10), said part having at least 15 nucleotides, is also provided. Said light chain sequence is preferably derived from antibody D25.

Said light chain sequence preferably comprises a sequence which is at least 70%, preferably at least 80%, more preferably at least 90% homologous to a sequence as depicted in FIG. 11A. An isolated, synthetic or recombinant nucleic acid sequence comprising a heavy chain sequence consisting of any of the above mentioned light chain sequences is also herewith provided.

Further provided is an isolated, synthetic or recombinant nucleic acid sequence comprising a heavy chain sequence which is at least 70%, preferably at least 80%, more preferably at least 90% homologous to at least part of the sequence GAGGTGCAGCTGGTGGAGTCTGGGGGAGGCGTGGTCCAGCCTGGGAGGTCCCTGAGACTCTC CTGTGCGGCCTCT (SEQ ID NO: 94), GGATTCAGCT- TCAGTCACTATGCC (SEQ ID NO: 95), ATGCACTGGGTCCGCCAGGCTCCAGGCAAGGGACTGGAGTGGGTGGCAGTT (SEQ ID NO: 96), ATATCTTATGATGGAGAAAATACA (SEQ ID NO: 97), TATTACGCAGACTCCGTGAAGGGCCGATTCTCCATCTCCAGAGACAATTCCAAGAACACAGT GTCTCTGCAAATGAACAGCCTGAGACCTGAGGACACGGCTCTATATTACTGT (SEQ ID NO: 98), GCGAGAGACCGCATAGTGGACGACTACTACTACGGTATGGACGTC (SEQ ID NO: 99), TGGGGCCAAGGGGCCACGGTCACCGTCTCCTCAG (SEQ ID NO: 100) and/or GAGGTGCAGCTGGTGGAGTCTGGGGGAGGCGTGGTCCAGCCTGGGAGGTCCCTGAGACTCTC CTGTGCGGCCTCTGGATTCAGCTTCAGTCACTATGCCATGCACTGGGTCCGCCAGGCTCCAG GCAAGGGACTGGAGTGGGTGGCAGTTATATCTTATGATGGAGAAAATACATATTACGCAGAC TCCGTGAAGGGCCGATTCTCCATCTCCAGAGACAATTCCAAGAACACAGTGTCTCTGCAAAT GAACAGCCTGAGACCTGAGGACACGGCTCTATATTACTGTGCGAGAGACCGCATAGTGGACG ACTACTACTACGGTATGGACGTCTGGGGCCAAGGGGCCACGGTCACCGTCTCCTCA (SEQ ID NO: 101), said part having at least 15 nucleotides. Said heavy chain sequence is preferably derived from antibody AM14. An isolated, synthetic or recombinant nucleic acid sequence comprising a heavy chain sequence consisting of any of the above mentioned heavy chain sequences is also herewith provided.

An isolated, synthetic or recombinant nucleic acid sequence comprising a light chain sequence which is at least 70%, preferably at least 80%, more preferably at least 90% homologous to a least part of the sequence GACATCCAGATGACCCAGTCTCCATCTTCCCTGTCTGCATCTGTAGGAGACAIGAGTCACCAT CACTTGCCAGGCGAGT (SEQ ID NO: 102), CAGGACATTAAGAAGTAT (SEQ ID NO: 103), TTAAATTGGTATCATCAGAAACCAGGGAAAGTCCCTGAGCTCCTGATGCAC (SEQ ID NO: 104), GATGCATCC, AATTTGGAAACAGGGGTCCCATCAAGGTTCAGTGGCAGGGGATCTGGACAGATTTTACTCT CACCATTAGCAGCCTGCAGCCTGAAGATATTGGAACATATTACTGT (SEQ ID NO: 105), CAACAGTATGATAATCTGCCTCCGCTCACT (SEQ ID NO: 106), TTCGGCGGAGGGACCAAGGTGGAGATCAAAC (SEQ ID NO: 107) and/or GACATCCAGATGACCCAGTCTCCATCTTCCCTGTCTGCATCTGTAGGAGACAGAGTCACCAT CACTTGCCAGGCGAGTCAGGACATTAAGAAGTATTTAAATTGGTATCATCAGAAACCAGGGA AAGTCCCTGAGCTCCTGATGCACGATGCATCCAATTTGGAAACAGGGGTCCCATCAAGGTTC AGTGGCAGGGGATCTGGACAGATTTTACTCTCACCATTAGCAGCCTGCAGCCTGAAGATAT TGGAACATATTACTGTCAACAGTATGATAATCTGCCTCCGCTCACTTTCGGCGGAGGGACCA AGGTGGAGATCAAACGAACTGTG (SEQ ID NO: 108), said part having at least 15 nucleotides, is also provided. Said light chain sequence is preferably derived from antibody AM14. An isolated, synthetic or recombinant nucleic acid sequence comprising a heavy chain sequence consisting of any of the above mentioned light chain sequences is also herewith provided.

Further provided is an isolated, synthetic or recombinant nucleic acid sequence comprising a heavy chain sequence which is at least 70%, preferably at least 80/%, more preferably at least 90% homologous to at least part of the sequence GAGGTGCAGCTGGTGGAGACCGGGGAGGCCTGGCCCAGCCTGGGGGGTCCCTGAGACTCTC CTGTGCAGCCTCT (SEQ ID NO: 109), GGATTCACATTCAGTAGTTATAAC (SEQ ID NO: 110), ATGAACTGGGTCCGCCAGGCTCCAGGGAAGGGGCTGGAGTGGGTCTCACAC (SEQ ID NO: 111), ATTAGTGCGGGTAGTAGTTACATA (SEQ ID NO: 112), TACTACTCAGACTCAGTGAAGGGCCGATTCACCGTCTCCAGAGACAACGTCAGGAACTCAGT ATATCTGCAAATGAACAGCCTGAGAGCCGCTGACACGGCTGTGTATTACTGT (SEQ ID NO: 113), GCGAGAGAGGATTATGGTCCGGGAAATTATTATAGTCCTAACTGGTTCGACCCC (SEQ ID NO: 114), TGGGGCCAGGGAACCCTGGTCACCGTCTCCTCAG (SEQ ID NO: 115) and/or GAGGTGCAGCTGGTGGAGACCGGGGGAGGCCTGGCCCAGCCTGGGGGGTCCCTGAGACTCTC CTGTGCAGCCTCTGGATTCACATTCAGTAGTTATAACATGAACTGGGTCCGCCAGGCTCCAG GGAAGGGGCTGGAGTGGGTCTCACACATTAGTGCGGGTAGTAGTTACATATACTACTCAGAC TCAGTGAAGGGCCGATTCACCGTCTCCAGAGACAACGTCAGGAACTCAGTATATCTGCAAAT GAACAGCCTGAGAGCCGCTGACACGGCTGTGTATTACTGTGCGAGAGAGGATTATGGTCCGG GAAATTATTATAGTCCTAACTGGTTCGACCCCTGGGGCCAGGGAACCCTGGTCACCGTCTCC TCA (SEQ ID NO: 116), said part having at least 15 nucleotides. Said heavy chain sequence is preferably derived from antibody AM16. An isolated, synthetic or recombinant nucleic acid sequence comprising a heavy chain sequence consisting of any of the above mentioned heavy chain sequences is also herewith provided.

An isolated, synthetic or recombinant nucleic acid sequence comprising a light chain sequence which is at least 70%, preferably at least 80%, more preferably at least 90% homologous to a least part of the sequence CAGTCTGTCGTGACGCAGCCGCCCTCAGTGTCTGGGGCCCCAGGGCAGAGAGTCACCATCTC CTGCACTGGGAGC (SEQ ID NO: 117), AGCTCCAACATCGGGGCAGGTTATGAT (SEQ ID NO. 118), GTACACTGGTACCAGCAGCTTCCAGGAACAGCCCCCAAAACTCCTCATCTAT (SEQ ID NO: 119), GGCAACACT, AATCGGCCCTCAGGGGTCTCCGACCGATTCTCTGGCTCCAAGTCTGGCACCTCAGCCTCCCT GGCCATCACTGGACTCCAGGCTGAGGATGAGGCTGATTATTACTGC (SEQ ID NO: 120), CACTCCTATGACAGAAGCCTGAGTGGT (SEQ ID NO: 121), TCAGTATTCGGCGGAGGGACCAAGCTGACCGTCCTAG (SEQ ID NO: 122) and/or CAGTCTGTCGTGACGCAGCCGCCCTCAGTGTCTGGGGCCCCAGGGCAGAGAGTCACCATCTC CTGCACTGGGAGCAGCTCCAACATCGGGGCAGGTTATGATGTACACTGGTACCAGCAGCTTC CAGGAACAGCCCCCAAACTCCTCATCTATGGCAACACTAATCGGCCCTCAGGGGTCTCCGAC CGATTCTCTGGCTCCAAGTCTGGCACCTCAGCCTCCCTGGCCATCACTGGACTCCAGGCTGA GGATGAGGCTGATTATTACTGCCACTCCTATGACAGAAGCCTGAGTGGTTCAGTATTCGGCG GAGGGACCAAGCTGACCGTC (SEQ ID NO: 123), said part having at least 15 nucleotides, is also provided. Said light chain sequence is preferably derived from antibody AM16. An isolated, synthetic or recombinant nucleic acid sequence comprising a heavy chain sequence consisting of any of the above mentioned light chain sequences is also herewith provided.

Further provided is an isolated, synthetic or recombinant nucleic acid sequence comprising a heavy chain sequence which is at least 70%, preferably at least 80%, more preferably at least 90% homologous to at least part of the sequence CAGGTGCAACTGGTG-GAGTCTGGGGGAAATGTGGTCAAGC-CTGGGACGTCCCTGAGACTGTC CTGTGCAGCGACT (SEQ ID NO: 124), GGATTCAACTTCCATAACTACGGC (SEQ ID NO: 125), ATGAACTGGGTCCGCCAGGCTC-CAGGCAAGGGGCTGGAGTGGGTGGCGGTT (SEQ ID NO: 126), GTTTGGTATGATGGAAGTAAGAAA (SEQ ID NO: 127), TACTATGCAGACTCCGTGACGGGCCGAT-TCGCCATCTCCAGAGACAATTCCAAGAACACTCT GTATCTGCAAATGAACAGCCTGAGAGTCGAGGA-CACGGCTGTTTATTATTGT (SEQ ID NO: 128), GTGAGAGATAAAGTGGGACCGACTCCCTACTTT-GACTCC (SEQ ID NO: 129), TGGGGCCAGGGAAC-CCTGGTCACCGTATCCTCAG (SEQ ID NO: 130) and/or GAGGTGCAGCTGGTGGAGTCTGGGGGAAATGTG-GTCAAGCCTGGGACGTCCCTGAGACTGTC CTGT-GCAGCGACTGGATTCAACTTCCATAACTACGGCAT-GAACTGGGTCCGCCAGGCTCCAG GCAAGGGGCTGGAGTGGGTGGCGGTTGTTTGTAT-GATGGAAGTAAGAAATACTATGCAGAC TCCGT-GACGGGCCGATTCGCCATCTCCAGAGACAATTC-CAAGAACACTCTGTATCTGCAAAT GAACAGCCTGAGAGTCGAGGACACGGCTGTTTAT-TATTGTGTGAGAGATAAAGTGGGACCGA CTC-CCTACTTTGACTCCTGGGGCCAGGGAACCCTGGT-CACCGTCTCGAGT (SEQ ID NO: 131), said part having at least 15 nucleotides. Said heavy chain sequence is preferably derived from antibody AM23. An isolated, synthetic or recombinant nucleic acid sequence comprising a heavy chain sequence consisting of any of the above mentioned heavy chain sequences is also herewith provided.

An isolated, synthetic or recombinant nucleic acid sequence comprising a light chain sequence which is at least 70%, preferably at least 80%, more preferably at least 90% homologous to a least part of the sequence TCCTATGT-GCTGACTCAGCCACCCTCGGTGTCACTGGCCCCA-GGAGGGACGGCCGCGATCAC CTGTGGAAGAAAC (SEQ ID NO: 132), AACATTGGAAGTGAAACT (SEQ ID NO: 133), GTGCACTGGTACCAGCAGAAGCCAGGC-CAGGCCCTGTGCTGGTCGTCTAT (SEQ ID NO: 134), GATGATGAC, GACCGGCCCTCAGGGATCCCTGAGC-GATTCTCTGGCTCCAACTCTGGGAACACGGCCAC-CCT GACCATCAGCAGGGTCGAGGCCGGGGATGAG-GCCGACTATTACTGT (SEQ ID NO: 135), CAGGTGTGGGATAGGAGTAATTATCATCAGGTA (SEQ ID NO: 136), TTCGGCGGAGGGACCAAGTT-GACCGTCCTAG (SEQ ID NO: 137) and/or TCCTATGT-GCTGACTCAGCCCCCCTCGGTGTCACTGGCCCCA-GGAGGGACGGCCGCGATCAC CTGTGGAAGAAACAACATTGGAAGTGAAACTGTG-CACTGGTACCAGCAGAAGCCAGGCCAGG CCCCT-GTGCTGGTCGTCTATGATGATGACGACCGGC-CCTCAGGGATCCCTGAGCGATTCTCT GGCTCCAACTCTGGGAACACGGCCACCCTGAC-CATCAGCAGGGTCGAGGCCGGGGATGAGGC CGACTATTACTGTCAGGTGTGGGATAGGAGTAAT-TATCATCAGGTATTCGGCGGAGGGACCA AGCTGAC-CGTC (SEQ ID NO: 138), said part having at least 15 nucleotides, is also provided. Said light chain sequence is preferably derived from antibody AM23. An isolated, synthetic or recombinant nucleic acid sequence comprising a heavy chain sequence consisting of any of the above mentioned heavy chain sequences is also herewith provided.

A nucleic acid sequence encoding an amino acid sequence which is at least 70%, preferably at least 80%, more preferably at least 90% identical to at least a functional part of an amino acid sequence as depicted in FIG. 11, and/or FIGS. 14A-14L, said part having at least 5 amino acid residues is also provided. Said nucleic acid sequence preferably encodes an amino acid sequence which is at least 80% identical to heavy chain CDR sequence 1, 2 and/or 3 and/or light chain CDR sequence 1 or 2 depicted in FIGS. 11B and 11C. In another preferred embodiment said nucleic acid sequence encodes an amino acid sequence which is at least 80% identical to at least one of the CDR sequences depicted in FIG. 14C, FIG. 14G, and/or FIG. 14K. In one preferred embodiment said nucleic acid sequence encodes an amino acid sequence which is at least 70% identical to a heavy chain sequence depicted in FIG. 11A, to a heavy chain sequence depicted in FIG. 14A, to a heavy chain sequence depicted in FIG. 11B, to a heavy chain sequence depicted in FIG. 14I, to a light chain sequence depicted in FIG. 11A, to a light chain sequence depicted in FIG. 14A, to a light chain sequence depicted in FIG. 14E, and/or to a light chain sequence depicted in FIG. 14I.

Further provided is therefore an isolated, synthetic or recombinant nucleic acid sequence comprising a sequence encoding an amino acid sequence which is at least 70%, preferably at least 80%, more preferably at least 85% identical to an amino acid sequence as depicted in FIG. 11. Said nucleic acid sequence preferably encodes an amino acid sequence which is at least 80% identical to heavy chain CDR sequence 1, 2 and/or 3 and/or light chain CDR sequence 1 or 2 as depicted in FIGS. 11B and 11C. One embodiment provides an isolated, synthetic or recombinant nucleic acid sequence comprising a sequence encoding an amino acid sequence which is at least 70% identical to the amino acid sequence NYIIN (SEQ ID NO: 1), and/or at least 75% identical to the sequence GIIPVLGTVHYAPKFQG (SEQ ID NO: 2), and/or at least 70% identical to the sequence ETALVVSTTYLPHYFDN (SEQ ID NO: 3), and/or at least 85% identical to the sequence QASQDIVNYLN (SEQ ID NO: 4), and/or at least 70% identical to the sequence VASNLET (SEQ ID NO: 5), and/or at least 70% identical to the sequence QVQLVQSGAEVKKPGSSVM-VSCQASGGPLRNYIINWLRQAPGQGPEWMGGIIPV-LGT VHYAPKFQGRVTITADESTDTAYIHLISLRSED-TAMYYCATETALVVSTTYLPHYFDN WGQGTLVTVSS (SEQ ID NO: 7), and/or at least 70% identical to the sequence DIQMTQSPSSLSAAVGDRVTITCQASQDIV-NYLNWYQQKPGKAPKLLIYVASNLETG VPSRF-SGSGSGTDFSLTISSLQPEDVATYYQQYDNLPLTFT-VERTV (SEQ ID NO: 8).

A nucleic acid sequence according to the invention is preferably at least 80%, more preferably at least 85%, more preferably at least 90%, most preferably at least 95% homologous to any of the above recited sequences.

Further provided is an isolated, synthetic or recombinant nucleic acid sequence comprising a sequence encoding an amino acid sequence which is at least 70%, preferably at least 80%, more preferably at least 85% identical to an amino acid sequence as depicted in FIG. 14A-C. Said nucleic acid sequence preferably encodes an amino acid sequence which is at least 70% identical to a CDR sequence as depicted in any one of FIGS. 14A-14L. One embodiment provides an isolated, synthetic or recombinant nucleic acid sequence comprising a sequence encoding an amino acid sequence which is at least 70% identical to an amino acid sequence selected from the group consisting of: GFSFSHYA (SEQ ID NO: 73), ISYDGENT (SEQ ID NO: 74), ARDRIVDDYYYYGMDV (SEQ ID NO: 75), QDIKKY (SEQ ID NO: 76), DAS, QQYDNLPPLT (SEQ ID NO: 77), EVQLVBSGGGVVQPORSLRLSCAASGFSFSHYAMH-
WVRQAPGKGLEWVAVISYDGE NTYYADSVKGRF-
SISRDNSKNTVSLQMNSLRPEDTALYYCARDRIVD-
DYYYYGMDV WGQGATVTVSS (SEQ ID NO: 78),
DIQMTQSPSSLSASVGDRVTITCQASQDIKKYLN-
WYHQKPGKVPELLMHDASNLETG VPSRFSGRGS-
GTDFTLTISSLQPEDIGTYYCQQYDNLPPLTFOGGTK-
VEIKRTV (SEQ ID NO: 79), GFTFSSYN (SEQ ID NO: 80), ISAGSSYI (SEQ ID NO: 81), AREDYGPGNYYSP-NWFDP (SEQ ID NO: 82), SSNIGAGYD (SEQ ID NO: 83), GNT, HSYDRSLSG (SEQ ID NO: 84), EVQL-
VETGGGLAQPGGSLRLSCAASGFTFSSYNMN-
WVRQAPGKGLEWVSHISAGSS YIYYSDSVKGRFT-
VSRDNVRNSVYLQMNSLRAADTAVYYCAREDYGP-
GNYYSPNW FDPWOQGTLVTVSS (SEQ ID NO: 85), QSVVTQPPSVSGAPGQRVTISCTGSSSNIGAoYDVI-
WYQQLPGTAPKLLIYGNTNRPS GVSDRFSGSKSGT-
SASLAITOLQAEDEADYYCHSYDRSLSGSVFGGGT-
KLTV (SEQ ID NO: 86), GFNFHNYG (SEQ ID NO: 87), VWYDGSKK (SEQ ID NO: 88), VRDKVGPTPYFDS (SEQ ID NO: 89), NIGSET (SEQ ID NO: 90), DDD, QVWDPRSNYHQV (SEQ ID NO: 91), EVQLVBSOGNV-
VKPGTSLRLSCAATGFNFHNYGMNWVRQAPGK-
GLEWVAVVWYD GSKKYYADSVTGRFAISRDNSKNT-
LYLQMNSLRVEDTAVYYCVRDKVGPTPYFDSW
GQGTLVTVSS (SEQ ID NO: 92), and SYVLTQPPSVS-
LAPGGTAAITCGRNNIGSETVHWYQQKPGQAPVLV-
VYDDDDRPSGI PERFSGSNSGNTATLTISRVEA-
GDEADYYCQVWDRSNYHQVFGGGTKLTV (SEQ ID NO: 93).

A nucleic acid sequence according to the invention is preferably at least 80%, more preferably at least 85%, more preferably at least 90%, most preferably at least 95% homologous to any of the above recited sequences.

As already explained herein before, nucleic acid sequences according to the present invention are particularly suitable for expressing an antibody or a functional part, derivative or analogue thereof according to the invention, preferably D25, AM14, AM16, AM23 or a functional part, derivative and/or analogue thereof, in a nucleic acid expression system. A nucleic acid sequence according to the present invention is preferably expressed in a cell, more preferably in a producer cell adapted for antibody production.

The invention is further explained in the following examples. These examples do not limit the scope of the invention, but merely serve to clarify the invention.

EXAMPLES

Materials and Methods
Maintenance and Isolation of Human B Cells

Using standard procedures, CD19 positive human B cells were isolated from bloodbank derived buffy coat (other sources can be fresh blood with an anticoagulation factor, or a lymphoid organ for example tonsil or spleen). In brief, total peripheral blood mononuclear cells (PBMC) were isolated using ficoll density separation (Amersham, Buckinghamshire, UK). CD22 labeled beads were used to positively selected B cells by MACS cell sorting technique as described by the manufacturer (Miltenyi, Utrecht, Netherlands). Cells were subsequently stained with appropriate combinations of monoclonal antibodies (mAbs) to CD19, CD27, IgD, IgM and IgA (Becton Dickinson (BD), Franklin Lakes, N.J., USA). Memory B cells that are positive for CD19 and CD27 and negative for IgM, IgA and IgD were then sorted using the FACSAria (BD) (FIG. 1). Besides memory B cells, other B cells subsets, like naïve, naïve, follicular, memory, antibody producing, centroblast, ceatrocyte, germinal center, plasma blast, plasma cell, marginal zone, perisinusoidal or transitional B cells (many of those subsets have only been determined in mice) can be isolated using appropriate markers.

Cell Culture

Sorted cells were washed and cultured in 24 well plates (1.5 to $2 \times 10^5$ cells/ml) on 80 Gray, irradiated CD40L-expressing L-cells ($5 \times 10^4$ cells/ml; provided by DR. J. Banchereau, Schering Plough France, Dardilly France), in complete medium (Iscove's Modified D Minimal Essential Medium containing 8% fetal calf serum (FCS) and Penicillin/Streptomycin). Unless mentioned otherwise, these CD40L-expressing L-cells are always present in the cultures in combination with 8% FCS. To prepare the B cell for retroviral transduction cells were cultured for 36 hours in the presence of mouse IL-21 (50 ng/ml, R&D, Minneapolis, Minn., USA). After transduction cells are preferentially cultured in the presence of IL-21, however cells do respond to IL-4, IL-15 and IL-10 (not excluding other cytokines). For example, IL-4 induced B cell expansion is lower compared to IL-21 and lower levels of cell division can be required in some experiments.

Retroviral Constructs and Production of Recombinant Retrovirus

Constitutive active mutants of STAT5a and b have been described previously. DNAs encoding these mutants and wildtype STAT5b were obtained from T. Kitamura (IMSUT, Tokyo, Japan). Bcl-6 was identified in a senescence rescue screen in murine fibroblasts as an inhibitor of anti-proliferative p19ARF-p53 signaling. Bcl-XL was identified as an anti-apoptose factor, which was kindly provided by Dr Korsmeyer (Howard Hughes Medical Institute, Boston, US). These DNAs were ligated into LZRS-linker-IRES-GFP (or IRES-YFP or IRES-NGFR) vector that was described previously (Heeniskerk et al., 1997; Heemakerk et al, 1999). Instead of the IRES-GFP (Green Fluorescent Protein) marker also an IRES-YFP (Yellow Fluorescent Protein) or an IRES-NGFR (Nerve Growth Factor Receptor) was used. NGFR is a signaling-incompetent mutant of the NGFR, kindly provided by Dr. C. Bonini A monoclonal antibody against NGFR (Chromaprobe, Mountain View, Calif., US or Miltenyi) was used to visualize NGFR-expressing cells.

For production of recombinant retrovirus, the retroviral plasmids were transfected into a helper-virus free amphotropic producer cell line Phoenix-A, a derivative of the human embryonic kidney cell line 293 (Kinsella and Nolan, 1996) (a kind gift of Dr. G, Nolan, Stanford University, Palo Alto, Calif.), using Fugene-6 (Roche Diagnostics Netherlands, Almere, Netherlands) according to manufacturers protocols. Two days later selection of transfected cells started by the addition of 2 µg/ml puromycin (Becton Dickinson Clontech Laboratories, Palo Alto, Calif.). Ten to 14 days after transfection $6 \times 10^6$ cells were plated per 10 cm petridish (Becton Dickinson Discovery Labware, Bedford, Mass.) in 10 ml complete medium without puromycin. The next day the medium was refreshed and on the following day retroviral supernatant was harvested, centrifuged and frozen in cell free aliquots at $-70°$ C. This approach affords a reproducible rapid, large scale and high titer retroviral production of over $3 \times 10^6$ infectious virus particles/ml.

Retroviral Transduction

The recombinant human fibronectin fragments CH-296 transduction procedure (RetroNectin™; Takara, Otsu, Japan) was performed as described previously (Heemskerk et at, 1997; Heemskerk et al., 1999). Non-tissue culture-treated 24 wells plates (Costar, Badhoevedorp, Netherlanda)

were coated with 0.3 ml of 30 µg/ml recombinant human fibronectin fragment CH-296 at room temperature for 2 hours or overnight at 4° C. When different sized non-tissue culture plates were used, reagents were used proportionally. The CH-296 solution was removed, followed by incubation with 2% human serum albumin (HSA) in phoshate buffered saline (PBS) for 30 min at room temperature, followed by washing once with PBS. $5 \times 10^5$ B cells, which were prepared for retroviral transduction were plated in 0.25 mil RPMI without FCS and L-cells and mixed with 025 ml of thawed retroviral supernatant. For the Bcl-6 Bcl-XL double transduction 125 µl of Bcl-6-IRES-NGFR (or IRES-YFP) (Shvarts A, et al. Genes Dev., 2002) and 125 µl of Bcl-XL-IRES-GFP (provided by S. Korsmeyer, Howard Hughes Medical Institute, Childrens Hospital, Boston, USA) were mixed and added to the ells. The culture was subsequently centrifuged at 1800 rpm at 25° C. for 60 minutes and incubated for 6 hours at 37° C. Next 0.25 ml of supernatant was removed and 0.25 ml of fresh retroviral supernatant was added. The culture was again centrifuged at 1800 rpm at 25° C. for 60 minutes and incubated at 37° C. overnight. The next morning cells were transferred to 24 wells tissue culture treated plate (Costar) and cultured for 3-5 days under normal conditions in the presence of human IL-4 (50 ng/ml) or mouse IL-21 (50 ng/ml, R&D, Minneapolis, Minn., USA). Transduction efficiency was determined by antibody staining of a truncated, signaling incompetent mutant of Nerve Growth Factor Receptor (ANGFR, provided by C. Bonini, St. Raphael Hospital, Milan, Italy) or (co) expression of OFP and or YFP. The cells containing the transgene(s) of interest are then selected for further experiments.

Flowcytometry

Antibodies against the human molecules IgD, IgG, CD3, CD19, CD20, CD27, CD38, CD40, CD45, CD56, CD70, CD80, CD86, HLA-DR (BD) directly labeled with FITC, PE, PERCP, PE-Cy5, APC or APC-Cy7 and IgM, kappa light chain, lambda light chain, CD 138, directly labeled with PE (DAKO) were used for flowcytometry analysis. Stained cells were analyzed using a LSRII (BD) and FACS data was processed with Flow Jo computer software (Tree Star, Inc).

Proliferation Experiment

Naïve and memory B cells were isolated from fresh PBMC on the FACSAria: Naïve B cells: CD19-Pe-Cy7 pos, CD27-APC neg, IgD-PE pos Memory B cells: CD19-Pe-Cy7 pos, CD27-APC pos, IgD-PE neg, IgA-FITC neg Cells were washed in PBS and resuspended in 0.5 ml RPMI (37° C.) without FCS. An equal amount of IMDM containing 2 µM Carboxyfluorescein succinimidyl ester (CFSE) was added to the cell mixture and incubated for 7 min at 37° C. Up labeling of the cells was stopped by washing the cell with cold FCS. Cells were resuspended in 500 µl IMDM-8% FCS and cultured with L-cells and in the absence or presence of IL-21. Non-labeled cells were used as control. After 36 bra (immediately before transduction) a proportion of cells was analyzed for their CFSE content. Remaining cells were spin transduced with Bcl-6-IRES-NGFR, cultured for 3 days, and analyzed for their CFSE content using the LSRII. Data was analyzed using FlowJo software (Treestar)

Isolation of antigen specific human B cells using high speed single cell sorting In addition to the memory B cell isolation method described above starting with MBC (i.e. 100 cell/well cultures), human memory B cells can also be incubated with a fluorescent labeled antigen and sorted based on antigen recognition. An example is the isolation of B cells that bind phycoerythrin (PE) labeled Tetanus Toxoid (provided by A. Radbruch, Berlin, Germany) (FIG. 4). Cells were cultured at 1 cell/well and checked for TT binding. Notwithstanding that any other labeled antigen can be used.

Determining the B Cell Receptor (BCR) Expression Alter Long Term Culture of Bcl-6 and Bcl-XL Transduced Cells It is known that B cells that differentiate during in vitro culture lose their BCR membrane expression, which is also observed in EBV transformed B cells. Therefore B cells transduced with Bcl-6 and Bcl-XL and cultured in the presence of IL-21 were stained for GFP, NGFR, CD19, Kappa and/or Lambda or IgG or with labeled Tetanus Toxoid. To show the usefulness of the BCR expression we sorted TT-PE (Radbruch) binding cells using the FACSAria (BD) at 1 cell/well in 96-well plates, which were seeded with L-cells and IL-21 containing culture medium. After three weeks Tetanus Toxoid binding of outgrowing clones was checked using the FACS Canto (BD). Therefore cells were harvested and stained in 96-well plates with GFP, NGFR, CD19 and TT-PE.

Development of Bcl-6 and Bcl-XL Double Positive B Cell Lines that Secrete Antibodies B cell lines were created that produces monoclonal antibodies and are 100% Bcl-6 and Bcl-XL double positive. First this was achieved by inducing proliferation and differentiation using IL-21. Meanwhile these cells are transduced with the Bcl-6-IRES-NGFR and Bcl-XL-IRES-GFP retroviruses. The cells are maintained on IL-4 for 3-4 days. The cells that are transduced with either one or both retroviruses then express the transgene and will therefore express the NGFR or GFP protein. The expression of NGFR and/or GFP can be visualized by using the LSRII (BD). If necessary, cells can be transduced again to obtain higher numbers of cells expressing both transgenes. Irrespective of a second transduction the cells that express both transgenes are sorted using the FACS Aria (BD) and cultured at a cell density ranging from 10-500 cells/well in 96-well plates in the presence of IL-21 and 2500 to 5000 L-cells/well. These mini-bulk-cultures (MBC) secrete relatively large amounts of antibody in the culture supernatant already at day 5 which then can be used for screening purposes. Screening can be based on techniques available for the antigen of interest e.g. ELISA/EIA/RIA, Western blot or direct functional assays like neutralization of cytokine blocking experiments. After screening and selection of MBC that recognize the antigen of interest (TT and RSV in our experiments), cells are subcloned at 0.5-1 cell/well in 96 well in the presence of IL-21. Subcloning normally takes 2-3 weeks and can be performed by limiting dilution (LD) cultures or single cell sorting using flow cytometry (FACSAria).

RSV A-2 Virus Stock and HEp2 cNäiveell Line

The RSV A-2 virus (kindly provided by G. van Bleek, WKZ, Utrecht) and HEp2 cell line (Clinical Laboratory, AMC, Amsterdam), were cultured in large quantities and frozen in liquid nitrogen.

The adherent HEp2 cell line was cultured in normal medium in T175 Falcon bottles before aliquots were frozen.

To obtain a high titer RSV stock, HEp2 cells were seeded and cultured to reach 50-60% confluence. The original RSV stock was added (1/20 dilution total volume 5 ml) for 45' at RT on the HEp2 cells. 15 ml fresh medium was added and cells were left o/n at 37° C., 5% $CO_2$ with the coverlid open. The next morning culture supernatant was carefully removed and 15 ml medium containing 1% FCS was added. Cells were left for 24 to 36 hours at 37° C., 5% $CO_2$ with the coverlid closed. When RSV induced syncytia were clearly visible and the majority of the syncytia were still intact, the medium was harvested, filtered (0.22 µm) and spin at 1450 rpm at RT before samples were snap frozen and stored in liquid nitrogen. A second harvest can be obtained by immediately adding new medium containing 1% PCS and freezing this batch 4-6 hours later.

RSV Lysate for ELISA

HEp2 cells that were infected with RSV A-2 to obtain virus stocks were used to isolate RSV proteins. First cell were carefully washed with PBS and trypsinized. Trypsin (Gibco) was washed away and the cell pellet was lysed with 1% octylglucoside (cell pellet of one T175 flask was treated with 2 ml octylglucoside). Suspension was homogenized with syringe and needle (10 times up and down), incubated for 1 hour on ice and then dialyzed against 2 L TBS buffer pH 7.4, o/n at 4° C. Supernatant was obtained after spin down of cell debris. The protein content was determined at 3.6 mg/ml and was used at 20 µg/ml (50 µl) in ELISAs.

Determining TCID50 and PFU of RSV Stocks

To determine the TCID50, $10^4$ HEp2 were seeded in 96 well plates and infected with a 2 or 10 step serial dilution of RSV virus in 4-plo. 2-3 days later culture supernatant were removed and cells were fixed with 80% acetone for 10' at RT. After removal of the acetone, the fixed cell layer was dried and kept at 4° C. or frozen at −20° C. To stain RSV HEp2 cells the plates were first blocked with 5% milkpower in PBS 0.1% Tween 20. Then plates were washed 3 times before being incubated for 3-5 hours at 37° C. with polyclonal goat anti-RSV-HRP (1:500, Biodesign, Saco, Me., US) and washed extensively. Next the wells were incubated with AEC substrate for 30' at RT. Infected foci stain red and can be observed by eye using a light microscope and can be counted. Standard Excel software was used to determine the $TCID_{50}$.

To determine the amount of plaque forming units (PFU) of the virus, $1 \times 10^5$/ml of HEp2 cells in 24 well plates were incubated with 10-fold serial dilutions ($10^{-3}$-$10^{-7}$) of RSV virus stock in medium with 1% FCS at 37° C. for 45' (200 µl) before cells and virus were covered with 0.5 ml hand warm 0.25% seaplaque agar (Biozyme). The agarose layer prevents the spreading of the virus to uninfected cells through the culture medium. Thereby the virus can infect only neighboring cells, which eventually are killed by the virus creating plaques in the monolayer of HEp2 cells. Those plaques can best be visualized by staining the fixed cells (96% ethanol-100% acetic acid-10% formalin 6:2:1) with 1% crystal violet solution. Plaques are counted (by at least two different individuals) and the PFU value can be determined.

Selection of Respiratory Syncytial Virus (RSV) Neutralizing Antibodies

To obtain anti-respiratory syncytial virus (RSV) B cell clones, peripheral blood cells (PBMC) from two donors were isolated from bloodbank derived buffy coats (donor B62 and B63). Before sorting $CD19^{pos}IgM^{neg}IgD^{neg}CD27^{pos}$) cells using the FACSAria (BD)(FIG. 1), CD22+ cells were isolated using MACS beads and columns (Miltenyi). Only if mentioned differently, cells were cultured with L-cells. Cells were cultured for 36 hours in the presence IL-21 before being transduced with Bcl-6-IRES-NGFR only. After 12 h cells were harvested and cultured for 3 days in the presence of IL-4 before NGFR expressing cells were sorted using MACS beads (Miltenyi) and immediately transduced with Bcl-XL-IRES-GFP. The B cells that did not bind to the MACS beads were washed and transduced with Bcl-6 and Bcl-XL at the same time. After 12 h cells were harvested, pooled and cultured for 3 days in the presence of IL-4 before being sorted on GFP and NGFR expression on the FACSAria. Cells were washed and cultured at 100 cell/well density in 96 well plates (Costar) in the presence of IL-21.

The double transduced Bcl-6 and Bcl-XL B cell cultures were screened for RSV binding using a RSV-infected HEp2 cell lysate ELISA and were tested in parallel using a RSV microneutralization experiment. In brief, $10^4$ HEp2 cells are seeded in flat bottom 96 well plates (Costar) in complete medium. The next day medium is replaced for 1 h at RT with the mixture of RSV virus and cell culture supernatant which have been pre-incubated for 30 min at 37° C. The total volume is 25 µl and the RSV end concentration is 0.1 MOI. After 1 h the virus supernatant mixture is 9 times diluted with PBS and replaced with 100 µl IMDM/5% FCS. After 2 days cells are fixed with 80% acetone and stained with polyclonal anti-RSV-HRP (Biodesign). Using $H_2O_2$ and AEC cells infected with RSV develop a red stain. Using light microscopy infected cells can be observed and counted if necessary. As a control for RSV neutralization a goat polyclonal anti-RSV (Abcam, Cambridge, Mass.) is used.

RT-PCR and Cloning of VH and VL Regions

Total RNA was isolated from ~$5 \times 10^5$ B cells with the RNeasy® mini kit (Qiagen, Venlo, The Netherlands). 250 ng of total RNA was reverse transcribed in a volume of 20 µl containing 1× first strand buffer, 500 µM dNTP, 250 ng random hexamers, 5 mM DTT, 40 U RNasin (Promega) and 200 U SuperScript III RT (Invitrogen). The cDNA was diluted 10× in Ultrapure water and 2.5 µl of cDNA was subjected to PCR in a 50 µl solution containing 20 mM Tris-HCL, 50 mM KCL, 2.5 mM MgCl2, 250 µM dNTP, 1 U AmpliTaq Gold DNA polymerase (Applied Biosystems Inc.), and 25 pmol of each primer. PCR conditions were as follows: 8 min denaturing step at 96° C. followed by 35 cycles of 30 sec at 96° C., 30 sec at 60° C., 1 min at 72° C., and a final 10 min extension at 72° C.

PCR products were run on agarose gels, purified and cloned into the pCR2.1 TA cloning vector according to manufacturers' recommendations. Sequence analysis was performed using BigDye Terminator chemistry (Applied Biosystems Inc.) and Vector-NTI software (Invitrogen).

To rule out reverse transcriptase and/or DNA polymerase induced mutations, several independent cDNA conversions and PCR reactions were performed and individually cloned and sequence analyzed. Consensus sequences were determined with Vector-NTI Contig Express software.

For recombinant protein antibody expression in 293T cells full length heavy and light chain constructs were generated in pCDNA3.1(+)Zeo (Invitrogen). The heavy chain expression vector was constructed by PCR amplification of the heavy chain leader sequence and VH region of clone D25 introducing a 5'-NheI site and a 3'-XhoI site. The IgG1 constant region (CH1-hinge-CH2-CH3) was amplified from the same cDNA while introducing a 5'-XhoI and a 3'-NotI site. The full length heavy chain expression vector was obtained by three point ligation into NheI/NotI digested pCDNA3.1(+)Zeo. The full length light chain expression construct was generated by PCR amplification of the light chain leader sequence, VL region and light chain constant region with primers introducing a 5'-NheI and 3'-NotI site. The latter product was cloned into NheI/NotI digested pCDNA3.1(+)Zeo to obtain a full length light chain expression vector.

Sequence Analysis was Performed to Confirm Correctness of the Expression Constructs.

Transient double transfection (Fugene-6, Roche, Germany or Lipofectamine LTX, Invitrogen) of 293T cells with both heavy and light chain expression vectors was performed to produce recombinant monoclonal antibody. A FACS staining with the resulting culture supernatant (48 hours) on RSV infected Hep2 cells was performed to show functional binding of the antibody to the RSV F protein. The oligonucleotides used for PCR amplifications were:

```
VH regions:
VH1-For
                                            (SEQ ID NO: 11)
5'-AAATCGATACCACCATGGACTGGACCTGGAGG-3'

VH1B-For
                                            (SEQ ID NO: 12)
5'-AAATCGATACCACCATGGACTGGACCTGCAGM-3'

VH2A-For
                                            (SEQ ID NO: 13)
5'-AAATCGATACCACCATGGACACACTTTGCTMCAC-3'

VH2B-For
                                            (SEQ ID NO: 14)
5'-AAATCGATACCACCATGGACATACTTTGTTCCAAC-3'

VH3-For
                                            (SEQ ID NO: 15)
5'-AAATCGATACCACCATGGAGTTTGGGCTGAGC-3'

VH3B-For
                                            (SEQ ID NO: 16)
5'-AAATCGATACCACCATGGARYTKKGRCTBHGC-3'

VH4-For
                                            (SEQ ID NO: 17)
5'-AAATCGATACCACCATGAAACACCTGTGGTTCTT-3'

VH5-For
                                            (SEQ ID NO: 18)
5'-AAATCGATACCACCATGGGGTCAACCGCCATC-3'

VH6-For
                                            (SEQ ID NO: 19)
5'-AAATCGATACCACCATGTCTGTCTCCTTCCTC-3'

Cgamma-Rev
                                            (SEQ ID NO: 20)
5'-GGGTCTAGACAGGCAGCCCAGGGCCGCTGTGC-3'

Vkappa regions:
Vk1-For
                                            (SEQ ID NO: 21)
5'-AAATCGATACCACCATGGACATGAGGGTCCCY-3'

Vk1B-For
                                            (SEQ ID NO: 22)
5'-AAATCGATACCACCATGGACATGAGRGTCCYY-3'

Vk2-For
                                            (SEQ ID NO: 23)
5'-AAATCGATACCACCATGAGGCTCCCTGCTCAG-3'

Vk3-For
                                            (SEQ ID NO: 24)
5'-AAATCGATACCACCATGGAARCCCCAGCGCA-3'

Vk4-For
                                            (SEQ ID NO: 25)
5'-AAATCGATACCACCATGGTGTTGCAGACCCAG-3'

Ck-Rev
                                            (SEQ ID NO: 26)
5'-GATCGCGGCCGCTTATCAACACTCTCCCCTGTTGAAGCTCTT-3'

Vlambda regions:
V11aecb
                                            (SEQ ID NO: 27)
5'-AAATCGATACCACCATGGCCTGGTCCCCTCTCCTCC-3' v11g
                                            (SEQ ID NO: 28)
5'-AAATCGATACCACCATGGCCGGCTTCCCTCTCCTCC-3'

V12/10
                                            (SEQ ID NO: 29)
5'-AAATCGATACCACCATGGCCTGGGCTCTGCTCCTCC-3'

V13jpah
                                            (SEQ ID NO: 30)
5'-AAATCGATACCACCATGGCCTGGACCGCTCTCCTGC-3'

V15/7
                                            (SEQ ID NO: 31)
5'-AAATCGATACCACCATGGCCTGGACTCCTCTCCTTC-3'

V16/9
                                            (SEQ ID NO: 32)
5'-AAATCGATACCACCATGGCCTGGGCTCCTCTCCTTC-3'

V13rm
                                            (SEQ ID NO: 33)
5'-AAATCGATACCACCATGGCCTGGATCCCTCTCCTCC-3'

V131
                                            (SEQ ID NO: 34)
5'-AAATCGATACCACCATGGCCTGGACCCCTCTCTGGC-3'

V13e
                                            (SEQ ID NO: 35)
5'-AAATCGATACCACCATGGCCTGGGCCACACTCCTGC-3'

V14c
                                            (SEQ ID NO: 36)
5'-AAATCGATACCACCATGGCCTGGGTCTCCTTCTACC-3'

V18a
                                            (SEQ ID NO: 37)
5'-AAATCGATACCACCATGGCCTGGATGATGCTTCTCC-3'

C12/7
                                            (SEQ ID NO: 38)
5'-GATCGCGGCCGCTTATCAWGARCATTCTGYAGGGGCCACTG-3'
```

The oligonucleotides used for expression vector constructions were:

```
Heavy chain expression vector:
VH1-L-NheI:
                                            (SEQ ID NO: 39)
5'-GCGGCTAGCCACCATGGACTGGACCTGGAGG-3'

JH4/5-XhoI:
                                            (SEQ ID NO: 40)
5'-GCGCTCGAGACGGTGACCAGGGTTCCCTG-3'

CHfw-XhoI:
                                            (SEQ ID NO: 41)
5'-CGCGCTCGAGTGCCTCCACCAAGGGCCCATCGGTC-3'

CHrev-NotI:
                                            (SEQ ID NO: 42)
5'-GATCGCGGCCGCTTATCATTTACCCGGRGACAGGGAGAGGC-3'

Light chain expression vector;
VK1-L-NheI:
                                            (SEQ ID NO: 43)
5'-GCGGCTAGCCACCATGGACATGAGGGTCCCY-3'

CK-NotI:
                                            (SEQ ID NO: 44)
5'-GATCGCGGCCGCTTATCAACACTCTCCCCTGTTGAAGCTCTT-3'
```

EBV RT-PCR

To test if the strong proliferative response was related to the presence of EBV, an EBV RT-PCR was performed. The RT procedure is described above. The PCR conditions were as follows: a 7-minute denaturing step at 94° C. followed by 30 cycles of 30 s at 94° C., 30 s at 62° C. (HPRT1), 52° C. (LMP-1) and 58° C. (EBNA1/2) and 30 s at 72° C., and a final 7-minute extension at 72° C. The oligonucleotides used for RT-PCR were as follows: HPRT1 forward (5'-TATG- GACAGGACTGAACGTCTTOC-3') (SEQ ID NO: 45) and HPRT1 reverse (5'-GACACAAACATGATTCAAATC-CCTGA-3') (SEQ ID NO: 46); LMP-I forward: (5'-GC-GACICToCGOGAAATGAT-3') (SEQ ID NO: 47) and LMP-I reverse (5'-GACATGGTAATGCCTAGAAG-3') (SEQ ID NO: 48); EBNA1/2 forward (5'-AG-CAAGAAGAGOAGGTGOTAAG-3') (SEQ ID NO: 49) and EBNA1/2 reverse (5'-GGCTCAAAGT-GOTCTCTAATGC-3') (SEQ ID NO: 50).

In addition to the RT-PCR we performed a PCR directly on cell pellet and supernatant DNA that was isolated using the QIAmp isolation kit (Qiagen).

Example 1

Results
B Cell Phenotype

The use of human memory B cells as the platform to isolate therapeutics medicines relies on the ability to grow and test these cells for a relative long period of time. Human B cells can be cultured and maintained in a laboratory setting however not long enough to expand, select and clone single B cell lines against an antigen of interest. We developed immortalization techniques based on genetic modifications of human B cells. We studied downstream targets of STAT5. One target besides others is Bcl-6. Bcl-6 inhibits differentiation of B cells to plasma cells that are arrested in proliferation. Overexpression of Bcl-6 keeps BLIMP1 in balance, a transcription factor which expression is strongly enhanced by stimulating B cells with IL-21 (works via STAT3). BLIMP1 is necessary to induce the development of Ig producing cells (CD20-CD38+) whereas Bcl-6 can prevent this (cells maintain CD20 expression, the so-called germinal center phenotype).

To study the possible skewing of certain cell populations within the B cell compartment, CFSE labeling prior to stimulation of fresh memory and naïve human B cells revealed that all cells start dividing and that all populations of B cells are equally transduced (FIG. 2). Shown are memory B cells transduced with Bcl-6 and cultured in the presence of IL-21 and IL-4. Naïve B cells were transduced at a lower level and division rates were lower at 36 hrs but were identical to memory B cells after another 3 days of culture (data not shown).

Next we show that Bcl-6, together with Bcl-XL (anti-apoptotic downstream target of STAT5), CD40L signaling and in the presence of IL-21, maintain human IgG memory B cells in the CD20+CD38dull phenotype for long periods of time (>3 months) (FIG. 3). In addition, the Bcl-6 Bcl-XL B cells have a phenotype corresponding to activated B cells (see Table 1, exemplified by FACS staining of 3 T+B cell clones), since these cells have high expression of CD80, CD86 and HLA-DR.
determined on three different Bcl-6 Bcl-XL B cell clones cultured with IL-21 and CD40L signaling

| staining | result |
| --- | --- |
| CD2 | neg |
| CD5 | neg |
| CD7 | neg |
| CD10 | pos |
| CD20 | pos |
| CD21 | pos |
| CD22 | pos |
| CD23 | neg/5% pos |
| CD24 | neg |
| CD25 | pos |
| CD27 | neg/low |
| CD28 | neg |
| CD30 | pos (56-74%) |
| CD38 | pos/intermediate |
| CD40 | pos |
| CD44 | pos |
| CD45 | pos |
| CD45RA | pos/high |
| CD69 | neg |
| CD70 | pos |
| CD71 | pos |
| CD73 | neg |
| CD80 | pos/high |
| CD86 | pos |
| CD95 | pos/high |
| CD126 | neg |
| CD132 (common gamma) | pos |
| CD138 | neg/2% pos |
| CD154 (CD40L) | 8% pos |
| ICOSL | pos |
| IgM | neg |
| IgG | pos |
| HLA-DR | pos (high) |
| Kappa | pos/neg |
| Lambda | pos/neg |
| IL21-R | pos |

Antibody Membrane Expression

The Bcl-6 Bcl-XL transduced, EBV negative cells remained BCR expression positive as determined by antigen binding or Kappa and Lambda staining (FIGS. 3 and 4). Hence, such cells are particularly suitable for isolating and/or screening after a long period of culture for a desired specificity, for instance using labeled antigen, because such cells will bind said labeled antigen with their BCR. This was confirmed by single cell sorting of Bcl-6 and Bcl-XL double transduced B cells that bind PE labeled TT using the FACSAria. After three weeks single cell sorted clones were stained with appropriate markers and TT-PE in 96 well plates and measured for binding in the FACS Canto (BD) (FIG. 4). In conclusion, in cases where the presence of a B cell receptor on B cells is desired, such as for instance in screening assays, the B cells are preferably transduced with Bcl-6 and Bcl-XL and not infected with EBV.
Cell Division and Growth Curves Bcl-6 Bcl-XL transduced B cells divide on average 0.6 times per day. Division rate varies between donors and cell density of the cultures (FIG. 5 left side). The anti-RSV clone D125 had a division rate of 0.47 times per day (FIG. 5 right side). Cells can be grown at densities below 1 cell/96 well for cloning purposes.
Antibody Secretion of Bcl-6 Bcl-XL B Cells The Bcl-6 Bcl-XL transduced B cells secrete on average one µg/ml of antibodies, which is enough to grow quantities necessary for pre-clinical tests (FIG. 6). Surprisingly the D25 anti-RSV clone produced three times more antibodies compared to the other cell lines tested.
Determine EBV Content EBV RT-PCR on mRNA of Bcl-6 Bcl-XL cell lines that were cultured with IL-21 and CD40L signaling. In the cell lines obtained with this immortalization technique no EBV gene transcript have ever been detected (data not shown).
Selection Procedure Due to the stability in growth and expression of the BCR, these cells are well suited to isolate antigen-specific B cells. It gave us the opportunity to use several different selection and cloning procedures. One is to immediately obtain antigen specific cells after introduction of Bcl-6 and Bcl-XL by FACS or Magnetic Bead sorting using labeled antigen of interest thereby enhancing the probability of generating multiple antigen-specific B cell clones. Another option is to grow purified, bulk Bcl-6 Bcl-XL transduced memory (or any other) B cells at low cell densities (for example 100 cells/well). Supernatants from these 100 c/w cultures can be collected and tested for their specificity. 100 cell/well cultures that are found positive for antigen recognition, are then subcloned by limiting dilution cultures to obtain monoclonal cell lines. Using both methods we could isolate over 40 Tetanus Toxoid (TT) recognizing B cell clones. Thus these clones were either selected on TT binding to the BCR on the FACSAria or they were selected by ELISA screening of series of cultures till the single anti-Tr monoclonal cell line was isolated (not shown).

Selection of RSV Neutralizing Antibodies

From donor B63, 25 100 cell/well cultures completely blocked RSV infection and replication. D10, one of the neutralizing 100 cell/well cultures produced a strong anti-RSV antibody which we cloned by limiting dilution culture. One of the monoclonal antibodies, D25 was used to continue studies. D25, a monoclonal antibody with an IgG1 heavy chain, as determined by commercial ELISA (Sanquin, Amsterdam, not shown) and a Kappa light chain (FIG. 7), very efficiently blocked RSV infection with an $IC_{50}$ value of between 0.5 and 1.5 ng/ml (±10 pM) whereas the $IC_{50}$ of the standard anti-RSV antibody used in the clinic (palivizumab developed by Medimmune) is 0.453 µg/ml (3.02 nM) (H. Wu et al. 2005 J. Mol. Biol, and A. Mejias et al. 2005 Antimicrob. Agents Chemother.) (FIG. 8).

Antigen Recognition

In addition to the neutralization experiments, the binding of D25 to RSV infected HEp2 cells was determined. HEp2 cell were infected using the regular virus production protocol. HEp2 cells infected with RSV were trypsinized and incubated with 25-50 µl culture supernatant. Cells were washed and stained with mouse-anti-human IgG-PE (BD or Jackson) to detect binding of the D25 antibody to the infected cells. The r-Biopharm ELISA control antibody was used as an internal control. Shown in FIG. 9a is the binding of D25 to intact, RSV infected HEp2 cells.

Since the RSV envelope (membrane) proteins exist of two proteins namely the 0 and F-protein, the binding of D25 was tested against cells infected with the VSV virus pseudotyped with either no or the RSV F or RSV G protein (kindly provided by John K Rose). As shown in FIG. 9b, D25 bound strongly to EIA cells infected with the VSV-F protein. In an attempt to study the epitope recognized by D25 versus palivizumab, VSV-F protein infected EL-4 cells were incubated with increasing amounts of D25 or palivizumab. Cells were washed and stained with a mixture of 3 mouse-anti-RSV-F antibodies (Dako). In contrast to Palivizumab that showed competition for the binding to infected VSV-F cells with the mouse-anti-RSV-F antibody, D25 binding was not affected (data not shown).

FIG. 9c shows the binding of Palivizumab (Synagis) and D25 in a concentration dependent manner to infected HEp2 cells. Since both antibodies bind 1 to 1 to their target protein there is no difference in binding to infected HEp2 cells.

Frequency of RSV Antigen Binding Vs Neutralizing Clones

We calculated that the frequency of antigen specific memory B cells that bind RSV was 17% and the frequency of antigen specific cells that neutralize RSV was 6%, as determined for donor B63. D25 binds to a conformational epitope that is different than the epitope recognized by palivizumab. This is illustrated in FIG. 10 in which D25 does not bind to denatured, linear epitopes presented by lysed RSV infected cell lysate coated on ELISA plates while palivizumab does bind to denatured (F) protein.

Isolation and Purification of Antibody Fragments

From several B cell lines including the highly RSV neutralizing clone D25 we were able to grow volumes as much as 500 ml. These culture supernatants contain at least 2 µg/ml, therefore we should be able to obtain enough purified antibody to perform pre-clinical (animal) studies. The purification is performed using Montage Antigen Purification Kit (Millipore, Billerica, Mass., USA) and HiTrap Protein A HP columns (GE Healthsare, Diegem, Belgium).

In addition, 293T cells were transfected with the heavy and light chain of D25 that were subcloned in pCDA3.1 protein expression vectors using lipofectamine LTX (Invitrogen). The amount of IgG that were present in the supernatant was approximately 22 µg/ml (total volume 50 ml). This antibody derived from the cloned nucleotide sequence of the antibody expressed by the D25 B cell line did also recognized infected HEp2 cells (data not shown).

Antibody Sequence

FIG. 11a shows the heavy and light chain nucleotide and amino acid sequence of the B63D10-D25 clone. By using standard RT-PCR and antibody specific primers, the heavy (Vhl-69) and light (VkI O8/O18) chain sequences were determined. The whole antibody sequence was cloned by using TOPO vectors and after sequence control, subcloned into the pCDNA3.1 mammalian protein expression vector (Invitrogen). FIGS. 11b and 11c depict the VH and VL4 chain of the clone, Astricks indicate mutations compared to the germline sequence of the Vhl-69 that must have occurred during affinity maturation and further B cell selection.

To summarize, we here show the isolation, characterization and long-term culture of human memory B cells using the transgenes Bcl-6 and Bcl-XL. They give us the tool necessary to isolate antibodies with unique properties, like the anti-RSV monoclonal antibody B63D10-B25. Since the B cells are from a human origin, they can readily be deployed as a therapeutic medicine.

Example 2

The D25 heavy and light chain were cloned into standard expression vectors as described before (p44 'antibody sequence'). To create an expression construct that allows for maximum protein expression the D25 heavy and light chain sequences were codon optimized by GENEART (Regensburg, Germany). In this procedure additional restriction sites were created to simplify future cloning procedures but most importantly nucleotide codons that translate into amino acid sequences were optimized for maximum translation into protein. Thus the nucleotide sequence was optimized but the amino acid sequence remained unchanged. Shown in EXAMPLE 4 is the neutralizing capacity of purified B cell supernatant derived D25, recombinant D25 and GENEART optimized D25. All efficiently neutralize RSV.

The GENEART modifications compared to the original D25 sequence are depicted in FIG. 12.

Example 3

Next to the in vitro RSV neutralization experiments we tested the D25 monoclonal antibody in in vivo models. The models that have been described for in vivo anti-RSV tests are BALB/c mice and cotton rats (*Sigmodon hispidus*) (Mejias A et al, Antimicrobial Agents and chemotherapy 2004; p 1811, Johnson S et al., JID 1997; p 1215 and Wu H et al, JMB 2007:p 652). The BALB/c mouse model is clearly the weakest model but since the cotton rats are difficult to get and maintain, we first set up D25 tests in BALB/o mice.
Protocol: RSV Specific Antibodies in BALB/c, Day 5
Experimental Design:
Day −1. I.P. injection 100 µl antibodies
Day 0, I.N infection 1×10$^7$ pfu RSV A2 in 50 µl
Day 1 to 5, check general well being and weigh mice
Day 5, autopsy, collect BAL, blood and lungs
Draw blood via vena puncture
Collect 2.0 ml BAL via trachea canule
Collect lungs
Immediately start TCID$_{50}$ on BAL material (1 ml)
Freeze 1 ml BAL material (ELISA cytokine/RT-PCR) −80 C
Perform TCID$_{50}$ on prepared long material (1 ml)
Freeze 1 ml long material (ELISA cytokine/RT-PCR) −80 C
Collect/spin blood for hIgG ELISA on serum en store at −80 C
The results are shown in FIG. 13:

(A) One day before RSV challenge (1×10$^7$ RSV-A2 particles) by nasal spray, animals were IP injected with different amounts of Synagis (MedImmune), purified D25 or an IgG1 ctrl antibody (Eureka) (Table 3). (FIG. 13B) Human IgG levels were determined in mice sera from day 5 and the drop in antibody serum levels in 5 days; Table 4 shows an overview of the half-life values. FIG. 13D depicts virus titers found in lung lavages (BAL) at day 5 in treated and untreated animals whereas FIG. 13E depicts T and B cell numbers in peripheral blood of treated and untreated mice. FIGS. 13F-13J show the histology of the lungs with bronchi and infiltration of (normally mainly eosinophils) untreated and treated animals.
Conclusion/Result:

An estimate of the D25 half-live is 5 to 9 days based on the (linear) calculation that 60 and 30 µg of antibody was injected on day 0 (2 and 1 mg/kg respectively) and at day 5 33 or 16 µg was detected (total volume of mice 1,5). When we started with 0.5 mg/kg injection per animal on d0 then Ig levels drop from 15 µg to 11 µg on day 5, which would indicate a 9 day half life (Table 4).

TABLE 4

| mg/kg | total administered d0 (µg) | detected on d5 (µg) | half-life (days) |
|---|---|---|---|
| 2.0 | 60 | 33 | 5.6 |
| 1.0 | 30 | 16 | 5.4 |
| 0.5 | 15 | 11 | 9.4 |

Virus titer as determined TCID50 assay shows that in control animals 1×10$^4$, PFU can be detected whereas no virus was detected in the Synagis (2 mg/kg) or D25 (2, 1 and 0.5 mg/kg) treated animals.

Animals treated with Synagis or D25 maintain higher % of peripheral CD4 T cells and B220 B cells. Animals treated with Synagis (2 mg/kg) have lower % of CD4 T cells compared to D25 treated animals. Although this may not be significant it is important to note that animals treat with a low dose of D25 (1 and 0.5 mg/kg) maintain high levels of B and T cells when compared to control treated animals.

Although the histology data (FIGS. 13F-13J) are not quantitative it is clear that Synagis and D25 reduce influx of immune cells into the lungs and around the bronchi compared to control. When D25 and Synagis are compared, then D25 treated animals seem to have less cellular infiltration into the lungs and around the bronchi.

To test D25 in the Cotton rats, experiments are set up to compare animals pre-treated with Synagis and D25 before challenge with the RSV-X virus at the NVI (Bilthoven, Netherlands).

Example 4

In addition to B63-D10-D25, we isolated three new potent RSV neutralizing antibodies (AM14, AM16 and AM23) from the same donor (B63). 100 cell per well bulk B cell cultures that were originally selected for RSV neutralization and were frozen and stored in liquid nitrogen, were thawed and culture supernatant was tested for binding to RSV infected HEp2 cells. We tested for binding to infected Hep2 cells since that is a marker for antibody recognition of native, oligomeric RSV membrane proteins like F and G protein and may serve as a good predictor for neutralization. When binding was detected, cells were single cell cultured and screened for binding to obtain clones. All three antibodies were cloned into the GENEART vector that was originally constructed for D25. In addition like D25 all recognize the RSV-F protein (not shown). After cloning and expression in 293T cells recombinant protein was purified (nucleotide and amino acid sequences are depicted in FIGS. 14A, B and C). Antibodies were tested for neutralization against several primary RSV isolates on Vero and IEp2 cells (FIG. 15). All three antibodies are of the IgG1 isotype. AM14 has a Kappa light chain, while AM16 and AM23 have a Lambda light chain. All three antibodies, like D25, contain somatic hypermutations in their antibody variable domains suggesting that they in vivo have undergone affinity maturation during a germinal center reaction, a process that creates unique antibody sequences.

The results are shown in FIGS. 15A and 15B: RS virus neutralization assay with purified B cell line supernatant derived D25 (sD25), recombinant purified D25 (rD25), recombinant GENEART codon optimized D25 (rD25 GA), AM14, AM16, AM23 (all purified recombinant protein) and Synagis. Virus antibody neutralization was tested on two different cell lines (FIG. 15A) Vero and (FIG. 15B) Hep2 cells with different antibodies: A2 (panel A), X (panel B) and 2006/1 (panel C) are RSV subtype A while virus Z (panel D) and 2007-2 (panel E) are subtype B. 100TCID50 of each virus was added to serial antibody dilutions in DMEM/1% FCS and incubated for 1 hour at 37 degree before 100 ul Vero or HEp2 cells (1×10$^6$/ml) were added. Virus antibody mixture was not washed away. After three days supernatant was removed and cells were fixed with 80% acetone for 10' at RT. After removal of the acetone, the fixed cell layer was dried and kept at 4° C. or frozen at −20° C. To stain RSV infected HEp2 cells, plates were first blocked with 5% milkpower in PBS 0.1% Tween 20, then plates were washed 3 times before being incubated for 3-5 hours at 37° C. with polyclonal goat anti-RSV-HRP (1:500, Biodesign, Saco, Me., US) and washed extensively. Subsequently all wells were incubated with ABC substrate for 30' at RT. Infected foci stain red and can be observed by eye using a light microscope and can be counted.
Result/Conclusion All antibodies neutralize the RSV A and B strains (Table 5). In general the different D25 antibodies neutralize the RSV viruses efficiently, although minor inter-experimental variations can be seen. AM14 is just as potent as D25 while AM16 is just as potent as Synagis. AM23 however does neutralize the RSV A strains very efficient, while it is less potent in neutralizing RSV B strains, although still comparable to Synagis.

TABLE 5

| Cell line used | RSV subtype | IC50 values (ng/ml) | | | | | |
|---|---|---|---|---|---|---|---|
| | | sD25 | rD25 | rD25 GA | AM14 | AM16 | AM23 |
| Vero | A | 3.4 | 1.6 | 3.2 | 15.2 | 304.3 | 19.4 |
| Vero | B | 9.0 | 0.3 | 1.2 | 1.1 | 126.4 | 168.8 |
| HEp2 | A | 3.3 | 2.1 | 5.3 | 21.5 | 285.6 | 25.0 |
| HEp2 | B | 14.3 | 1.9 | 1.3 | 6.7 | 124.8 | 190.7 |

The IC50 value for each antibody on RS virus subtype A on Vero or HEp2 cells was calculated as the average 50% neutralization on three virus strains (A2, X and 2006-1). The IC50 value for each antibody on RS virus subtype B on Vero or HEp2 cells was calculated as the average 50% neutralization on two virus strains (2007-2 and Z). Each of the neutralizations assays was performed in triplo and repeated twice (also shown in FIG. 15A and B).
sD25 = purified B cell derived culture supernatant
rD25 = purified recombinant D25
rD25 GA = supernatant of 293T cells with GENEART codon optimized recombinant D25

Example 5

Synergistic and Blocking Effects of Anti-RSV Antibodies.

To analyze whether D25, Synagis or the new AM antibody set interfere with each other for recognition of the RSV F protein, we pre-incubated RSV infected HEp2 cells with increasing concentrations of unlabeled antibodies till they reached the plateau of maximum binding. We determine for each antibody the plateau phase in which no increase in binding was detected when the amount of Ig was increased, (not shown). After washing, samples were incubated with a standard dose (3 pmol) of PE labeled D25 or APC labeled Synagis. This dose gives also maximum binding.
Result As shown in FIG. 16 labeled Synagis and D25 show a reduced binding to RSV infected HEp2 cells when these cells were pre-incubated with either unlabeled Synagis or D25. Synagis shows furthermore a slight reduction in binding induced by AM16. D25 binding is strongly blocked by AM23 but on the contrary D25 binding is strongly enhanced after pre-incubation with AM14. That indicates that the epitope recognized by D25 is normally not even fully exposed but exposure is enhanced after binding of AM14 to its native epitope. That demonstrates that these two antibodies can work together and enhance neutralization.

Isolation of human, IgG positive, memory B cells. PBMC isolated from buffy coat using Ficoll density separation (Amersham) were incubated with anti-CD22 magnetic beads before being isolated using MACS columns (Miltenyi). CD22 positive cells were then incubated with antibodies against human CD19, CD27, IgM, IgD and IgA (BD). Cells negative for IgM, IgD and IgA and positive for CD19 and CD27 were sorted using high speed single cell sorting (FACSAria, BD).

FIG. 2

CFSE staining. Fresh human memory B cells were isolated, labeled with CSFE and stimulated for 36 h with IL-21 before being transduced with Bcl-6-IRES-NGFR. Cells were kept an additional 3 days on IL-21 before CFSE content was determined. The CFSE dye is diluted with every cell division.

FIG. 3

An example of human B cells transduced with Bcl-6 and Bcl-XL or Bcl-XL only. Cells were maintained on irradiated L cells expressing CD40L and the cytokine IL-21. Shown on the left is the BCR expression as determined by kappa and lambda staining (93% of the kappa lambda positive cells are of the IgG isotype, not shown). On the right is shown the CD38 expression on the X-axes and CD20 expression on the Y-axes. The $CD38^{dull}CD20^+$ staining indicates memory or germinal center B cells; the $CD38^+CD20^-$ staining indicate plasmablasts.

FIG. 4

Figure 1:
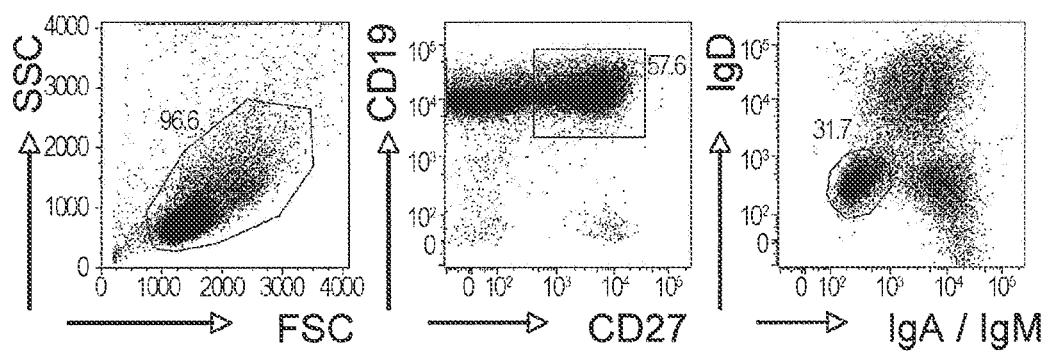
FIG. 1.
Figure 2:
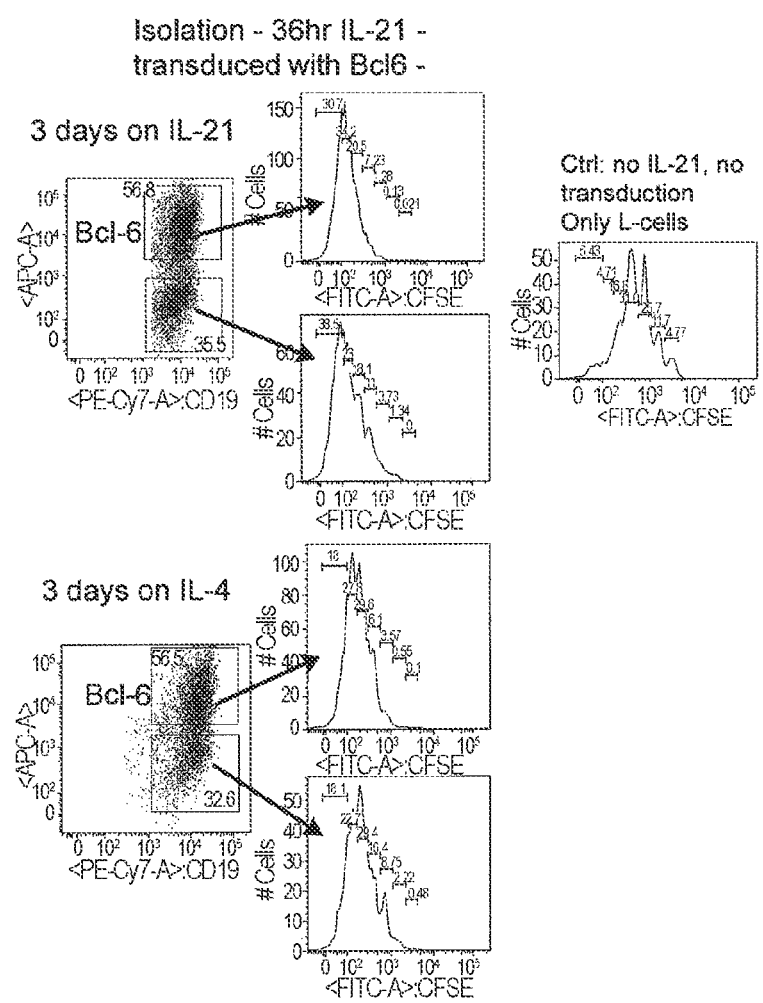
Figure 3:
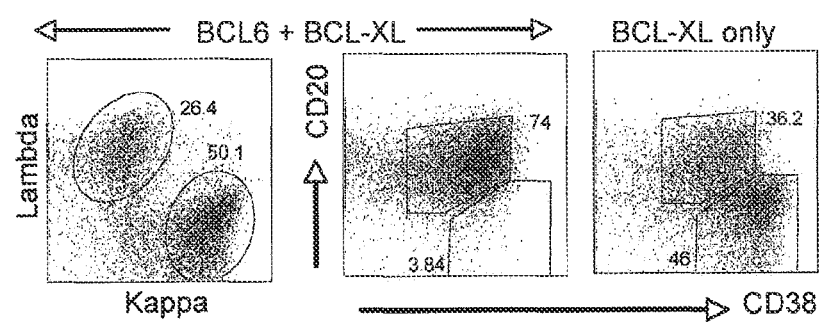
Figure 4:
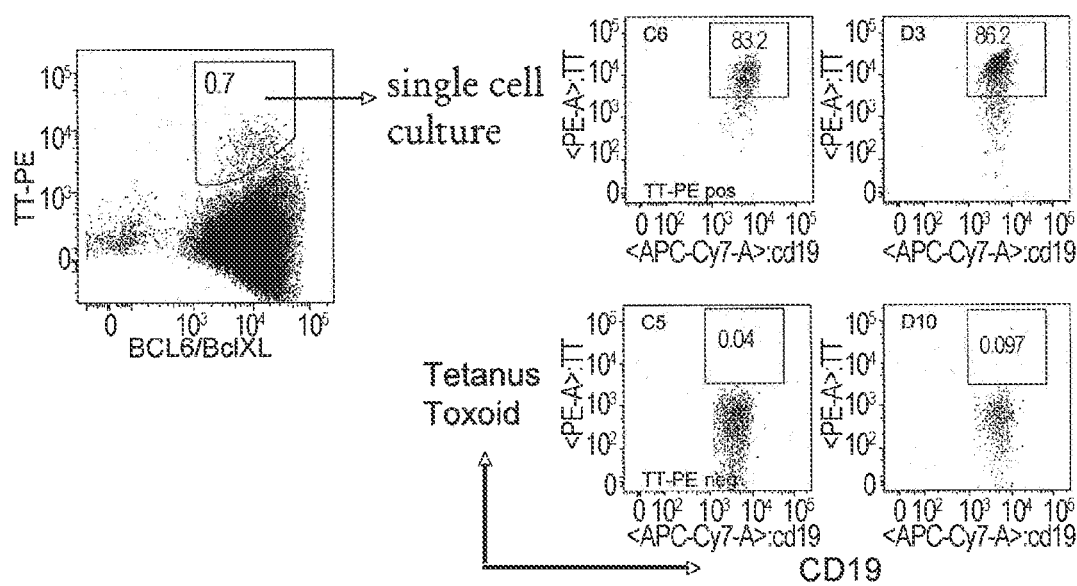
Figure 6:
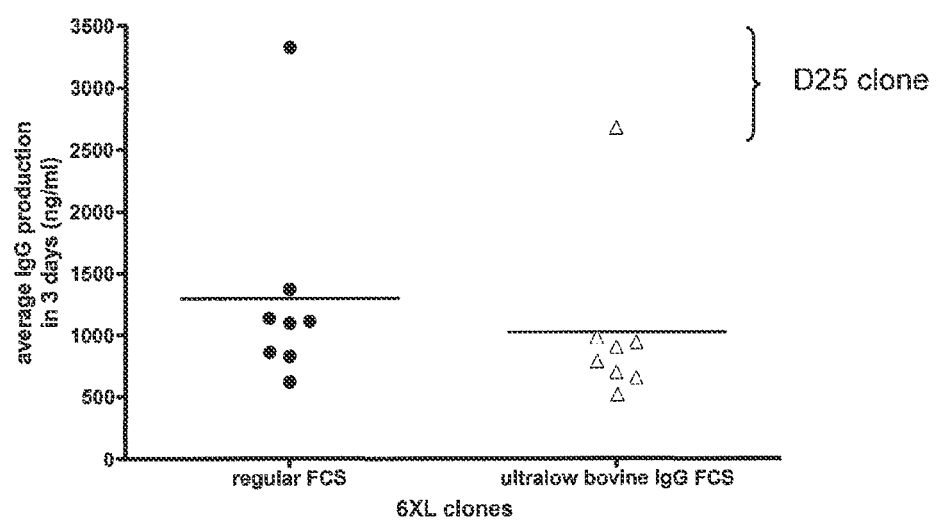
Figure 7:
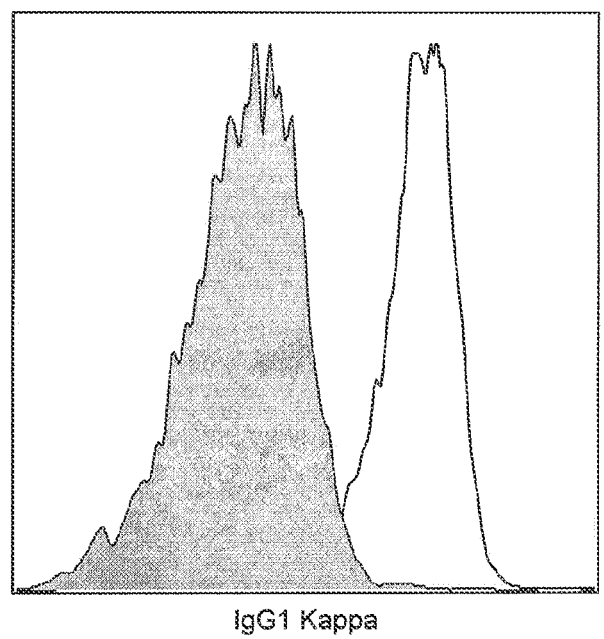
Figure 8:
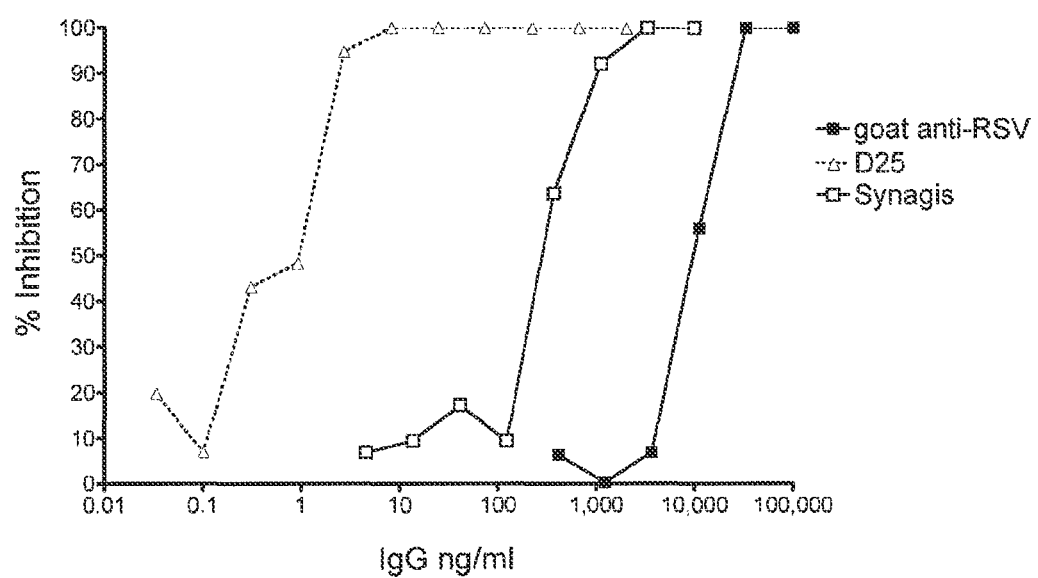

Isolation of immortalized, antigen specific human B cells. Human memory B cells were isolated as described in FIG. 1 and subsequently transduced with Bcl-6-IRES-NGFR and Bcl-XL-IRES-GFP. Cells expressing NGFR, GFP and were binding to PE-labeled Tetanus Toxin were isolated using the FACSAria. Cells were single cell cultured in 96 well flat bottom plates in the presence of irradiated L cells and IL-21 before being selected based on TT-PE binding using the FACS Canto (BD).

FIG. 5

Cumulative cell growth and division rate of 6XL B cell clones. B cells from two anti-TT clones (left side) and one anti-RSV clone (B63D10-D25) (right side) were cultured in the presence of IL-21 and irradiated L cells.

FIG. 6

Fresh cultures were started with 200,000 cell/24 well in 1.0 ml IMDM with 8% FCS and pen/strep. The FCS used was either normal (HyClone) or Ultralow Bovine IgG FCS (Gibco). After 3 days the culture supernatant was replaced and cell numbers were adjusted to 200,000 cell/ml. Shown is the average IgG production in 3 days measured in 3 consecutive time points the difference was not significant (p value 0.2).

FIG. 7

To determine the light chain phenotype of the D25 anti-RSV clone, the D25 B cell line was stained with either kappa-phycoerythrin or lambda-phycoerythrin (BD) antibodies. Only the kappa-phycoerythrin antibodies bound to the cell line, showing this antibody has a kappa light chain.

FIG. 8

From donor B63, 100 cell/well cultures were grown using Bcl-6 Bcl-XL positive human memory B cells. One of those cultures, D10 showed strong neutralization. LD derived monoclonal cell lines were made, one D25 neutralized the RSV A-2 virus efficiently. Shown here is D25 compared to palivizumab (SYNAGIS) and a polyclonal goat ant-RSV. Not shown are irrelevant culture supernatants of Bcl6 Bcl-XL transduced B cell clones cultured with IL-21 and CD40L signaling that produce high levels of antibodies but did not block RSV infection. The D25 clone was used for further characterization.

FIGS. 9A-9C

Figure 9A:
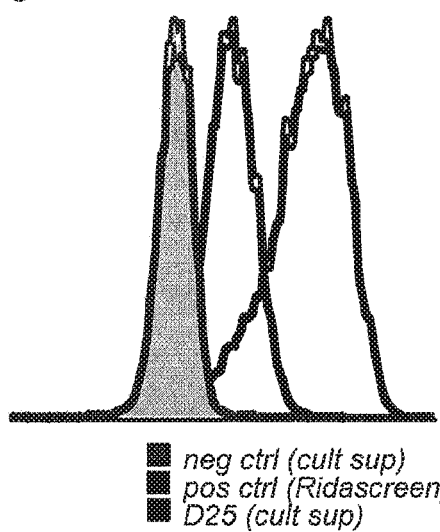

In FIG. 9A: HEp2 cell were seeded at 10-12e6 cells per T175 flask (Nunc) in IMDM/5% FCS. The next day the medium was replaced with 5 ml of medium with RSV virus (1.0 MOI) and incubated for 45' at RT before 20 ml of fresh medium was added and the cells were cultured o/n at 37° C. The next day the medium was replaced with IMDM/1% FCS and cultured o/n with a closed lid at 37° C. The next day cells were washed with PBS and treated with trypsin. To stain infected cells the primary incubation was performed with culture supernatant. The secondary incubation was done with anti-human IgG-PE (BD). Cells were analyzed using the LSRII (BD). As a positive control the positive control of the commercial ELISA KIT from r-Biopharm was used.

Figure 9B:
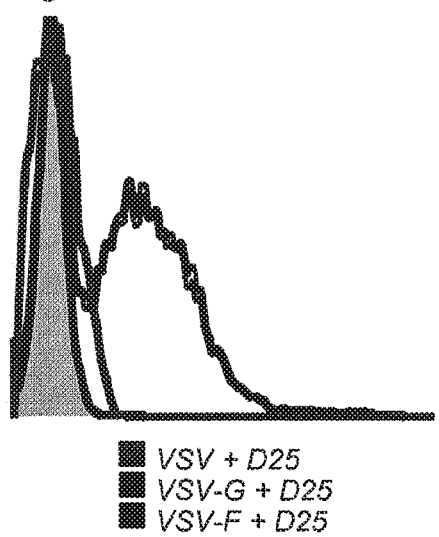
Figure 9C:
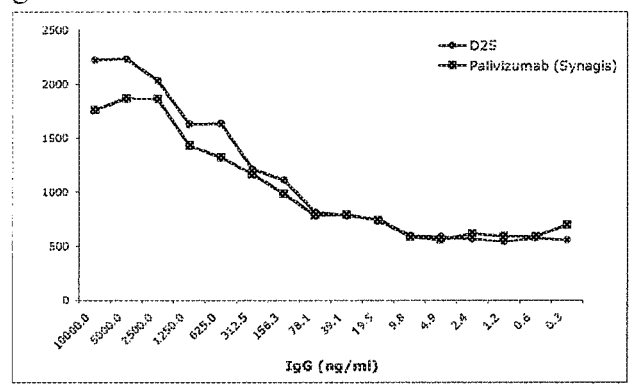
Figure 10:
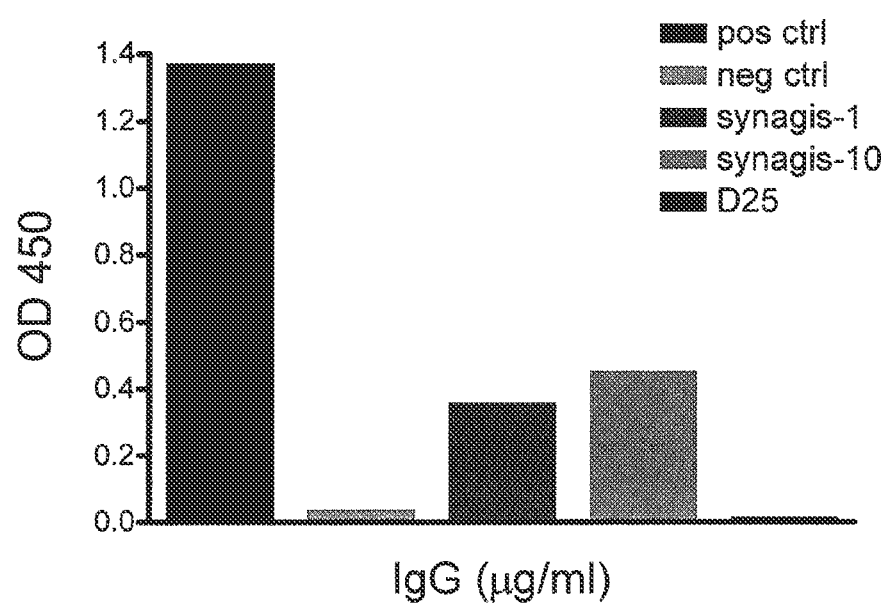
Figure 13D:
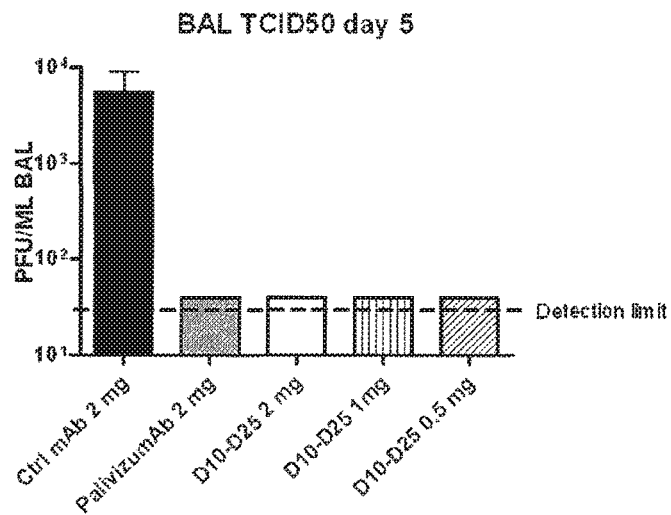
Figure 13E:
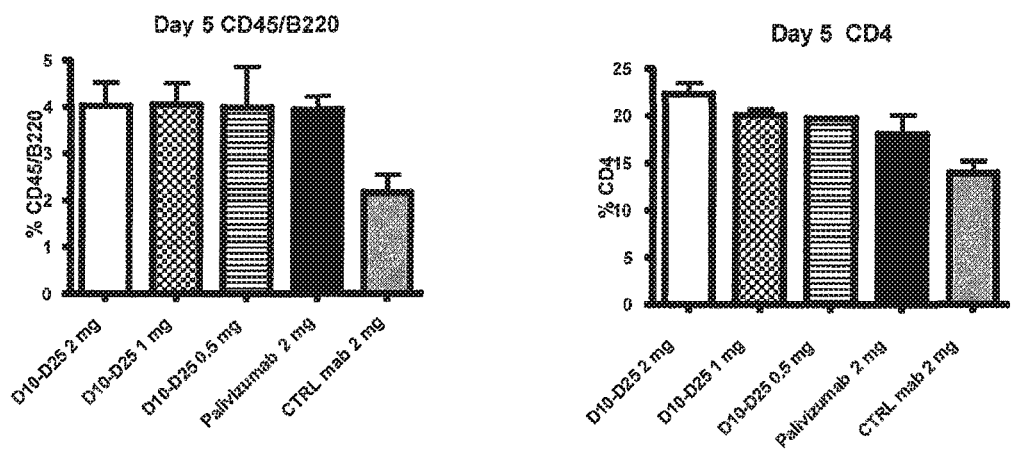
Figure 13F:
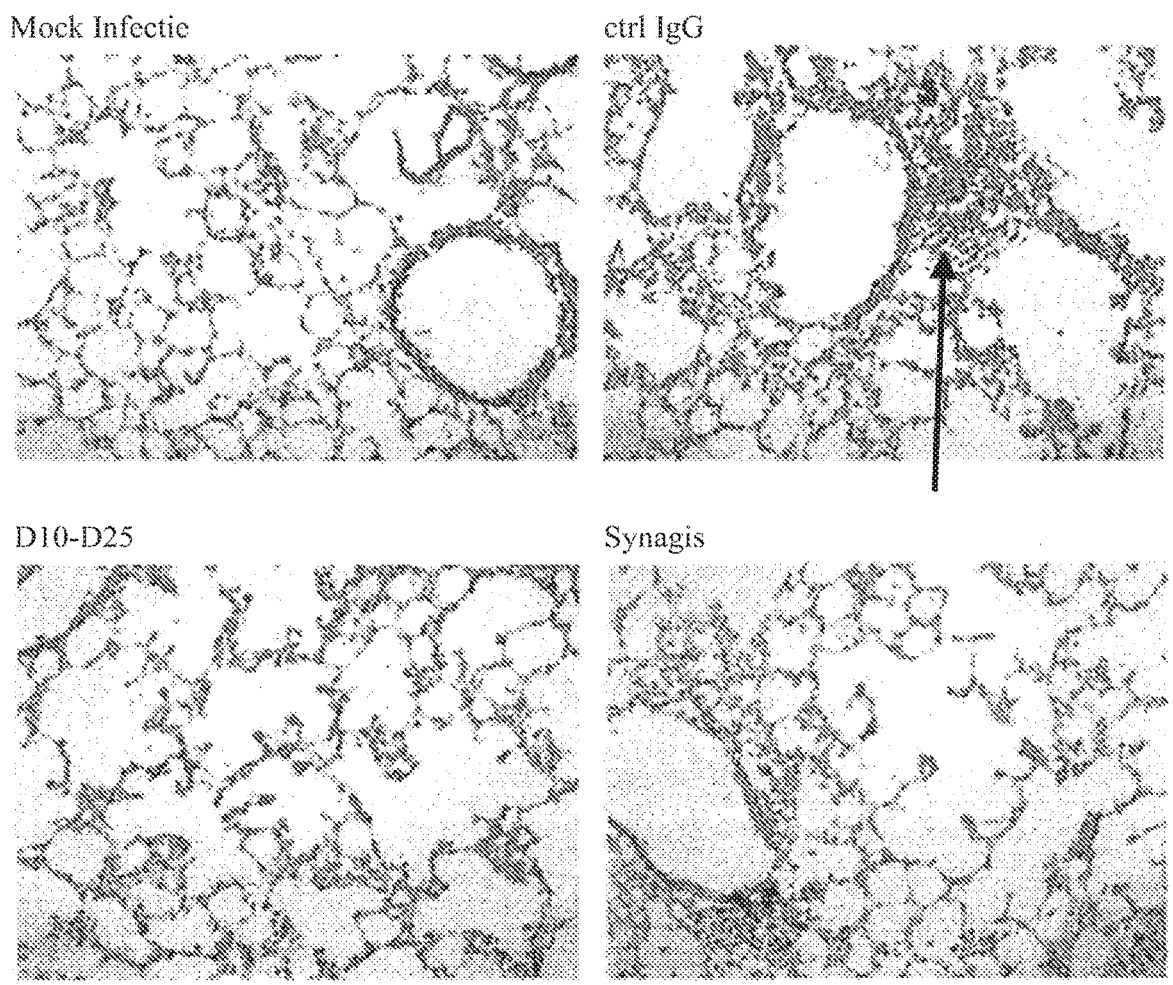
Figure 13H:
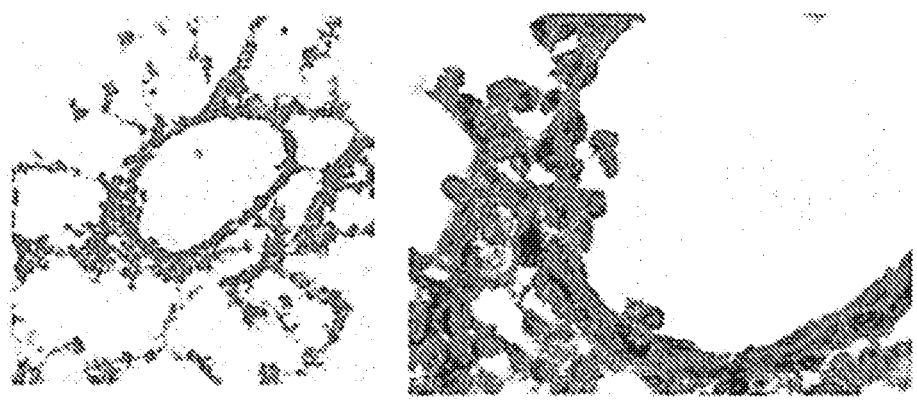
Figure 13I:
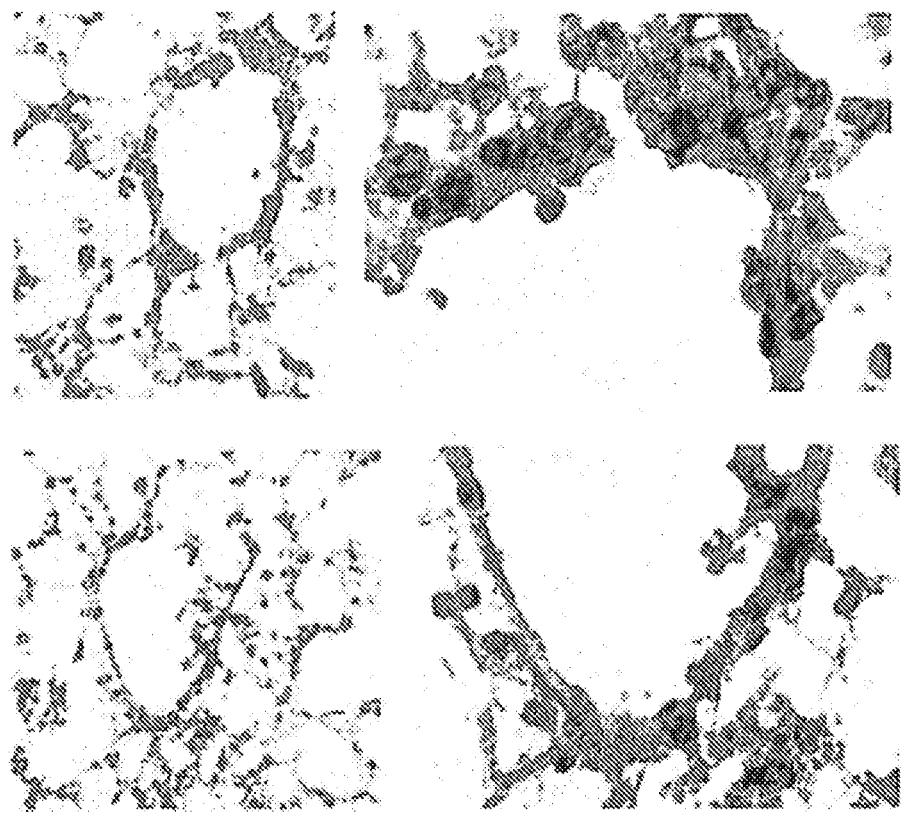
Figure 15A:
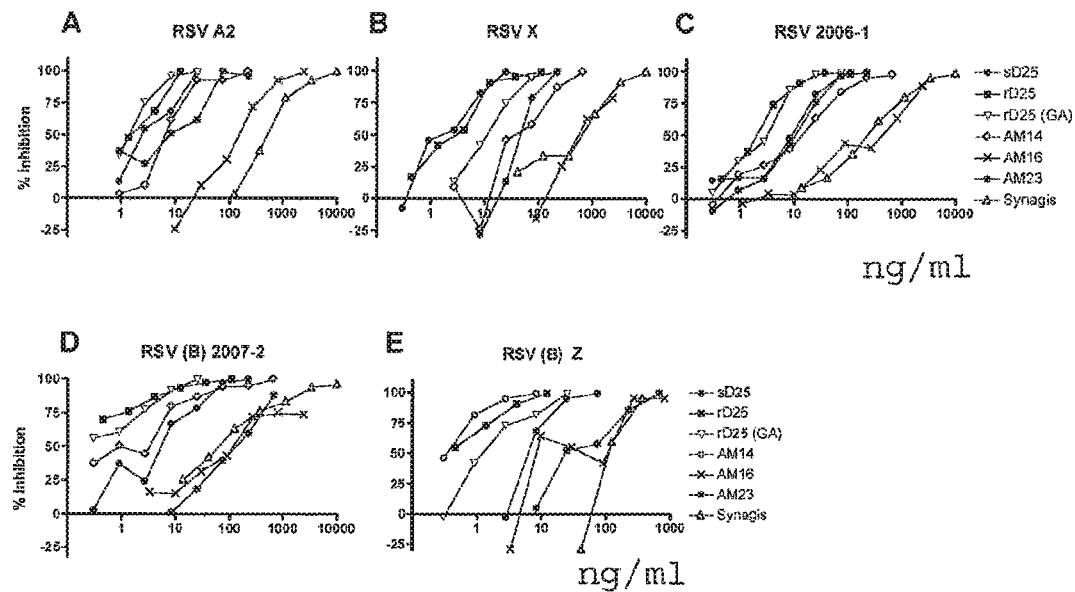
Figure 15B:
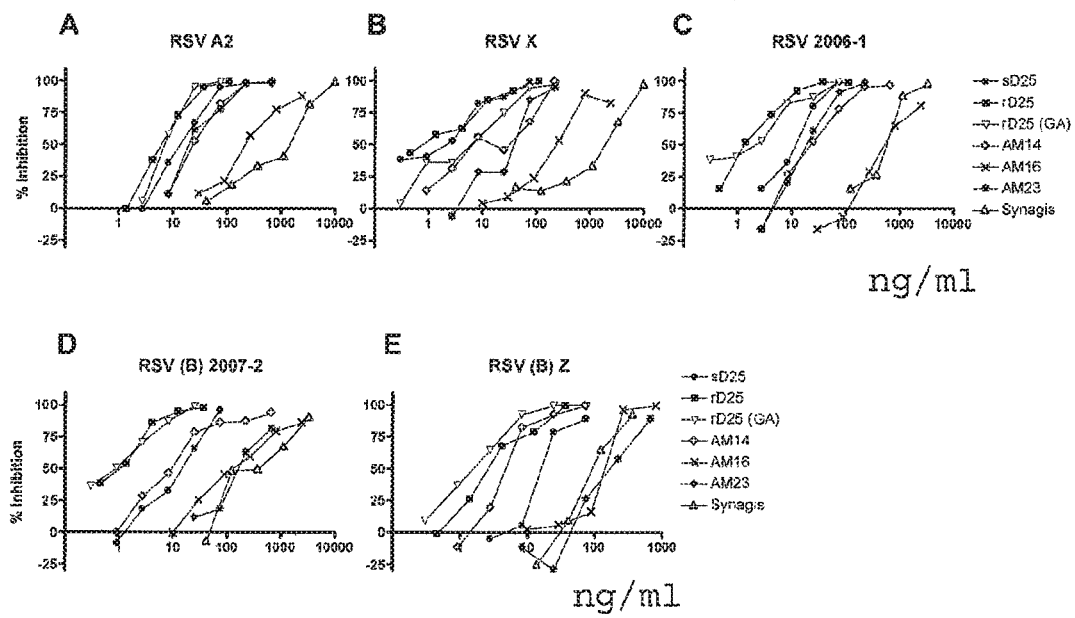
Figure 16A:
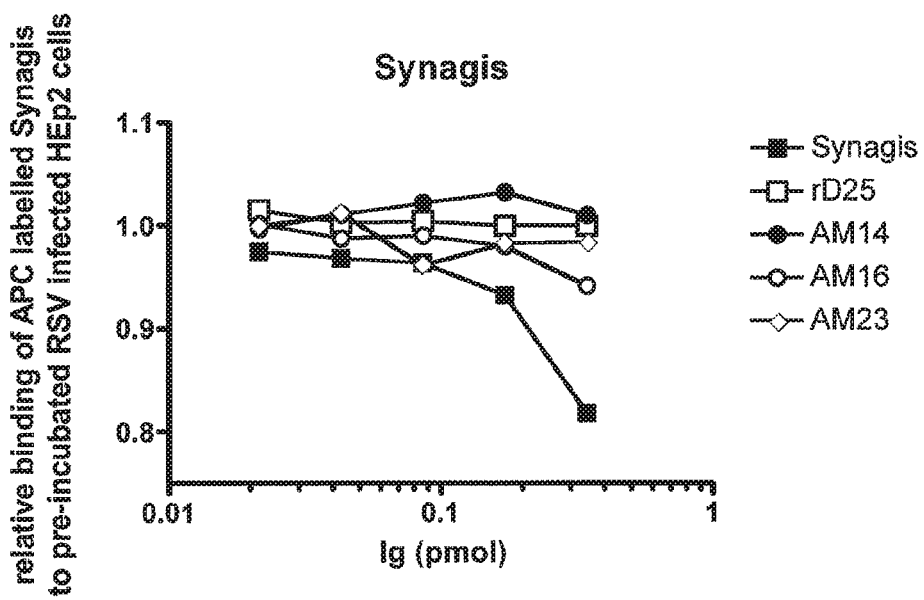
Figure 16B:
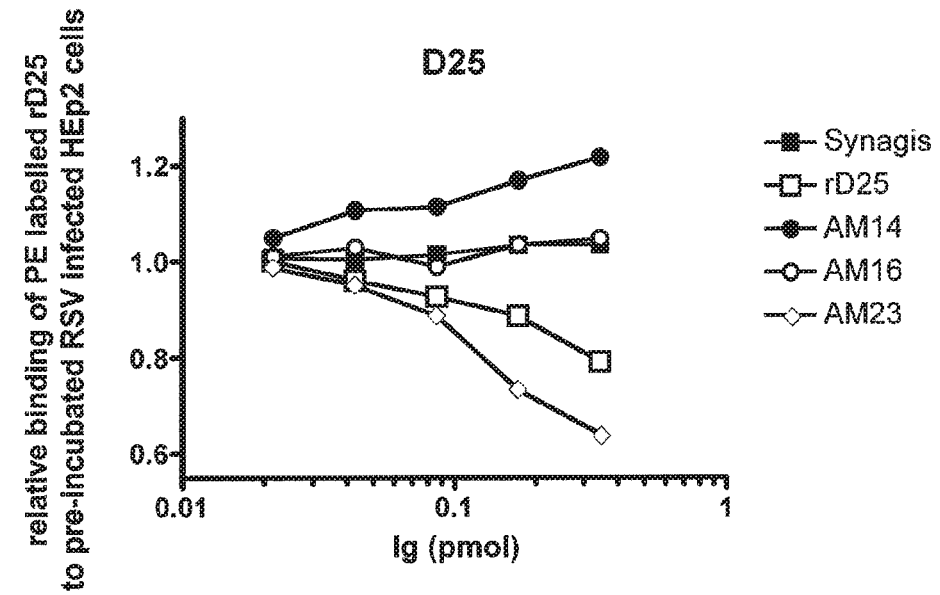

In FIG. 9B: EL-4 cells were infected with VSV virus pseudotyped with RSV F or G protein (kindly provided by John Rose) and incubated with D25 culture supernatant.

Cells were washed and incubated with anti-human-IgG-PE (Jackson) to detect binding of D25 to the infected cells. Only binding of D25 to the VSV virus infected cells pseudotyped with the RSV F protein was detected. FIG. 9C shows the binding of Palivizumab (SYNAGIS) and D25 in a concentration dependent manner to infected HEp2 cells. Shown is the mean fluorescence intensity (MFI).

FIG. 10

Binding of polyclonal goat anti-RSV (pos ctrl), palivizumab (SYNAGIS) and D25 to coated HEp2 infected cell lysate.

FIGS. 11A-11C

Sequence analysis of the D25 clone. FIG. 11A shows nucleotide and predicted amino acid sequence of the variable heavy and light chain domains (SEQ ID NOs: 7-10). FIG. 11B shows the D25 heavy chain sequence compared to predicted germline. FIG. 11C shows the D25 light chain sequence compared to predicted germline. Asterisks indicate mutations that probably occurred during selection and affinity maturation of the B cell clone in vivo. (SEQ ID NOs: 7-8, 55 and 57). Results from the IMGT/Junction analysis can be found on the world wide web at imgt.cines.fr/IMGT_vquest/vquest.

FIG. 12

FIG. 12 shows the GENEART nucleotide modifications compared to the original D25 sequence, note that these mutations do not change the amino acid composition of the D25 antibody (SEQ ID NOs: 139-142). Cloning and expression of recombinant human antibodies from BCL6 BCL-xL transduced B cell lines. This has already been described for the D25 antibody (FIG. 11).

FIGS. 13A-13J

BALB/c mice challenge with purified, B cell supernatant derived D25 and SYNAGIS FIG. 13A shows one day before RSV challenge (1×10$^7$ RSV-A2 particles) by nasal spray, animals were IP injected with different amounts of SYNAGIS (MedImmune), purified D25 or an IgG ctrl antibody (Eureka) (table 3). FIG. 13B shows the amount of human IgG at day 5 in peripheral blood of RSV challenged animals (detected by ELISA). FIG. 13C shows the drop in antibody serum levels in 5 days; table 4 shows an overview of the half-life values. FIG. 13D depicts virus titers found in lung lavages (BAL) at day 5 after RSV challenge. Virus titer was determined by standard TCID50 dilution assay on HEp2 cells. FIG. 13E depicts the percentage of B cells (by B220 staining) and T cells in mice challenged with RSV and treated with D25 or SYNAGIS or ctrl antibody. FIG. 13F shows the histology of the lungs with bronchi and infiltration of (normally mainly eosinophils) untreated and treated animals. 10× magnification. The arrow indicates cellular infiltration into the lungs, which is mostly seen around the bronchi. FIGS. 13G-13J show additional histology pictures from different mice treated with SYANGIS of D25. FIG. 13G shows results from Muis 6 with SYNAGIS at 2 mg. FIG. 13H shows results from Muis 9 with SYNAGIS at 2 mg. FIG. 13I shows results from Muis 1 with D10-D25 at 2 mg. FIG. 13J shows results from Muis 14 with D10-D25 at 2 mg.

FIGS. 14A-14L

Nucleotide and amino acid sequences of three new potent RSV neutralizing antibodies (SEQ ID NOs: 73-138, 147-148, 153-154 and 159-160). FIG. 14A shows nucleotide and amino acid sequences of the anti-RSV clone AM14. FIG. 14B shows heavy chain and light chain sequences of clone AM14 compared to germline. FIG. 14D shows CDR sequences of AM14 and the nucleotide sequences of VHeavy region AM14 (V-D-J segments). FIG. 14D shows the nucleotide sequences of VLight region AM14 (V-J segments). FIG. 14E shows nucleotide and amino acid sequences of the anti-RSV clone AM16. FIG. 14F shows heavy chain and light chain sequences of clone AM16 compared to germline. FIG. 14G shows CDR sequences of AM16 and the nucleotide sequences of VHeavy region AM16 (V-D-J segments). FIG. 14H shows the nucleotide sequences of VLight region AM16 (V-J segments). FIG. 14I shows nucleotide and amino acid sequences of the anti-RSV clone AM23. FIG. 14J shows heavy chain and light chain sequences of clone AM23 compared to germline. FIG. 14K shows CDR sequences of AM23 and the nucleotide sequences of VHeavy region AM23 (V-D-J segments). FIG. 14L shows the nucleotide sequences of VLight region AM23 (V-J segments). Results from the IMGT/Junction analysis can be found on the world wide web at imgt.cines.fr/IMGT_vquest/vquest.

FIGS. 15 A and 15B

RSV virus neutralization assay with purified B cell line supernatant derived D25 (sD25), recombinant purified D25 (rD25), recombinant GENEART codon optimized D25 (rD25 GA), AM14, AM16, AM23 (all purified recombinant protein) and SYNAGIS. Virus antibody neutralization was tested on two different cell lines Vero (FIG. 15A) and Hep2cells (FIG. 15B) with different antibodies. For each of FIGS. 15A and 15B, panel A is RSV A2 (RSV subtype A), panel B is RSV X (subtype A), panel C is RSV 2006-1 (subtype A), panel D is RSV (B) 2007-2 (subtype B), and panel E is RSV (B) Z (subtype B). 100TCID50 of each virus was added to serial antibody dilutions in DMEM/I % FCS and incubated for 1 hour at 37 degree before 100 ul Vero or HEp2 cells (1×10$^6$/ml) were added.

FIGS. 16 A and 16B

Relative binding of a fixed amount (3 pmol) of APC-labeled SYNAGIS (FIG. 16A) and PE-labeled rD25 (FIG. 16B) to RSV infected HEp2 cells that were pre-incubated with increasing concentrations of the indicated unlabeled antibodies.

REFERENCES

Banchereau, J., de Paoli, P., Valle, A., Garcia, E., Rousset, F., (1991). Long term human B cell lines dependent on interleukin-4 and antibody to CD40, Science 251, 70-2.

Boise, L. H., M. Gonzalez-Garcia, C. E, Postema, L. Ding, T. Lindsten, L. A.

Turka, X. Mao, G. Nunez, and C. B. Thompson. (1993). Bcl-x, a bcl-2-related gene that functions as a dominant regulator of apoptotic cell death. Cell 74:597.

Dadgostar, H., Zarnegar, B., Hoffmann, A., Qin, X. F., Truong, U., Rao, G., Baltimore, D., and Cheng, G. (2002). Cooperation of multiple signaling pathways in CD40-regulated gene expression in B lymphocytes. Proc. Natl. Acad. Sci USA 99, 1497-1502.

Heemskerk et al, 1997: J. Exp. Med. Vol. 186, page 1597-1602

Heemskerk et al, 1999: Cell Immunol. Vol. 195, page 10-17

Kinsella and Nolan, 1996: Hum. Gene Ther. Vol. 7 page 1405-1413

Malisan, F., Briere, F., Bridon, J. M., Harindranath, N., Mills, F. C., Max, E. E., Banchereau, J., Martinez-Valdez, H. (1996). Interleukin-10 induces immunoglobulin G isotype switch recombination in human CD40-activated naive B lymphocytes, J. Exp. Med. 183, 937-47.

Mathas S, Janz M, Hummel F, Hummel M, Wollert-Wulf B, Lusatis S, Anagnostopoulos I, Lietz A, Sigvardsson M, Jundt F, Johrens K, Bommert K, Stein H, Dorken B (2006). Intrinsic inhibition of transcription factor E2A by HLH proteins ABF-I and Id2 mediates reprogramming of neoplastic B cells in Hodgkin lymphoma. Nat Immunol. 7, 207-215.

Mejias A et al., Antimicrobial Agents and chemotherapy 2004; p 1811, Johnson S et al., JID 1997; p 1215 Wu H et al, JMB 2007:p 652

Shvarts A. et al, 2002: Genes Dev. Vol. 16, page 681-686

Traggiai, E., Becker, S., Subbarao, K., Kolesnikova, L., Uematsu, Y., Gismondo, M. R., Murphy, B. R., Rappuoli, R., Lanzavecchia, A. (2004). An efficient method to make human monoclonal antibodies from memory B cells: potent neutralization of SARS coronavirus. Nature Medicine Volume 10, No. 8, 871-875.

Ye, B. IL, Cattoretti, G., Shen, Q., Zhang, J., Hawe, N., de Waard, R., Leung, C., Nouri-Shirazi, M., Orazi, A., Chaganti, R. S., et al. (1997). The BCL-6 proto-oncogene controls germinal-centre formation and Th2-type inflammation. Nat Genet 16, 161-170.

---

The invention claimed is:

1. An isolated nucleic acid molecule comprising:
   a nucleic acid sequence encoding a heavy chain CDR1 comprising the amino acid sequence GFSFSHYA (SEQ ID NO: 73), and/or
   a nucleic acid sequence encoding a heavy chain CDR2 comprising the amino acid sequence ISYDGENT (SEQ ID NO: 74), and/or
   a nucleic acid sequence encoding a heavy chain CDR3 comprising the amino acid sequence ARDRIVD-DYYYYGMDV (SEQ ID NO: 75), and/or
   a nucleic acid sequence encoding a light chain CDR1 comprising the amino acid sequence QDIKKY (SEQ ID NO: 76), and/or
   a nucleic acid sequence encoding a light chain CDR3 comprising the amino acid sequence LPPLT (SEQ ID NO: 77);
   wherein the nucleic acid molecule comprises a cDNA sequence.

2. The isolated nucleic acid molecule according to claim 1 which comprises:
   a nucleic acid sequence encoding a heavy chain CDR1 comprising the amino acid sequence GFSFSHYA (SEQ ID NO: 73), and
   a nucleic acid sequence encoding a heavy chain CDR2 comprising the amino acid sequence ISYDGENT (SEQ ID NO: 74), and
   a nucleic acid sequence encoding a heavy chain CDR3 comprising the amino acid sequence ARDRIVD-DYYYYGMDV (SEQ ID NO: 75).

3. The isolated nucleic acid molecule according to claim 1 which comprises:
   a nucleic acid sequence encoding a light chain CDR1 comprising the amino acid sequence QDIKKY (SEQ ID NO: 76), and
   a nucleic acid sequence encoding a light chain CDR2 comprising the amino acid sequence DAS, and
   a nucleic acid sequence encoding a light chain CDR3 comprising the amino acid sequence LPPLT (SEQ ID NO: 77).

4. The isolated nucleic acid molecule according to claim 2 which comprises a nucleic acid sequence encoding a heavy chain variable region having:
   an amino acid sequence at least 70% identical to EVQLVESGGGVVQPGRSLRLSCAASGFSFSHY-AMHWVRQAPGKGLEWVAVISYDGEN TYYADS-VKGRFSISRDNSKNTVSLQMNSLRPEDTALYY-CARDRIVDDYYYYGMDVWG QGATVTVSS (SEQ ID NO: 78);
   an amino acid sequence at least 80% identical to SEQ ID NO: 78;
   an amino acid sequence at least 85% identical to SEQ ID NO: 78;
   an amino acid sequence at least 90% identical to SEQ ID NO: 78;
   an amino acid sequence at least 95% identical to SEQ ID NO: 78; or
   the amino acid sequence SEQ ID NO: 78.

5. The isolated nucleic acid molecule according to claim 3 which comprises a nucleic acid sequence encoding a light chain variable region having:
   an amino acid sequence at least 70% identical to DIQMTQSPSSLSASVGDRVTITCQASQDIKKYLN-WYHQKPGKVPELLMHDASNLETGVP SRF-SGRGSGTDFTLTISSLQPEDIGTYYCQQYDNLP-PLTFGGGTKVEIKRTV (SEQ ID NO: 79);
   an amino acid sequence at least 80% identical to SEQ ID NO: 79;
   an amino acid sequence at least 85% identical to SEQ ID NO: 79;
   an amino acid sequence at least 90% identical to SEQ ID NO: 79;
   an amino acid sequence at least 95% identical to SEQ ID NO: 79; or
   the amino acid sequence SEQ ID NO: 79.

6. The nucleic acid molecule according to claim 1, wherein:
   the nucleic acid sequence encoding the heavy chain CDR1 sequence comprising the amino acid sequence GFSFSHYA (SEQ ID NO: 73) comprises SEQ ID NO: 95,
   the nucleic acid sequence encoding the heavy chain CDR2 sequence comprising the amino acid sequence ISYDGENT (SEQ ID NO: 74) comprises SEQ ID NO: 97,
   the nucleic acid sequence encoding the heavy chain CDR3 sequence comprising the amino acid sequence ARDRIVDDYYYYGMDV (SEQ ID NO: 75) comprises SEQ ID NO: 99,
   the nucleic acid sequence encoding the light chain CDR1 sequence comprising the amino acid sequence QDIKKY (SEQ ID NO: 76) comprises SEQ ID NO: 103, and/or
   the nucleic acid sequence encoding the light chain CDR3 sequence comprising the amino acid sequence QQYDNLPPLT (SEQ ID NO: 77) comprises SEQ ID NO: 106.

7. The nucleic acid molecule according to claim 2, wherein the nucleic acid sequence encoding the heavy chain region with the amino acid sequence
   EVQLVESGGGVVQPGRSLRLSCAASGFSFSHYAM-HWVRQAPGKGLEWVAVISY DGENTYYADSVK-GRFSISRDNSKNTVSLQMNSLRPEDTALYYCAR-DRIVDDYYYYGMD VWGQGATVTVSS (SEQ ID NO: 78) comprises SEQ ID NO: 101.

8. The nucleic acid molecule according to claim 3, wherein the nucleic acid sequence encoding the light chain region with the amino acid sequence DIQMTQSPSSLSASVGDRVTITCQASQDIKKYLNWYHQKPGKVPELLMHDASNLETGVP SRFSGRGSGTDFTLTISSLQPEDIGTYYCQQYDNLPPLTFGGGTKVEIKRTV (SEQ ID NO: 79) comprises SEQ ID NO: 108.

9. The isolated nucleic acid molecule according to claim 2, further comprising a nucleic acid sequence encoding an IgG heavy chain constant region.

10. The isolated nucleic acid molecule according to claim 9, wherein the IgG molecule comprises the IgG1 isotype.

11. The isolated nucleic acid molecule according to claim 1, wherein the nucleic acid sequence encoding the heavy chain variable region and/or the nucleic acid sequence encoding the light chain variable region has been codon optimized to maximize translation into protein.

12. A vector comprising an exogenous nucleic acid molecule of claim 1.

13. An expression vector comprising a nucleic acid molecule of claim 1.

14. An isolated host cell genetically engineered to express the exogenous nucleic acid molecule of claim 1.

15. The isolated host cell of claim 14, wherein the isolated host cell is a producer cell adapted to commercial antibody production.

16. The isolated host cell of claim 14, wherein the isolated host cell is selected from a Chinese hamster ovary (CHO) cell or a 293(T) cell.

17. An isolated host cell comprising the vector of claim 12.

18. The isolated nucleic acid molecule according to claim 2 which further comprises:
    a nucleic acid sequence encoding a light chain CDR1 comprising the amino acid sequence QDIKKY (SEQ ID NO: 76), and
    a nucleic acid sequence encoding a light chain CDR2 comprising the amino acid sequence DAS, and
    a nucleic acid sequence encoding a light chain CDR3 comprising the amino acid sequence LPPLT (SEQ ID NO: 77).

19. A method for producing an antibody or antigen binding fragment thereof that binds to a respiratory syncytial virus (RSV) F protein, the method comprising providing a cell with an isolated nucleic acid molecule according to claim 18 and allowing the cell to translate the nucleic acid molecule.

20. The method of claim 19, further comprising harvesting, purifying, and/or isolating said antibody or antigen binding fragment-thereof.

21. A method for producing an antibody or antigen binding fragment thereof that binds to a respiratory syncytial virus (RSV) F protein, the method comprising providing a cell with an isolated nucleic acid molecule and allowing the cell to translate the nucleic acid molecule;
    wherein the isolated nucleic acid molecule comprises:
    a nucleic acid sequence encoding a heavy chain CDR1 comprising the amino acid sequence GFSFSHYA (SEQ ID NO: 73), and
    a nucleic acid sequence encoding a heavy chain CDR2 comprising the amino acid sequence ISYDGENT (SEQ ID NO: 74), and
    a nucleic acid sequence encoding a heavy chain CDR3 comprising the amino acid sequence ARDRIVDDYYYYGMDV (SEQ ID NO: 75), and
    a nucleic acid sequence encoding a light chain CDR1 comprising the amino acid sequence QDIKKY (SEQ ID NO: 76), and
    a nucleic acid sequence encoding a light chain CDR2 comprising the amino acid sequence DAS, and
    a nucleic acid sequence encoding a light chain CDR3 comprising the amino acid sequence LPPLT (SEQ ID NO: 77).

22. The method of claim 21, further comprising harvesting, purifying, and/or isolating said antibody or antigen binding fragment-thereof.

23. A vector comprising an exogenous nucleic acid molecule, wherein the exogenous nucleic acid molecule comprises:
    a nucleic acid sequence encoding a heavy chain CDR1 comprising the amino acid sequence GFSFSHYA (SEQ ID NO: 73), and/or
    a nucleic acid sequence encoding a heavy chain CDR2 comprising the amino acid sequence ISYDGENT (SEQ ID NO: 74), and/or
    a nucleic acid sequence encoding a heavy chain CDR3 comprising the amino acid sequence ARDRIVDDYYYYGMDV (SEQ ID NO: 75), and/or
    a nucleic acid sequence encoding a light chain CDR1 comprising the amino acid sequence QDIKKY (SEQ ID NO: 76), and/or
    a nucleic acid sequence encoding a light chain CDR3 comprising the amino acid sequence LPPLT (SEQ ID NO: 77).

24. The vector of claim 23, wherein the vector comprises an expression vector.

25. An isolated host cell comprising the expression vector of claim 24.

26. The vector of claim 23, wherein the exogenous nucleic acid molecule comprises a nucleic acid sequence encoding a heavy chain variable region having:
    an amino acid sequence at least 70% identical to EVQLVESGGGVVQPGRSLRLSCAASGFSFSHYAMHWVRQAPGKGLEWVAVISYDGEN TYYADSVKGRFSISRDNSKNTVSLQMNSLRPEDTALYYCARDRIVDDYYYYGMDVWG QGATVTVSS (SEQ ID NO: 78);
    an amino acid sequence at least 80% identical to SEQ ID NO: 78;
    an amino acid sequence at least 85% identical to SEQ ID NO: 78;
    an amino acid sequence at least 90% identical to SEQ ID NO: 78;
    an amino acid sequence at least 95% identical to SEQ ID NO: 78; or
    the amino acid sequence SEQ ID NO: 78.

27. The vector of claim 23, wherein the exogenous nucleic acid molecule comprises a nucleic acid sequence encoding a light chain variable region having:
    an amino acid sequence at least 70% identical to DIQMTQSPSSLSASVGDRVTITCQASQDIKKYLNWYHQKPGKVPELLMHDASNLETGVP SRFSGRGSGTDFTLTISSLQPEDIGTYYCQQYDNLPPLTFGGGTKVEIKRTV (SEQ ID NO: 79);
    an amino acid sequence at least 80% identical to SEQ ID NO: 79;
    an amino acid sequence at least 85% identical to SEQ ID NO: 79;
    an amino acid sequence at least 90% identical to SEQ ID NO: 79;

an amino acid sequence at least 95% identical to SEQ ID NO: 79; or the amino acid sequence SEQ ID NO: 79.

28. The vector of claim 23, wherein the exogenous nucleic acid molecule comprises a nucleic acid sequence encoding a heavy chain variable region having the amino acid sequence SEQ ID NO: 78 and a light chain variable region having the amino acid sequence SEQ ID NO: 79.

29. An isolated host cell genetically engineered to express an exogenous nucleic acid molecule, wherein the exogenous nucleic acid molecule comprises:
- a nucleic acid sequence encoding a heavy chain CDR1 comprising the amino acid sequence GFSFSHYA (SEQ ID NO: 73), and/or
- a nucleic acid sequence encoding a heavy chain CDR2 comprising the amino acid sequence ISYDGENT (SEQ ID NO: 74), and/or
- a nucleic acid sequence encoding a heavy chain CDR3 comprising the amino acid sequence ARDRIVD-DYYYYGMDV (SEQ ID NO: 75), and/or
- a nucleic acid sequence encoding a light chain CDR1 comprising the amino acid sequence QDIKKY (SEQ ID NO: 76), and/or
- a nucleic acid sequence encoding a light chain CDR3 comprising the amino acid sequence LPPLT (SEQ ID NO: 77).

30. The isolated host cell of claim 29, wherein the isolated host cell is a producer cell adapted to commercial antibody production.

31. The isolated host cell of claim 29, wherein the isolated host cell is selected from a Chinese hamster ovary (CHO) cell or a 293(T) cell.

32. The isolated host cell of claim 29, wherein the exogenous nucleic acid molecule comprises a nucleic acid sequence encoding a heavy chain variable region having:
- an amino acid sequence at least 70% identical to EVQLVESGGGVVQPGRSLRLSCAASGFSFSHY-AMHWVRQAPGKGLEWVAVISYDGEN TYYADS-VKGRFSISRDNSKNTVSLQMNSLRPEDTALYY-CARDRIVDDYYYYGMDVWG QGATVTVSS (SEQ ID NO: 78);
- an amino acid sequence at least 80% identical to SEQ ID NO: 78;
- an amino acid sequence at least 85% identical to SEQ ID NO: 78;
- an amino acid sequence at least 90% identical to SEQ ID NO: 78;
- an amino acid sequence at least 95% identical to SEQ ID NO: 78; or
- the amino acid sequence SEQ ID NO: 78.

33. The isolated host cell of claim 29, wherein the exogenous nucleic acid molecule comprises a nucleic acid sequence encoding a light chain variable region having:
- an amino acid sequence at least 70% identical to DIQMTQSPSSLSASVGDRVTITCQASQDIKKYLN-WYHQKPGKVPELLMHDASNLETGVP SRF-SGRGSGTDFTLTISSLQPEDIGTYYCQQYDNLP-PLTFGGGTKVEIKRTV (SEQ ID NO: 79);
- an amino acid sequence at least 80% identical to SEQ ID NO: 79;
- an amino acid sequence at least 85% identical to SEQ ID NO: 79;
- an amino acid sequence at least 90% identical to SEQ ID NO: 79;
- an amino acid sequence at least 95% identical to SEQ ID NO: 79; or
- the amino acid sequence SEQ ID NO: 79.

34. The isolated host cell of claim 29, wherein the exogenous nucleic acid molecule comprises a nucleic acid sequence encoding a heavy chain variable region having the amino acid sequence SEQ ID NO: 78 and a light chain variable region having the amino acid sequence SEQ ID NO: 79.

* * * * *

SEQUENCE LISTING

```
<160> NUMBER OF SEQ ID NOS: 160

<210> SEQ ID NO 1
<211> LENGTH: 5
<212> TYPE: PRT
<213> ORGANISM: Homo sapiens

<400> SEQUENCE: 1

Asn Tyr Ile Ile Asn
1               5

<210> SEQ ID NO 2
<211> LENGTH: 17
<212> TYPE: PRT
<213> ORGANISM: Homo sapiens

<400> SEQUENCE: 2

Gly Ile Ile Pro Val Leu Gly Thr Val His Tyr Ala Pro Lys Phe Gln
1               5                   10                  15

Gly

<210> SEQ ID NO 3
<211> LENGTH: 17
<212> TYPE: PRT
<213> ORGANISM: Homo sapiens

<400> SEQUENCE: 3

Glu Thr Ala Leu Val Val Ser Thr Thr Tyr Leu Pro His Tyr Phe Asp
1               5                   10                  15

Asn

<210> SEQ ID NO 4
<211> LENGTH: 11
<212> TYPE: PRT
<213> ORGANISM: Homo sapiens

<400> SEQUENCE: 4

Gln Ala Ser Gln Asp Ile Val Asn Tyr Leu Asn
1               5                   10

<210> SEQ ID NO 5
<211> LENGTH: 7
<212> TYPE: PRT
<213> ORGANISM: Homo sapiens

<400> SEQUENCE: 5

Val Ala Ser Asn Leu Glu Thr
1               5

<210> SEQ ID NO 6
<211> LENGTH: 7
<212> TYPE: PRT
<213> ORGANISM: Homo sapiens
```

<400> SEQUENCE: 6

Gln Gln Tyr Asp Asn Leu Pro
1               5

<210> SEQ ID NO 7
<211> LENGTH: 126
<212> TYPE: PRT
<213> ORGANISM: Homo sapiens

<400> SEQUENCE: 7

Gln Val Gln Leu Val Gln Ser Gly Ala Glu Val Lys Lys Pro Gly Ser
1               5                   10                  15

Ser Val Met Val Ser Cys Gln Ala Ser Gly Gly Pro Leu Arg Asn Tyr
            20                  25                  30

Ile Ile Asn Trp Leu Arg Gln Ala Pro Gly Gln Gly Pro Glu Trp Met
        35                  40                  45

Gly Gly Ile Ile Pro Val Leu Gly Thr Val His Tyr Ala Pro Lys Phe
    50                  55                  60

Gln Gly Arg Val Thr Ile Thr Ala Asp Glu Ser Thr Asp Thr Ala Tyr
65                  70                  75                  80

Ile His Leu Ile Ser Leu Arg Ser Glu Asp Thr Ala Met Tyr Tyr Cys
                85                  90                  95

Ala Thr Glu Thr Ala Leu Val Val Ser Thr Thr Tyr Leu Pro His Tyr
            100                 105                 110

Phe Asp Asn Trp Gly Gln Gly Thr Leu Val Thr Val Ser Ser
        115                 120                 125

<210> SEQ ID NO 8
<211> LENGTH: 110
<212> TYPE: PRT
<213> ORGANISM: Homo sapiens

<400> SEQUENCE: 8

Asp Ile Gln Met Thr Gln Ser Pro Ser Ser Leu Ser Ala Ala Val Gly
1               5                   10                  15

Asp Arg Val Thr Ile Thr Cys Gln Ala Ser Gln Asp Ile Val Asn Tyr
            20                  25                  30

Leu Asn Trp Tyr Gln Gln Lys Pro Gly Lys Ala Pro Lys Leu Leu Ile
        35                  40                  45

Tyr Val Ala Ser Asn Leu Glu Thr Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Val Ala Thr Tyr Tyr Cys Gln Gln Tyr Asp Asn Leu Pro Leu
                85                  90                  95

Thr Phe Gly Gly Gly Thr Lys Val Glu Ile Lys Arg Thr Val
            100                 105                 110

<210> SEQ ID NO 9
<211> LENGTH: 379
<212> TYPE: DNA
<213> ORGANISM: Homo sapiens

<400> SEQUENCE: 9
caggtgcagc tggtacagtc tggggctgaa gtgaagaagc ctgggtcctc ggtgatggtc     60
tcctgccagg cctctggagg ccccctcaga aactatatta tcaactggct acgacaggcc    120

-continued

| | |
|---|---|
| cctggacaag gccctgagtg gatgggaggg atcattcctg tcttgggtac agtacactac | 180 |
| gcaccgaagt tccagggcag agtcacgatt accgcggacg aatccacaga cacagcctac | 240 |
| atccatctga tcagcctgag atctgaggac acggccatgt attactgtgc gacggaaaca | 300 |
| gctctggttg tatctactac ctacctacca cactactttg acaactgggg ccagggaacc | 360 |
| ctggtcaccg tctcctcag | 379 |

<210> SEQ ID NO 10
<211> LENGTH: 324
<212> TYPE: DNA
<213> ORGANISM: Homo sapiens

<400> SEQUENCE: 10

| | |
|---|---|
| gacatccaga tgacccagtc tccatcctcc ctgtctgcag ctgtaggaga cagagtcacc | 60 |
| atcacttgcc aggcgagtca ggacattgtc aactatttaa attggtatca acagaaacca | 120 |
| gggaaagccc ctaagctcct gatctacgtt gcatccaatt tggagacagg ggtcccatca | 180 |
| aggttcagtg gaagtggatc tgggacagat tttagtctca ccatcagcag cctgcagcct | 240 |
| gaagatgttg caacatatta ttgtcaacaa tatgataatc tcccactcac attcggcgga | 300 |
| gggaccaagg ttgagatcaa aaga | 324 |

<210> SEQ ID NO 11
<211> LENGTH: 32
<212> TYPE: DNA
<213> ORGANISM: artificial sequence
<220> FEATURE:
<223> OTHER INFORMATION: Primer VH1

<400> SEQUENCE: 11

| | |
|---|---|
| aaatcgatac caccatggac tggacctgga gg | 32 |

<210> SEQ ID NO 12
<211> LENGTH: 32
<212> TYPE: DNA
<213> ORGANISM: artificial sequence
<220> FEATURE:
<223> OTHER INFORMATION: Primer VH1B

<400> SEQUENCE: 12

| | |
|---|---|
| aaatcgatac caccatggac tggacctgga gm | 32 |

<210> SEQ ID NO 13
<211> LENGTH: 34
<212> TYPE: DNA
<213> ORGANISM: artificial sequence
<220> FEATURE:
<223> OTHER INFORMATION: Primer VH2A

<400> SEQUENCE: 13

| | |
|---|---|
| aaatcgatac caccatggac acactttgct mcac | 34 |

<210> SEQ ID NO 14
<211> LENGTH: 35
<212> TYPE: DNA
<213> ORGANISM: artificial sequence
<220> FEATURE:
<223> OTHER INFORMATION: Primer VH2B

<400> SEQUENCE: 14

| | |
|---|---|
| aaatcgatac caccatggac atactttgtt ccaac | 35 |

```
<210> SEQ ID NO 15
<211> LENGTH: 32
<212> TYPE: DNA
<213> ORGANISM: artificial sequence
<220> FEATURE:
<223> OTHER INFORMATION: Primer VH3

<400> SEQUENCE: 15
aaatcgatac caccatggag tttgggctga gc                              32

<210> SEQ ID NO 16
<211> LENGTH: 32
<212> TYPE: DNA
<213> ORGANISM: artificial sequence
<220> FEATURE:
<223> OTHER INFORMATION: Primer VH3B

<400> SEQUENCE: 16
aaatcgatac caccatggar ytkkgrctbh gc                              32

<210> SEQ ID NO 17
<211> LENGTH: 34
<212> TYPE: DNA
<213> ORGANISM: artificial sequence
<220> FEATURE:
<223> OTHER INFORMATION: Primer VH4

<400> SEQUENCE: 17
aaatcgatac caccatgaaa cacctgtggt tctt                            34

<210> SEQ ID NO 18
<211> LENGTH: 32
<212> TYPE: DNA
<213> ORGANISM: artificial sequence
<220> FEATURE:
<223> OTHER INFORMATION: Primer VH5

<400> SEQUENCE: 18
aaatcgatac caccatgggg tcaaccgcca tc                              32

<210> SEQ ID NO 19
<211> LENGTH: 32
<212> TYPE: DNA
<213> ORGANISM: artificial sequence
<220> FEATURE:
<223> OTHER INFORMATION: Primer VH6

<400> SEQUENCE: 19
aaatcgatac caccatgtct gtctccttcc tc                              32

<210> SEQ ID NO 20
<211> LENGTH: 32
<212> TYPE: DNA
<213> ORGANISM: artificial sequence
<220> FEATURE:
<223> OTHER INFORMATION: Primer Cgamma-Rev

<400> SEQUENCE: 20
gggtctagac aggcagccca gggccgctgt gc                              32

<210> SEQ ID NO 21
<211> LENGTH: 32
<212> TYPE: DNA
<213> ORGANISM: artificial sequence
<220> FEATURE:
<223> OTHER INFORMATION: Primer Vk1
```

<400> SEQUENCE: 21
aaatcgatac caccatggac atgagggtcc cy                              32

<210> SEQ ID NO 22
<211> LENGTH: 32
<212> TYPE: DNA
<213> ORGANISM: artificial sequence
<220> FEATURE:
<223> OTHER INFORMATION: Primer Vk1B

<400> SEQUENCE: 22
aaatcgatac caccatggac atgagrgtcc yy                              32

<210> SEQ ID NO 23
<211> LENGTH: 32
<212> TYPE: DNA
<213> ORGANISM: artificial sequence
<220> FEATURE:
<223> OTHER INFORMATION: Primer Vk2

<400> SEQUENCE: 23
aaatcgatac caccatgagg ctccctgctc ag                              32

<210> SEQ ID NO 24
<211> LENGTH: 31
<212> TYPE: DNA
<213> ORGANISM: artificial sequence
<220> FEATURE:
<223> OTHER INFORMATION: Primer Vk3

<400> SEQUENCE: 24
aaatcgatac caccatggaa rccccagcgc a                               31

<210> SEQ ID NO 25
<211> LENGTH: 32
<212> TYPE: DNA
<213> ORGANISM: artificial sequence
<220> FEATURE:
<223> OTHER INFORMATION: Primer Vk4

<400> SEQUENCE: 25
aaatcgatac caccatggtg ttgcagaccc ag                              32

<210> SEQ ID NO 26
<211> LENGTH: 42
<212> TYPE: DNA
<213> ORGANISM: artificial sequence
<220> FEATURE:
<223> OTHER INFORMATION: Primer Ck-Rev

<400> SEQUENCE: 26
gatcgcggcc gcttatcaac actctcccct gttgaagctc tt                   42

<210> SEQ ID NO 27
<211> LENGTH: 36
<212> TYPE: DNA
<213> ORGANISM: artificial sequence
<220> FEATURE:
<223> OTHER INFORMATION: Primer Vl1aecb

<400> SEQUENCE: 27
aaatcgatac caccatggcc tggtcccctc tcctcc                          36

<210> SEQ ID NO 28
<211> LENGTH: 36

```
<212> TYPE: DNA
<213> ORGANISM: artificial sequence
<220> FEATURE:
<223> OTHER INFORMATION: Primer V11g

<400> SEQUENCE: 28
aaatcgatac caccatggcc ggcttccctc tcctcc                                  36

<210> SEQ ID NO 29
<211> LENGTH: 36
<212> TYPE: DNA
<213> ORGANISM: artificial sequence
<220> FEATURE:
<223> OTHER INFORMATION: Primer V12/10

<400> SEQUENCE: 29
aaatcgatac caccatggcc tgggctctgc tcctcc                                  36

<210> SEQ ID NO 30
<211> LENGTH: 36
<212> TYPE: DNA
<213> ORGANISM: artificial sequence
<220> FEATURE:
<223> OTHER INFORMATION: Primer V13jpah

<400> SEQUENCE: 30
aaatcgatac caccatggcc tggaccgctc tcctgc                                  36

<210> SEQ ID NO 31
<211> LENGTH: 36
<212> TYPE: DNA
<213> ORGANISM: artificial sequence
<220> FEATURE:
<223> OTHER INFORMATION: Primer V15/7

<400> SEQUENCE: 31
aaatcgatac caccatggcc tggactcctc tccttc                                  36

<210> SEQ ID NO 32
<211> LENGTH: 36
<212> TYPE: DNA
<213> ORGANISM: artificial sequence
<220> FEATURE:
<223> OTHER INFORMATION: Primer V16/9

<400> SEQUENCE: 32
aaatcgatac caccatggcc tgggctcctc tccttc                                  36

<210> SEQ ID NO 33
<211> LENGTH: 36
<212> TYPE: DNA
<213> ORGANISM: artificial sequence
<220> FEATURE:
<223> OTHER INFORMATION: Primer V13rm

<400> SEQUENCE: 33
aaatcgatac caccatggcc tggatccctc tcctcc                                  36

<210> SEQ ID NO 34
<211> LENGTH: 36
<212> TYPE: DNA
<213> ORGANISM: artificial sequence
<220> FEATURE:
<223> OTHER INFORMATION: Primer V13l

<400> SEQUENCE: 34
```
aaatcgatac caccatggcc tggacccctc tctggc                                    36

<210> SEQ ID NO 35
<211> LENGTH: 36
<212> TYPE: DNA
<213> ORGANISM: artificial sequence
<220> FEATURE:
<223> OTHER INFORMATION: Primer V13e

<400> SEQUENCE: 35
aaatcgatac caccatggcc tgggccacac tcctgc                                    36

<210> SEQ ID NO 36
<211> LENGTH: 36
<212> TYPE: DNA
<213> ORGANISM: artificial sequence
<220> FEATURE:
<223> OTHER INFORMATION: Primer V14c

<400> SEQUENCE: 36
aaatcgatac caccatggcc tgggtctcct tctacc                                    36

<210> SEQ ID NO 37
<211> LENGTH: 36
<212> TYPE: DNA
<213> ORGANISM: artificial sequence
<220> FEATURE:
<223> OTHER INFORMATION: Primer V18a

<400> SEQUENCE: 37
aaatcgatac caccatggcc tggatgatgc ttctcc                                    36

<210> SEQ ID NO 38
<211> LENGTH: 41
<212> TYPE: DNA
<213> ORGANISM: artificial sequence
<220> FEATURE:
<223> OTHER INFORMATION: Primer C12/7

<400> SEQUENCE: 38
gatcgcggcc gcttatcawg arcattctgy aggggccact g                              41

<210> SEQ ID NO 39
<211> LENGTH: 31
<212> TYPE: DNA
<213> ORGANISM: artificial sequence
<220> FEATURE:
<223> OTHER INFORMATION: Primer VH1-L-NheI

<400> SEQUENCE: 39
gcggctagcc accatggact ggacctggag g                                         31

<210> SEQ ID NO 40
<211> LENGTH: 29
<212> TYPE: DNA
<213> ORGANISM: artificial sequence
<220> FEATURE:
<223> OTHER INFORMATION: Primer JH4/5-XhoI

<400> SEQUENCE: 40
gcgctcgaga cggtgaccag ggttccctg                                            29

<210> SEQ ID NO 41
<211> LENGTH: 35
<212> TYPE: DNA
<213> ORGANISM: artificial sequence
<220> FEATURE:
<223> OTHER INFORMATION: Primer CHfw-XhoI

<400> SEQUENCE: 41
cgcgctcgag tgcctccacc aagggcccat cggtc        35

<210> SEQ ID NO 42
<211> LENGTH: 41
<212> TYPE: DNA
<213> ORGANISM: artificial sequence
<220> FEATURE:
<223> OTHER INFORMATION: Primer CHrev-NotI

<400> SEQUENCE: 42
gatcgcggcc gcttatcatt tacccggrga cagggagagg c        41

<210> SEQ ID NO 43
<211> LENGTH: 31
<212> TYPE: DNA
<213> ORGANISM: artificial sequence
<220> FEATURE:
<223> OTHER INFORMATION: Primer VK1-L-NheI

<400> SEQUENCE: 43
gcggctagcc accatggaca tgagggtccc y        31

<210> SEQ ID NO 44
<211> LENGTH: 42
<212> TYPE: DNA
<213> ORGANISM: artificial sequence
<220> FEATURE:
<223> OTHER INFORMATION: Primer CK-NotI

<400> SEQUENCE: 44
gatcgcggcc gcttatcaac actctcccct gttgaagctc tt        42

<210> SEQ ID NO 45
<211> LENGTH: 24
<212> TYPE: DNA
<213> ORGANISM: artificial sequence
<220> FEATURE:
<223> OTHER INFORMATION: Primer HPRT1 forward

<400> SEQUENCE: 45
tatggacagg actgaacgtc ttgc        24

<210> SEQ ID NO 46
<211> LENGTH: 26
<212> TYPE: DNA
<213> ORGANISM: artificial sequence
<220> FEATURE:
<223> OTHER INFORMATION: Primer HPRT1 reverse

<400> SEQUENCE: 46
gacacaaaca tgattcaaat ccctga        26

<210> SEQ ID NO 47
<211> LENGTH: 20
<212> TYPE: DNA
<213> ORGANISM: artificial sequence
<220> FEATURE:
<223> OTHER INFORMATION: Primer LMP-1 forward

<400> SEQUENCE: 47
gcgactctgc tggaaatgat        20

<210> SEQ ID NO 48
<211> LENGTH: 20
<212> TYPE: DNA
<213> ORGANISM: artificial sequence
<220> FEATURE:
<223> OTHER INFORMATION: Primer LMP-1 reverse

<400> SEQUENCE: 48
gacatggtaa tgcctagaag                                          20

<210> SEQ ID NO 49
<211> LENGTH: 22
<212> TYPE: DNA
<213> ORGANISM: artificial sequence
<220> FEATURE:
<223> OTHER INFORMATION: Primer EBNA1/2 forward

<400> SEQUENCE: 49
agcaagaaga ggaggtggta ag                                       22

<210> SEQ ID NO 50
<211> LENGTH: 22
<212> TYPE: DNA
<213> ORGANISM: artificial sequence
<220> FEATURE:
<223> OTHER INFORMATION: Primer EBNA1/2 reverse

<400> SEQUENCE: 50
ggctcaaagt ggtctctaat gc                                       22

<210> SEQ ID NO 51
<211> LENGTH: 379
<212> TYPE: DNA
<213> ORGANISM: artificial sequence
<220> FEATURE:
<223> OTHER INFORMATION: Anti-RSV clone B63D10-D25
<220> FEATURE:
<221> NAME/KEY: CDS
<222> LOCATION: (1)..(378)

<400> SEQUENCE: 51

```
cag gtg cag ctg gta cag tct ggg gct gaa gtg aag aag cct ggg tcc       48
Gln Val Gln Leu Val Gln Ser Gly Ala Glu Val Lys Lys Pro Gly Ser
1               5                   10                  15 tcg gtg atg gtc tcc tgc cag gcc tct gga ggc ccc ctc aga aac tat       96
Ser Val Met Val Ser Cys Gln Ala Ser Gly Gly Pro Leu Arg Asn Tyr
            20                  25                  30 att atc aac tgg cta cga cag gcc cct gga caa ggc cct gag tgg atg      144
Ile Ile Asn Trp Leu Arg Gln Ala Pro Gly Gln Gly Pro Glu Trp Met
        35                  40                  45 gga ggg atc att cct gtc ttg ggt aca gta cac tac gca ccg aag ttc      192
Gly Gly Ile Ile Pro Val Leu Gly Thr Val His Tyr Ala Pro Lys Phe
    50                  55                  60 cag ggc aga gtc acg att acc gcg gac gaa tcc aca gac aca gcc tac      240
Gln Gly Arg Val Thr Ile Thr Ala Asp Glu Ser Thr Asp Thr Ala Tyr
65                  70                  75                  80 atc cat ctg atc agc ctg aga tct gag gac acg gcc atg tat tac tgt      288
Ile His Leu Ile Ser Leu Arg Ser Glu Asp Thr Ala Met Tyr Tyr Cys
                85                  90                  95 gcg acg gaa aca gct ctg gtt gta tct act acc tac cta cca cac tac      336
Ala Thr Glu Thr Ala Leu Val Val Ser Thr Thr Tyr Leu Pro His Tyr
            100                 105                 110 ttt gac aac tgg ggc cag gga acc ctg gtc acc gtc tcc tca g            379
Phe Asp Asn Trp Gly Gln Gly Thr Leu Val Thr Val Ser Ser
        115                 120                 125
```

<210> SEQ ID NO 52
<211> LENGTH: 126
<212> TYPE: PRT
<213> ORGANISM: artificial sequence
<220> FEATURE:
<223> OTHER INFORMATION: Synthetic Construct

<400> SEQUENCE: 52

Gln Val Gln Leu Val Gln Ser Gly Ala Glu Val Lys Lys Pro Gly Ser
1               5                   10                  15
Ser Val Met Val Ser Cys Gln Ala Ser Gly Gly Pro Leu Arg Asn Tyr
            20                  25                  30
Ile Ile Asn Trp Leu Arg Gln Ala Pro Gly Gln Gly Pro Glu Trp Met
        35                  40                  45
Gly Gly Ile Ile Pro Val Leu Gly Thr Val His Tyr Ala Pro Lys Phe
    50                  55                  60
Gln Gly Arg Val Thr Ile Thr Ala Asp Glu Ser Thr Asp Thr Ala Tyr
65                  70                  75                  80
Ile His Leu Ile Ser Leu Arg Ser Glu Asp Thr Ala Met Tyr Tyr Cys
                85                  90                  95
Ala Thr Glu Thr Ala Leu Val Val Ser Thr Thr Tyr Leu Pro His Tyr
            100                 105                 110
Phe Asp Asn Trp Gly Gln Gly Thr Leu Val Thr Val Ser Ser
        115                 120                 125

<210> SEQ ID NO 53
<211> LENGTH: 324
<212> TYPE: DNA
<213> ORGANISM: artificial sequence
<220> FEATURE:
<223> OTHER INFORMATION: VL region
<220> FEATURE:
<221> NAME/KEY: CDS
<222> LOCATION: (1)..(324)

<400> SEQUENCE: 53

```
gac atc cag atg acc cag tct cca tcc tcc ctg tct gca gct gta gga       48
Asp Ile Gln Met Thr Gln Ser Pro Ser Ser Leu Ser Ala Ala Val Gly
1               5                   10                  15 gac aga gtc acc atc act tgc cag gcg agt cag gac att gtc aac tat       96
Asp Arg Val Thr Ile Thr Cys Gln Ala Ser Gln Asp Ile Val Asn Tyr
            20                  25                  30 tta aat tgg tat caa cag aaa cca ggg aaa gcc cct aag ctc ctg atc      144
Leu Asn Trp Tyr Gln Gln Lys Pro Gly Lys Ala Pro Lys Leu Leu Ile
        35                  40                  45 tac gtt gca tcc aat ttg gag aca ggg gtc cca tca agg ttc agt gga      192
Tyr Val Ala Ser Asn Leu Glu Thr Gly Val Pro Ser Arg Phe Ser Gly
    50                  55                  60 agt gga tct ggg aca gat ttt agt ctc acc atc agc agc ctg cag cct      240
Ser Gly Ser Gly Thr Asp Phe Ser Leu Thr Ile Ser Ser Leu Gln Pro
65                  70                  75                  80 gaa gat gtt gca aca tat tat tgt caa caa tat gat aat ctc cca ctc      288
Glu Asp Val Ala Thr Tyr Tyr Cys Gln Gln Tyr Asp Asn Leu Pro Leu
                85                  90                  95 aca ttc ggc gga ggg acc aag gtt gag atc aaa aga                      324
Thr Phe Gly Gly Gly Thr Lys Val Glu Ile Lys Arg
            100                 105
```

<210> SEQ ID NO 54

-continued

```
<211> LENGTH: 108
<212> TYPE: PRT
<213> ORGANISM: artificial sequence
<220> FEATURE:
<223> OTHER INFORMATION: Synthetic Construct

<400> SEQUENCE: 54

Asp Ile Gln Met Thr Gln Ser Pro Ser Ser Leu Ser Ala Ala Val Gly
1               5                   10                  15

Asp Arg Val Thr Ile Thr Cys Gln Ala Ser Gln Asp Ile Val Asn Tyr
            20                  25                  30

Leu Asn Trp Tyr Gln Gln Lys Pro Gly Lys Ala Pro Lys Leu Leu Ile
        35                  40                  45

Tyr Val Ala Ser Asn Leu Glu Thr Gly Val Pro Ser Arg Phe Ser Gly
50                  55                  60

Ser Gly Ser Gly Thr Asp Phe Ser Leu Thr Ile Ser Ser Leu Gln Pro
65                  70                  75                  80

Glu Asp Val Ala Thr Tyr Tyr Cys Gln Gln Tyr Asp Asn Leu Pro Leu
                85                  90                  95

Thr Phe Gly Gly Gly Thr Lys Val Glu Ile Lys Arg
            100                 105

<210> SEQ ID NO 55
<211> LENGTH: 98
<212> TYPE: PRT
<213> ORGANISM: artificial sequence
<220> FEATURE:
<223> OTHER INFORMATION: VH1-69 germl

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 56
<211> LENGTH: 126
<212> TYPE: PRT
<213> ORGANISM: artificial sequence
<220> FEATURE:
<223> OTHER INFORMATION: B63D10-D25

<400> SEQUENCE: 56

Gln Val Gln Leu Val Gln Ser Gly Ala Glu Val Lys Lys Pro Gly Ser
1               5                   10                  15

Ser Val Met Val Ser Cys Gln Ala Ser Gly Gly Pro Leu Arg Asn Tyr
            20                  25                  30

Ile Ile Asn Trp Leu Arg Gln Ala Pro Gly Gln Gly Pro Glu Trp Met
        35                  40                  45

Gly Gly Ile Ile Pro Val Leu Gly Thr Val His Tyr Ala Pro Lys Phe
```

```
                 50                  55                  60
Gln Gly Arg Val Thr Ile Thr Ala Asp Glu Ser Thr Asp Thr Ala Tyr
 65                  70                  75                  80

Ile His Leu Ile Ser Leu Arg Ser Glu Asp Thr Ala Met Tyr Tyr Cys
                     85                  90                  95

Ala Thr Glu Thr Ala Leu Val Val Ser Thr Thr Tyr Leu Pro His Tyr
                    100                 105                 110

Phe Asp Asn Trp Gly Gln Gly Thr Leu Val Thr Val Ser Ser
                115                 120                 125

<210> SEQ ID NO 57
<211> LENGTH: 95
<212> TYPE: PRT
<213> ORGANISM: artificial sequence
<220> FEATURE:
<223> OTHER INFORMATION: VkI O8/O18

<400> SEQUENCE: 57

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro
                 85                  90                  95

<210> SEQ ID NO 58
<211> LENGTH: 110
<212> TYPE: PRT
<213> ORGANISM: artificial sequence
<220> FEATURE:
<223> OTHER INFORMATION: B63D10-D25

<400> SEQUENCE: 58

Asp Ile Gln Met Thr Gln Ser Pro Ser Ser Leu Ser Ala Ala Val Gly
 1               5                  10                  15

Asp Arg Val Thr Ile Thr Cys Gln Ala Ser Gln Asp Ile Val Asn Tyr
                 20                  25                  30

Leu Asn Trp Tyr Gln Gln Lys Pro Gly Lys Ala Pro Lys Leu Leu Ile
             35                  40                  45

Tyr Val Ala Ser Asn Leu Glu Thr Gly Val Pro Ser Arg Phe Ser Gly
 50                  55                  60

Ser Gly Ser Gly Thr Asp Phe Ser Leu Thr Ile Ser Ser Leu Gln Pro
 65                  70                  75                  80

Glu Asp Val Ala Thr Tyr Tyr Cys Gln Gln Tyr Asp Asn Leu Pro Leu
                 85                  90                  95

Thr Phe Gly Gly Gly Thr Lys Val Glu Ile Lys Arg Thr Val
                100                 105                 110

<210> SEQ ID NO 59
<211> LENGTH: 91
<212> TYPE: DNA
<213> ORGANISM: artificial sequence
<220> FEATURE:
```

<223> OTHER INFORMATION: FR1 VHeavy region D25

<400> SEQUENCE: 59

```
caggtgcagc tggtacagtc tggggctgaa gtgaagaagc ctgggtcctc ggtgatggtc      60
tcctgccagg cctctggagg ccccctcaga a                                     91
```

<210> SEQ ID NO 60
<211> LENGTH: 14
<212> TYPE: DNA
<213> ORGANISM: artificial sequence
<220> FEATURE:
<223> OTHER INFORMATION: CDR1 VHeavy region D25

<400> SEQUENCE: 60

```
actatattat caac                                                        14
```

<210> SEQ ID NO 61
<211> LENGTH: 42
<212> TYPE: DNA
<213> ORGANISM: artificial sequence
<220> FEATURE:
<223> OTHER INFORMATION: FR2 VHeavy region D25

<400> SEQUENCE: 61

```
tggctacgac aggcccctgg acaaggccct gagtggatgg ga                         42
```

<210> SEQ ID NO 62
<211> LENGTH: 51
<212> TYPE: DNA
<213> ORGANISM: artificial sequence
<220> FEATURE:
<223> OTHER INFORMATION: CDR2 VHeavy region D25

<400> SEQUENCE: 62

```
gggatcattc ctgtcttggg tacagtacac tacgcaccga agttccaggg c               51
```

<210> SEQ ID NO 63
<211> LENGTH: 96
<212> TYPE: DNA
<213> ORGANISM: artificial sequence
<220> FEATURE:
<223> OTHER INFORMATION: FR3 VHeavy region D25

<400> SEQUENCE: 63

```
agagtcacga ttaccgcgga cgaatccaca gacacagcct acatccatct gatcagcctg      60
agatctgagg acacggccat gtattactgt gcgacg                                96
```

<210> SEQ ID NO 64
<211> LENGTH: 51
<212> TYPE: DNA
<213> ORGANISM: artificial sequence
<220> FEATURE:
<223> OTHER INFORMATION: CDR3 VHeavy region D25

<400> SEQUENCE: 64

```
gaaacagctc tggttgtatc tactacctac ctaccacact actttgacaa c               51
```

<210> SEQ ID NO 65
<211> LENGTH: 34
<212> TYPE: DNA
<213> ORGANISM: artificial sequence
<220> FEATURE:
<223> OTHER INFORMATION: FR4 VHeavy region D25

<400> SEQUENCE: 65

-continued tggggccagg gaaccctggt caccgtctcc tcag                                34

<210> SEQ ID NO 66
<211> LENGTH: 69
<212> TYPE: DNA
<213> ORGANISM: artificial sequence
<220> FEATURE:
<223> OTHER INFORMATION: FR1 VLight region D25

<400> SEQUENCE: 66
gacatccaga tgacccagtc tccatcctcc ctgtctgcag ctgtaggaga cagagtcacc   60
atcacttgc                                                          69

<210> SEQ ID NO 67
<211> LENGTH: 33
<212> TYPE: DNA
<213> ORGANISM: artificial sequence
<220> FEATURE:
<223> OTHER INFORMATION: CDR1 VLight region D25

<400> SEQUENCE: 67
caggcgagtc aggacattgt caactattta aat                               33

<210> SEQ ID NO 68
<211> LENGTH: 45
<212> TYPE: DNA
<213> ORGANISM: artificial sequence
<220> FEATURE:
<223> OTHER INFORMATION: FR2 VLight region D25

<400> SEQUENCE: 68
tggtatcaac agaaaccagg gaaagcccct aagctcctga tctac                  45

<210> SEQ ID NO 69
<211> LENGTH: 21
<212> TYPE: DNA
<213> ORGANISM: artificial sequence
<220> FEATURE:
<223> OTHER INFORMATION: CRD2 VLight region D25

<400> SEQUENCE: 69
gttgcatcca atttggagac a                                            21

<210> SEQ ID NO 70
<211> LENGTH: 96
<212> TYPE: DNA
<213> ORGANISM: artificial sequence
<220> FEATURE:
<223> OTHER INFORMATION: FR3 VLight region D25

<400> SEQUENCE: 70
ggggtcccat caaggttcag tggaagtgga tctgggacag attttagtct caccatcagc   60
agcctgcagc ctgaagatgt tgcaacatat tattgt                            96

<210> SEQ ID NO 71
<211> LENGTH: 21
<212> TYPE: DNA
<213> ORGANISM: artificial sequence
<220> FEATURE:
<223> OTHER INFORMATION: CDR3 VLight region D25

<400> SEQUENCE: 71
caacaatatg ataatctccc a                                            21

```
<210> SEQ ID NO 72
<211> LENGTH: 39
<212> TYPE: DNA
<213> ORGANISM: artificial sequence
<220> FEATURE:
<223> OTHER INFORMATION: FR4 VLight region D25

<400> SEQUENCE: 72
ctcacattcg gcggagggac caaggttgag atcaaaaga                              39

<210> SEQ ID NO 73
<211> LENGTH: 8
<212> TYPE: PRT
<213> ORGANISM: Homo sapiens

<400> SEQUENCE: 73

Gly Phe Ser Phe Ser His Tyr Ala
1               5

<210> SEQ ID NO 74
<211> LENGTH: 8
<212> TYPE: PRT
<213> ORGANISM: Homo sapiens

<400> SEQUENCE: 74

Ile Ser Tyr Asp Gly Glu Asn Thr
1               5

<210> SEQ ID NO 75
<211> LENGTH: 16
<212> TYPE: PRT
<213> ORGANISM: Homo sapiens

<400> SEQUENCE: 75

Ala Arg Asp Arg Ile Val Asp Tyr Tyr Tyr Tyr Gly Met Asp Val
1               5                   10                  15

<210> SEQ ID NO 76
<211> LENGTH: 6
<212> TYPE: PRT
<213> ORGANISM: Homo sapiens

<400> SEQUENCE: 76

Gln Asp Ile Lys Lys Tyr
1               5

<210> SEQ ID NO 77
<211> LENGTH: 10
<212> TYPE: PRT
<213> ORGANISM: Homo sapiens

<400> SEQUENCE: 77

Gln Gln Tyr Asp Asn Leu Pro Pro Leu Thr
1               5                   10

<210> SEQ ID NO 78
<211> LENGTH: 123
<212> TYPE: PRT
<213> ORGANISM: Homo sapiens

<400> SEQUENCE: 78

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser His Tyr
```

```
                20                  25                  30
Ala Met His Trp Val Arg Gln Ala Pro Gly Lys Gly Leu Glu Trp Val
            35                  40                  45
Ala Val Ile Ser Tyr Asp Gly Glu Asn Thr Tyr Tyr Ala Asp Ser Val
        50                  55                  60
Lys Gly Arg Phe Ser Ile Ser Arg Asp Asn Ser Lys Asn Thr Val Ser
65                  70                  75                  80
Leu Gln Met Asn Ser Leu Arg Pro Glu Asp Thr Ala Leu Tyr Tyr Cys
                85                  90                  95
Ala Arg Asp Arg Ile Val Asp Asp Tyr Tyr Tyr Tyr Gly Met Asp Val
            100                 105                 110
Trp Gly Gln Gly Ala Thr Val Thr Val Ser Ser
            115                 120

<210> SEQ ID NO 79
<211> LENGTH: 111
<212> TYPE: PRT
<213> ORGANISM: Homo sapiens

<400> SEQUENCE: 79

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Lys Lys Tyr
            20                  25                  30
Leu Asn Trp Tyr His Gln Lys Pro Gly Lys Val Pro Glu Leu Leu Met
        35                  40                  45
His Asp Ala Ser Asn Leu Glu Thr Gly Val Pro Ser Arg Phe Ser Gly
    50                  55                  60
Arg Gly Ser Gly Thr Asp Phe Thr Leu Thr Ile Ser Ser Leu Gln Pro
65                  70                  75                  80
Glu Asp Ile Gly Thr Tyr Tyr Cys Gln Gln Tyr Asp Asn Leu Pro Pro
                85                  90                  95
Leu Thr Phe Gly Gly Gly Thr Lys Val Glu Ile Lys Arg Thr Val
            100                 105                 110

<210> SEQ ID NO 80
<211> LENGTH: 8
<212> TYPE: PRT
<213> ORGANISM: Homo sapiens

<400> SEQUENCE: 80

Gly Phe Thr Phe Ser Ser Tyr Asn
1               5

<210> SEQ ID NO 81
<211> LENGTH: 8
<212> TYPE: PRT
<213> ORGANISM: Homo sapiens

<400> SEQUENCE: 81

Ile Ser Ala Gly Ser Ser Tyr Ile
1               5

<210> SEQ ID NO 82
<211> LENGTH: 18
<212> TYPE: PRT
<213> ORGANISM: Homo sapiens

<400> SEQUENCE: 82
```

-continued

Ala Arg Glu Asp Tyr Gly Pro Gly Asn Tyr Tyr Ser Pro Asn Trp Phe
1               5                   10                  15

Asp Pro

<210> SEQ ID NO 83
<211> LENGTH: 9
<212> TYPE: PRT
<213> ORGANISM: Homo sapiens

<400> SEQUENCE: 83

Ser Ser Asn Ile Gly Ala Gly Tyr Asp
1               5

<210> SEQ ID NO 84
<211> LENGTH: 9
<212> TYPE: PRT
<213> ORGANISM: Homo sapiens

<400> SEQUENCE: 84

His Ser Tyr Asp Arg Ser Leu Ser Gly
1               5

<210> SEQ ID NO 85
<211> LENGTH: 125
<212> TYPE: PRT
<213> ORGANISM: Homo sapiens

<400> SEQUENCE: 85

Glu Val Gln Leu Val Glu Thr Gly Gly Gly Leu Ala Gln Pro Gly Gly
1               5                   10                  15

Ser Leu Arg Leu Ser Cys Ala Ala Ser Gly Phe Thr Phe Ser Ser Tyr
                20                  25                  30

Asn Met Asn Trp Val Arg Gln Ala Pro Gly Lys Gly Leu Glu Trp Val
            35                  40                  45

Ser His Ile Ser Ala Gly Ser Ser Tyr Ile Tyr Tyr Ser Asp Ser Val
        50                  55                  60

Lys Gly Arg Phe Thr Val Ser Arg Asp Asn Val Arg Asn Ser Val Tyr
65                  70                  75                  80

Leu Gln Met Asn Ser Leu Arg Ala Ala Asp Thr Ala Val Tyr Tyr Cys
                85                  90                  95

Ala Arg Glu Asp Tyr Gly Pro Gly Asn Tyr Tyr Ser Pro Asn Trp Phe
            100                 105                 110

Asp Pro Trp Gly Gln Gly Thr Leu Val Thr Val Ser Ser
        115                 120                 125

<210> SEQ ID NO 86
<211> LENGTH: 110
<212> TYPE: PRT
<213> ORGANISM: Homo sapiens

<400> SEQUENCE: 86

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Thr Asn Arg Pro Ser Gly Val Ser Asp Arg Phe
        50                  55                  60

```
Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys His Ser Tyr Asp Arg Ser
                 85                  90                  95

Leu Ser Gly Ser Val Phe Gly Gly Gly Thr Lys Leu Thr Val
            100                 105                 110
```

<210> SEQ ID NO 87
<211> LENGTH: 8
<212> TYPE: PRT
<213> ORGANISM: Homo sapiens

<400> SEQUENCE: 87

```
Gly Phe Asn Phe His Asn Tyr Gly
 1               5
```

<210> SEQ ID NO 88
<211> LENGTH: 8
<212> TYPE: PRT
<213> ORGANISM: Homo sapiens

<400> SEQUENCE: 88

```
Val Trp Tyr Asp Gly Ser Lys Lys
 1               5
```

<210> SEQ ID NO 89
<211> LENGTH: 13
<212> TYPE: PRT
<213> ORGANISM: Homo sapiens

<400> SEQUENCE: 89

```
Val Arg Asp Lys Val Gly Pro Thr Pro Tyr Phe Asp Ser
 1               5                  10
```

<210> SEQ ID NO 90
<211> LENGTH: 6
<212> TYPE: PRT
<213> ORGANISM: Homo sapiens

<400> SEQUENCE: 90

```
Asn Ile Gly Ser Glu Thr
 1               5
```

<210> SEQ ID NO 91
<211> LENGTH: 11
<212> TYPE: PRT
<213> ORGANISM: Homo sapiens

<400> SEQUENCE: 91

```
Gln Val Trp Asp Arg Ser Asn Tyr His Gln Val
 1               5                  10
```

<210> SEQ ID NO 92
<211> LENGTH: 120
<212> TYPE: PRT
<213> ORGANISM: Homo sapiens

<400> SEQUENCE: 92

```
Glu Val Gln Leu Val Glu Ser Gly Gly Asn Val Val Lys Pro Gly Thr
 1               5                  10                  15

Ser Leu Arg Leu Ser Cys Ala Ala Thr Gly Phe Asn Phe His Asn Tyr
             20                  25                  30

Gly Met Asn Trp Val Arg Gln Ala Pro Gly Lys Gly Leu Glu Trp Val
```

```
                    35                  40                  45
Ala Val Val Trp Tyr Asp Gly Ser Lys Lys Tyr Tyr Ala Asp Ser Val
 50                  55                  60

Thr Gly Arg Phe Ala Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                 85                  90                  95

Val Arg Asp Lys Val Gly Pro Thr Pro Tyr Phe Asp Ser Trp Gly Gln
            100                 105                 110

Gly Thr Leu Val Thr Val Ser Ser
            115                 120

<210> SEQ ID NO 93
<211> LENGTH: 107
<212> TYPE: PRT
<213> ORGANISM: Homo sapiens

<400> SEQUENCE: 93

Ser Tyr Val Leu Thr Gln Pro Pro Ser Val Ser Leu Ala Pro Gly Gly
  1               5                  10                  15

Thr Ala Ala Ile Thr Cys Gly Arg Asn Asn Ile Gly Ser Glu Thr Val
             20                  25                  30

His Trp Tyr Gln Gln Lys Pro Gly Gln Ala Pro Val Leu Val Val Tyr
             35                  40                  45

Asp Asp Asp Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Arg Ser Asn Tyr His
                 85                  90                  95

Gln Val Phe Gly Gly Gly Thr Lys Leu Thr Val
            100                 105
```

<210> SEQ ID NO 94
<211> LENGTH: 75
<212> TYPE: DNA
<213> ORGANISM: Homo sapiens

<400> SEQUENCE: 94
gaggtgcagc tggtggagtc tgggggaggc gtggtccagc ctggggaggtc cctgagactc    60 tcctgtgcgg cctct                                                      75

<210> SEQ ID NO 95
<211> LENGTH: 24
<212> TYPE: DNA
<213> ORGANISM: Homo sapiens

<400> SEQUENCE: 95
ggattcagct tcagtcacta tgcc                                            24

<210> SEQ ID NO 96
<211> LENGTH: 51
<212> TYPE: DNA
<213> ORGANISM: Homo sapiens

<400> SEQUENCE: 96
atgcactggg tccgccaggc tccaggcaag ggactggagt gggtggcagt t               51

```
<210> SEQ ID NO 97
<211> LENGTH: 24
<212> TYPE: DNA
<213> ORGANISM: Homo sapiens

<400> SEQUENCE: 97
atatcttatg atggagaaaa taca                                          24

<210> SEQ ID NO 98
<211> LENGTH: 114
<212> TYPE: DNA
<213> ORGANISM: Homo sapiens

<400> SEQUENCE: 98
tattacgcag actccgtgaa gggccgattc tccatctcca gagacaattc caagaacaca   60
gtgtctctgc aaatgaacag cctgagacct gaggacacgg ctctatatta ctgt        114

<210> SEQ ID NO 99
<211> LENGTH: 48
<212> TYPE: DNA
<213> ORGANISM: Homo sapiens

<400> SEQUENCE: 99
gcgagagacc gcatagtgga cgactactac tactacggta tggacgtc               48

<210> SEQ ID NO 100
<211> LENGTH: 34
<212> TYPE: DNA
<213> ORGANISM: Homo sapiens

<400> SEQUENCE: 100
tggggccaag gggccacggt caccgtctcc tcag                              34

<210> SEQ ID NO 101
<211> LENGTH: 369
<212> TYPE: DNA
<213> ORGANISM: Homo sapiens

<400> SEQUENCE: 101
gaggtgcagc tggtggagtc tgggggaggc gtggtccagc ctggaggtc cctgagactc   60 tcctgtgcgg cctctggatt cagcttcagt cactatgcca tgcactgggt ccgccaggct  120
ccaggcaagg gactggagtg ggtggcagtt atatcttatg atggagaaaa tacatattac  180
gcagactccg tgaagggccg attctccatc tccagagaca attccaagaa cacagtgtct  240
ctgcaaatga acagcctgag acctgaggac acggctctat attactgtgc gagagaccgc  300
atagtggacg actactacta ctacggtatg gacgtctggg gccaagggc cacggtcacc  360 gtctcctca                                                           369

<210> SEQ ID NO 102
<211> LENGTH: 78
<212> TYPE: DNA
<213> ORGANISM: Homo sapiens

<400> SEQUENCE: 102
gacatccaga tgacccagtc tccatcttcc ctgtctgcat ctgtaggaga cagagtcacc   60
atcacttgcc aggcgagt                                                 78

<210> SEQ ID NO 103
<211> LENGTH: 18
<212> TYPE: DNA
```

<213> ORGANISM: Homo sapiens

<400> SEQUENCE: 103
caggacatta agaagtat                                                       18

<210> SEQ ID NO 104
<211> LENGTH: 51
<212> TYPE: DNA
<213> ORGANISM: Homo sapiens

<400> SEQUENCE: 104
ttaaattggt atcatcagaa accagggaaa gtccctgagc tcctgatgca c                  51

<210> SEQ ID NO 105
<211> LENGTH: 108
<212> TYPE: DNA
<213> ORGANISM: Homo sapiens

<400> SEQUENCE: 105
aatttggaaa caggggtccc atcaaggttc agtggcaggg gatctgggac agattttact         60
ctcaccatta gcagcctgca gcctgaagat attggaacat attactgt                     108

<210> SEQ ID NO 106
<211> LENGTH: 30
<212> TYPE: DNA
<213> ORGANISM: Homo sapiens

<400> SEQUENCE: 106
caacagtatg ataatctgcc tccgctcact                                          30

<210> SEQ ID NO 107
<211> LENGTH: 31
<212> TYPE: DNA
<213> ORGANISM: Homo sapiens

<400> SEQUENCE: 107
ttcggcggag ggaccaaggt ggagatcaaa c                                        31

<210> SEQ ID NO 108
<211> LENGTH: 333
<212> TYPE: DNA
<213> ORGANISM: Homo sapiens

<400> SEQUENCE: 108
gacatccaga tgacccagtc tccatcttcc ctgtctgcat ctgtaggaga cagagtcacc         60
atcacttgcc aggcgagtca ggacattaag aagtatttaa attggtatca tcagaaacca       120
gggaaagtcc ctgagctcct gatgcacgat gcatccaatt tggaaacagg ggtcccatca       180
aggttcagtg gcaggggatc tgggacagat tttactctca ccattagcag cctgcagcct       240
gaagatattg aacatatta ctgtcaacag tatgataatc tgcctccgct cactttcggc       300
ggagggacca aggtggagat caaacgaact gtg                                    333

<210> SEQ ID NO 109
<211> LENGTH: 75
<212> TYPE: DNA
<213> ORGANISM: Homo sapiens

<400> SEQUENCE: 109
gaggtgcagc tggtggagac cggggggaggc ctggcccagc tgggggggtc cctgagactc        60
tcctgtgcag cctct                                                          75

<210> SEQ ID NO 110
<211> LENGTH: 24
<212> TYPE: DNA
<213> ORGANISM: Homo sapiens

<400> SEQUENCE: 110
ggattcacat tcagtagtta taac                                          24

<210> SEQ ID NO 111
<211> LENGTH: 51
<212> TYPE: DNA
<213> ORGANISM: Homo sapiens

<400> SEQUENCE: 111
atgaactggg tccgccaggc tccagggaag gggctggagt gggtctcaca c            51

<210> SEQ ID NO 112
<211> LENGTH: 24
<212> TYPE: DNA
<213> ORGANISM: Homo sapiens

<400> SEQUENCE: 112
attagtgcgg gtagtagtta cata                                          24

<210> SEQ ID NO 113
<211> LENGTH: 114
<212> TYPE: DNA
<213> ORGANISM: Homo sapiens

<400> SEQUENCE: 113
tactactcag actcagtgaa gggccgattc accgtctcca gagacaacgt caggaactca   60
gtatatctgc aaatgaacag cctgagagcc gctgacacgg ctgtgtatta ctgt        114

<210> SEQ ID NO 114
<211> LENGTH: 54
<212> TYPE: DNA
<213> ORGANISM: Homo sapiens

<400> SEQUENCE: 114
gcgagagagg attatggtcc gggaaattat tatagtccta actggttcga cccc         54

<210> SEQ ID NO 115
<211> LENGTH: 34
<212> TYPE: DNA
<213> ORGANISM: Homo sapiens

<400> SEQUENCE: 115
tggggccagg gaaccctggt caccgtctcc tcag                               34

<210> SEQ ID NO 116
<211> LENGTH: 375
<212> TYPE: DNA
<213> ORGANISM: Homo sapiens

<400> SEQUENCE: 116
gaggtgcagc tggtggagac cggggggaggc ctggcccagc ctgggggtc cctgagactc   60 tcctgtgcag cctctggatt cacattcagt agttataaca tgaactgggt ccgccaggct  120
ccagggaagg ggctggagtg gtctcacac attagtgcgg gtagtagtta catatactac   180
tcagactcag tgaagggccg attcaccgtc tccagagaca acgtcaggaa ctcagtatat  240

```
ctgcaaatga acagcctgag agccgctgac acggctgtgt attactgtgc gagagaggat      300
tatggtccgg gaaattatta tagtcctaac tggttcgacc cctggggcca gggaaccctg      360
gtcaccgtct cctca                                                       375

<210> SEQ ID NO 117
<211> LENGTH: 75
<212> TYPE: DNA
<213> ORGANISM: Homo sapiens

<400> SEQUENCE: 117
cagtctgtcg tgacgcagcc gccctcagtg tctggggccc cagggcagag agtcaccatc      60
tcctgcactg ggagc                                                       75

<210> SEQ ID NO 118
<211> LENGTH: 27
<212> TYPE: DNA
<213> ORGANISM: Homo sapiens

<400> SEQUENCE: 118
agctccaaca tcggggcagg ttatgat                                          27

<210> SEQ ID NO 119
<211> LENGTH: 51
<212> TYPE: DNA
<213> ORGANISM: Homo sapiens

<400> SEQUENCE: 119
gtacactggt accagcagct tccaggaaca gccccaaac tcctcatcta t                51

<210> SEQ ID NO 120
<211> LENGTH: 108
<212> TYPE: DNA
<213> ORGANISM: Homo sapiens

<400> SEQUENCE: 120
aatcggccct caggggtctc cgaccgattc tctggctcca agtctggcac ctcagcctcc      60
ctggccatca ctggactcca ggctgaggat gaggctgatt attactgc                   108

<210> SEQ ID NO 121
<211> LENGTH: 27
<212> TYPE: DNA
<213> ORGANISM: Homo sapiens

<400> SEQUENCE: 121
cactcctatg acagaagcct gagtggt                                          27

<210> SEQ ID NO 122
<211> LENGTH: 37
<212> TYPE: DNA
<213> ORGANISM: Homo sapiens

<400> SEQUENCE: 122
tcagtattcg gcggagggac caagctgacc gtcctag                               37

<210> SEQ ID NO 123
<211> LENGTH: 330
<212> TYPE: DNA
<213> ORGANISM: Homo sapiens

<400> SEQUENCE: 123
cagtctgtcg tgacgcagcc gccctcagtg tctggggccc cagggcagag agtcaccatc      60
```

```
tcctgcactg ggagcagctc aacatcggg gcaggttatg atgtacactg gtaccagcag      120
cttccaggaa cagcccccaa actcctcatc tatggcaaca ctaatcggcc ctcagggtc       180 tccgaccgat tctctggctc caagtctggc acctcagcct ccctggccat cactggactc      240
caggctgagg atgaggctga ttattactgc cactcctatg acagaagcct gagtggttca      300
gtattcggcg agggaccaa gctgaccgtc                                        330
```

<210> SEQ ID NO 124
<211> LENGTH: 75
<212> TYPE: DNA
<213> ORGANISM: Homo sapiens

<400> SEQUENCE: 124

```
caggtgcaac tggtggagtc tgggggaaat gtggtcaagc ctgggacgtc cctgagactg      60
tcctgtgcag cgact                                                        75
```

<210> SEQ ID NO 125
<211> LENGTH: 24
<212> TYPE: DNA
<213> ORGANISM: Homo sapiens

<400> SEQUENCE: 125

```
ggattcaact tccataacta cggc                                             24
```

<210> SEQ ID NO 126
<211> LENGTH: 51
<212> TYPE: DNA
<213> ORGANISM: Homo sapiens

<400> SEQUENCE: 126

```
atgaactggg tccgccaggc tccaggcaag gggctggagt gggtggcggt t               51
```

<210> SEQ ID NO 127
<211> LENGTH: 24
<212> TYPE: DNA
<213> ORGANISM: Homo sapiens

<400> SEQUENCE: 127

```
gtttggtatg atggaagtaa gaaa                                             24
```

<210> SEQ ID NO 128
<211> LENGTH: 114
<212> TYPE: DNA
<213> ORGANISM: Homo sapiens

<400> SEQUENCE: 128

```
tactatgcag actccgtgac gggccgattc gccatctcca gagacaattc caagaacact      60
ctgtatctgc aaatgaacag cctgagagtc gaggacacgg ctgtttatta ttgt           114
```

<210> SEQ ID NO 129
<211> LENGTH: 39
<212> TYPE: DNA
<213> ORGANISM: Homo sapiens

<400> SEQUENCE: 129

```
gtgagagata aagtgggacc gactccctac tttgactcc                             39
```

<210> SEQ ID NO 130
<211> LENGTH: 34
<212> TYPE: DNA

<213> ORGANISM: Homo sapiens

<400> SEQUENCE: 130
tggggccagg gaaccctggt caccgtatcc tcag   34

<210> SEQ ID NO 131
<211> LENGTH: 360
<212> TYPE: DNA
<213> ORGANISM: Homo sapiens

<400> SEQUENCE: 131
gaggtgcagc tggtggagtc tgggggaaat gtggtcaagc ctgggacgtc cctgagactg   60
tcctgtgcag cgactggatt caacttccat aactacggca tgaactgggt ccgccaggct   120
ccaggcaagg ggctggagtg ggtggcggtt gtttggtatg atggaagtaa gaaatactat   180
gcagactccg tgacgggccg attcgccatc tccagagaca attccaagaa cactctgtat   240
ctgcaaatga acagcctgag agtcgaggac acggctgttt attattgtgt gagagataaa   300
gtgggaccga ctccctactt tgactcctgg ggccagggaa ccctggtcac cgtctcgagt   360

<210> SEQ ID NO 132
<211> LENGTH: 75
<212> TYPE: DNA
<213> ORGANISM: Homo sapiens

<400> SEQUENCE: 132
tcctatgtgc tgactcagcc accctcggtg tcactggccc caggagggac ggccgcgatc   60
acctgtggaa gaaac   75

<210> SEQ ID NO 133
<211> LENGTH: 18
<212> TYPE: DNA
<213> ORGANISM: Homo sapiens

<400> SEQUENCE: 133
aacattggaa gtgaaact   18

<210> SEQ ID NO 134
<211> LENGTH: 51
<212> TYPE: DNA
<213> ORGANISM: Homo sapiens

<400> SEQUENCE: 134
gtgcactggt accagcagaa gccaggccag gcccctgtgc tggtcgtcta t   51

<210> SEQ ID NO 135
<211> LENGTH: 108
<212> TYPE: DNA
<213> ORGANISM: Homo sapiens

<400> SEQUENCE: 135
gaccggccct cagggatccc tgagcgattc tctggctcca actctgggaa cacggccacc   60
ctgaccatca gcagggtcga ggccggggat gaggccgact attactgt   108

<210> SEQ ID NO 136
<211> LENGTH: 33
<212> TYPE: DNA
<213> ORGANISM: Homo sapiens

<400> SEQUENCE: 136
caggtgtggg ataggagtaa ttatcatcag gta   33

<210> SEQ ID NO 137
<211> LENGTH: 31
<212> TYPE: DNA
<213> ORGANISM: Homo sapiens

<400> SEQUENCE: 137
ttcggcggag ggaccaagtt gaccgtccta g                                   31

<210> SEQ ID NO 138
<211> LENGTH: 321
<212> TYPE: DNA
<213> ORGANISM: Homo sapiens

<400> SEQUENCE: 138
tcctatgtgc tgactcagcc cccctcggtg tcactggccc caggagggac ggccgcgatc    60
acctgtggaa gaaacaacat tggaagtgaa actgtgcact ggtaccagca gaagccaggc   120
caggcccctg tgctggtcgt ctatgatgat gacgaccggc cctcaggat ccctgagcga    180 ttctctggct ccaactctgg gaacacggcc accctgacca tcagcagggt cgaggccggg   240
gatgaggccg actattactg tcaggtgtgg gataggagta attatcatca ggtattcggc   300
ggagggacca agctgaccgt c                                             321

<210> SEQ ID NO 139
<211> LENGTH: 378
<212> TYPE: DNA
<213> ORGANISM: Homo sapiens

<400> SEQUENCE: 139
caggtgcagc tggtacagtc tggggctgaa gtgaagaagc ctgggtcctc ggtgatggtc    60
tcctgccagg cctctggagg ccccctcaga aactatatta tcaactggct acgacaggcc   120
cctggacaag gccctgagtg gatgggaggg atcattcctg tcttgggtac agtcacactac  180 gcaccgaagt tccagggcag agtcacgatt accgcggacg aatccacgga cacagcctac   240
atccatctga tcagcctgag atctgaggac acggccatgt attactgtgc gacggaaaca   300
gctctggttg tatctactac ctacctacca cactactttg acaactgggg ccagggaacc   360
ctggtcaccg tctcctca                                                 378

<210> SEQ ID NO 140
<211> LENGTH: 378
<212> TYPE: DNA
<213> ORGANISM: Artificial
<220> FEATURE:
<223> OTHER INFORMATION: RSV#D25 VH codon optimized

<400> SEQUENCE: 140
caggtgcagc tggtgcagag cggagccgag gtgaagaaac ccggcagcag cgtgatggtg    60
tcctgccagg ccagcggcgg acccctgcgg aactacatca tcaactggct gcggcaggcc   120
ccaggccagg gccctgagtg gatgggcggc atcatccccg tgctgggcac cgtgcactac   180
gcccccaagt tccagggccg ggtgaccatc accgccgacg agagcaccga caccgcctac   240
atccacctga tcagcctgcg gagcgaggac accgccatgt actactgcgc caccgagacc   300
gccctggtgg tgtccaccac ctacctgccc cactacttcg acaactgggg ccagggcacc   360
ctggtgacag tctcgagt                                                 378

<210> SEQ ID NO 141

```
<211> LENGTH: 326
<212> TYPE: DNA
<213> ORGANISM: Homo sapiens

<400> SEQUENCE: 141
gacatccaga tgacccagtc tccatcctcc ctgtctgcag ctgtaggaga cagagtcacc    60
atcacttgcc aggcgagtca ggacattgtc aactatttaa attggtatca acagaaacca   120
gggaaagccc ctaagctcct gatctacgtt gcatccaatt tggagacagg ggtcccatca   180
aggttcagtg aagtggatc tgggacagat tttagtctca ccatcagcag cctgcagcct   240
gaagatgttg caacatatta ttgtcaacaa tatgataatc tcccactcac attcggcgga   300
gggaccaagg ttgagatcaa agaaac                                        326

<210> SEQ ID NO 142
<211> LENGTH: 326
<212> TYPE: DNA
<213> ORGANISM: Artificial
<220> FEATURE:
<223> OTHER INFORMATION: RSV#D25 VL codon optimized

<400> SEQUENCE: 142
gacatccaga tgacccagag ccccagcagc ctgtctgccg ccgtgggcga ccgggtgacc    60
atcacctgcc aggccagcca ggacatcgtg aactacctga actggtatca gcagaagccc   120
ggcaaggccc ccaagctgct gatctacgtg gccagcaacc tggaaaccgg cgtgcccagc   180
cggtttagcg gcagcggctc cggcaccgac ttcagcctga ccatcagcag cctgcagccc   240
gaggacgtgg ccacctacta ctgccagcag tacgacaacc tgcccctgac ctttggcggc   300
ggaacaaagg tggagatcaa gcggac                                        326

<210> SEQ ID NO 143
<211> LENGTH: 369
<212> TYPE: DNA
<213> ORGANISM: Homo sapiens
<220> FEATURE:
<221> NAME/KEY: CDS
<222> LOCATION: (1)..(369)

<400> SEQUENCE: 143 gag gtg cag ctg gtg gag tct ggg gga ggc gtg gtc cag cct ggg agg     48
Glu Val Gln Leu Val Glu Ser Gly Gly Gly Val Val Gln Pro Gly Arg
1               5                   10                  15 tcc ctg aga ctc tcc tgt gcg gcc tct gga ttc agc ttc agt cac tat     96
Ser Leu Arg Leu Ser Cys Ala Ala Ser Gly Phe Ser Phe Ser His Tyr
                20                  25                  30 gcc atg cac tgg gtc cgc cag gct cca ggc aag gga ctg gag tgg gtg    144
Ala Met His Trp Val Arg Gln Ala Pro Gly Lys Gly Leu Glu Trp Val
            35                  40                  45 gca gtt ata tct tat gat gga gaa aat aca tat tac gca gac tcc gtg    192
Ala Val Ile Ser Tyr Asp Gly Glu Asn Thr Tyr Tyr Ala Asp Ser Val
        50                  55                  60 aag ggc cga ttc tcc atc tcc aga gac aat tcc aag aac aca gtg tct    240
Lys Gly Arg Phe Ser Ile Ser Arg Asp Asn Ser Lys Asn Thr Val Ser
65                  70                  75                  80 ctg caa atg aac agc ctg aga cct gag gac acg gct cta tat tac tgt    288
Leu Gln Met Asn Ser Leu Arg Pro Glu Asp Thr Ala Leu Tyr Tyr Cys
                85                  90                  95 gcg aga gac cgc ata gtg gac gac tac tac tac tac ggt atg gac gtc    336
Ala Arg Asp Arg Ile Val Asp Asp Tyr Tyr Tyr Tyr Gly Met Asp Val
                100                 105                 110
```

```
tgg ggc caa ggg gcc acg gtc acc gtc tcc tca                    369
Trp Gly Gln Gly Ala Thr Val Thr Val Ser Ser
        115                 120

<210> SEQ ID NO 144
<211> LENGTH: 123
<212> TYPE: PRT
<213> ORGANISM: Homo sapiens

<400> SEQUENCE: 144

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser His Tyr
            20                  25                  30

Ala Met His Trp Val Arg Gln Ala Pro Gly Lys Gly Leu Glu Trp Val
        35                  40                  45

Ala Val Ile Ser Tyr Asp Gly Glu Asn Thr Tyr Tyr Ala Asp Ser Val
    50                  55                  60

Lys Gly Arg Phe Ser Ile Ser Arg Asp Asn Ser Lys Asn Thr Val Ser
65                  70                  75                  80

Leu Gln Met Asn Ser Leu Arg Pro Glu Asp Thr Ala Leu Tyr Tyr Cys
                85                  90                  95

Ala Arg Asp Arg Ile Val Asp Asp Tyr Tyr Tyr Tyr Gly Met Asp Val
            100                 105                 110

Trp Gly Gln Gly Ala Thr Val Thr Val Ser Ser
        115                 120

<210> SEQ ID NO 145
<211> LENGTH: 333
<212> TYPE: DNA
<213> ORGANISM: Homo sapiens
<220> FEATURE:
<221> NAME/KEY: CDS
<222> LOCATION: (1)..(333)

<400> SEQUENCE: 145 gac atc cag atg acc cag tct cca tct tcc ctg tct gca tct gta gga    48
Asp Ile Gln Met Thr Gln Ser Pro Ser Ser Leu Ser Ala Ser Val Gly
1               5                   10                  15 gac aga gtc acc atc act tgc cag gcg agt cag gac att aag aag tat    96
Asp Arg Val Thr Ile Thr Cys Gln Ala Ser Gln Asp Ile Lys Lys Tyr
            20                  25                  30 tta aat tgg tat cat cag aaa cca ggg aaa gtc cct gag ctc ctg atg   144
Leu Asn Trp Tyr His Gln Lys Pro Gly Lys Val Pro Glu Leu Leu Met
        35                  40                  45 cac gat gca tcc aat ttg gaa aca ggg gtc cca tca agg ttc agt ggc   192
His Asp Ala Ser Asn Leu Glu Thr Gly Val Pro Ser Arg Phe Ser Gly
    50                  55                  60 agg gga tct ggg aca gat ttt act ctc acc att agc agc ctg cag cct   240
Arg Gly Ser Gly Thr Asp Phe Thr Leu Thr Ile Ser Ser Leu Gln Pro
65                  70                  75                  80 gaa gat att gga aca tat tac tgt caa cag tat gat aat ctg cct ccg   288
Glu Asp Ile Gly Thr Tyr Tyr Cys Gln Gln Tyr Asp Asn Leu Pro Pro
                85                  90                  95 ctc act ttc ggc gga ggg acc aag gtg gag atc aaa cga act gtg       333
Leu Thr Phe Gly Gly Gly Thr Lys Val Glu Ile Lys Arg Thr Val
            100                 105                 110

<210> SEQ ID NO 146
<211> LENGTH: 111
<212> TYPE: PRT
```

<213> ORGANISM: Homo sapiens

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Lys Lys Tyr
            20                  25                  30

Leu Asn Trp Tyr His Gln Lys Pro Gly Lys Val Pro Glu Leu Leu Met
        35                  40                  45

His Asp Ala Ser Asn Leu Glu Thr Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Ile Gly Thr Tyr Tyr Cys Gln Gln Tyr Asp Asn Leu Pro Pro
                85                  90                  95

Leu Thr Phe Gly Gly Gly Thr Lys Val Glu Ile Lys Arg Thr Val
            100                 105                 110

<210> SEQ ID NO 147
<211> LENGTH: 98
<212> TYPE: PRT
<213> ORGANISM: Artificial
<220> FEATURE:
<223> OTHER INFORMATION: IGHV#-30 germl.

<400> SEQUENCE: 147

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 148
<211> LENGTH: 98
<212> TYPE: PRT
<213> ORGANISM: Artificial
<220> FEATURE:
<223> OTHER INFORMATION: IGKV1-33 germl.

<400> SEQUENCE: 148

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

```
Glu Asp Ile Ala Thr Tyr Tyr Cys Gln Gln Tyr Asp Asn Leu Pro Pro
                85                  90                  95

Leu Thr

<210> SEQ ID NO 149
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 149 gag gtg cag ctg gtg gag acc ggg gga ggc ctg gcc cag cct ggg ggg        48
Glu Val Gln Leu Val Glu Thr Gly Gly Gly Leu Ala Gln Pro Gly Gly
1               5                   10                  15 tcc ctg aga ctc tcc tgt gca gcc tct gga ttc aca ttc agt agt tat        96
Ser Leu Arg Leu Ser Cys Ala Ala Ser Gly Phe Thr Phe Ser Ser Tyr
            20                  25                  30 aac atg aac tgg gtc cgc cag gct cca ggg aag ggg ctg gag tgg gtc       144
Asn Met Asn Trp Val Arg Gln Ala Pro Gly Lys Gly Leu Glu Trp Val
        35                  40                  45 tca cac att agt gcg ggt agt agt tac ata tac tac tca gac tca gtg       192
Ser His Ile Ser Ala Gly Ser Ser Tyr Ile Tyr Tyr Ser Asp Ser Val
    50                  55                  60 aag ggc cga ttc acc gtc tcc aga gac aac gtc agg aac tca gta tat       240
Lys Gly Arg Phe Thr Val Ser Arg Asp Asn Val Arg Asn Ser Val Tyr
65                  70                  75                  80 ctg caa atg aac agc ctg aga gcc gct gac acg gct gtg tat tac tgt       288
Leu Gln Met Asn Ser Leu Arg Ala Ala Asp Thr Ala Val Tyr Tyr Cys
                85                  90                  95 gcg aga gag gat tat ggt ccg gga aat tat tat agt cct aac tgg ttc       336
Ala Arg Glu Asp Tyr Gly Pro Gly Asn Tyr Tyr Ser Pro Asn Trp Phe
            100                 105                 110 gac ccc tgg ggc cag gga acc ctg gtc acc gtc tcc tca                   375
Asp Pro Trp Gly Gln Gly Thr Leu Val Thr Val Ser Ser
        115                 120                 125

<210> SEQ ID NO 150
<211> LENGTH: 125
<212> TYPE: PRT
<213> ORGANISM: Homo sapiens

<400> SEQUENCE: 150

Glu Val Gln Leu Val Glu Thr Gly Gly Gly Leu Ala Gln Pro Gly Gly
1               5                   10                  15

Ser Leu Arg Leu Ser Cys Ala Ala Ser Gly Phe Thr Phe Ser Ser Tyr
            20                  25                  30

Asn Met Asn Trp Val Arg Gln Ala Pro Gly Lys Gly Leu Glu Trp Val
        35                  40                  45

Ser His Ile Ser Ala Gly Ser Ser Tyr Ile Tyr Tyr Ser Asp Ser Val
    50                  55                  60

Lys Gly Arg Phe Thr Val Ser Arg Asp Asn Val Arg Asn Ser Val Tyr
65                  70                  75                  80

Leu Gln Met Asn Ser Leu Arg Ala Ala Asp Thr Ala Val Tyr Tyr Cys
                85                  90                  95

Ala Arg Glu Asp Tyr Gly Pro Gly Asn Tyr Tyr Ser Pro Asn Trp Phe
            100                 105                 110

Asp Pro Trp Gly Gln Gly Thr Leu Val Thr Val Ser Ser
```

<210> SEQ ID NO 151
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 151

```
cag tct gtc gtg acg cag ccg ccc tca gtg tct ggg gcc cca ggg cag        48
Gln Ser Val Val Thr Gln Pro Pro Ser Val Ser Gly Ala Pro Gly Gln
1               5                   10                  15 aga gtc acc atc tcc tgc act ggg agc agc tcc aac atc ggg gca ggt        96
Arg Val Thr Ile Ser Cys Thr Gly Ser Ser Ser Asn Ile Gly Ala Gly
                20                  25                  30 tat gat gta cac tgg tac cag cag ctt cca gga aca gcc ccc aaa ctc       144
Tyr Asp Val His Trp Tyr Gln Gln Leu Pro Gly Thr Ala Pro Lys Leu
            35                  40                  45 ctc atc tat ggc aac act aat cgg ccc tca ggg gtc tcc gac cga ttc       192
Leu Ile Tyr Gly Asn Thr Asn Arg Pro Ser Gly Val Ser Asp Arg Phe
        50                  55                  60 tct ggc tcc aag tct ggc acc tca gcc tcc ctg gcc atc act gga ctc       240
Ser Gly Ser Lys Ser Gly Thr Ser Ala Ser Leu Ala Ile Thr Gly Leu
65                  70                  75                  80 cag gct gag gat gag gct gat tat tac tgc cac tcc tat gac aga agc       288
Gln Ala Glu Asp Glu Ala Asp Tyr Tyr Cys His Ser Tyr Asp Arg Ser
                85                  90                  95 ctg agt ggt tca gta ttc ggc gga ggg acc aag ctg acc gtc               330
Leu Ser Gly Ser Val Phe Gly Gly Gly Thr Lys Leu Thr Val
            100                 105                 110
```

<210> SEQ ID NO 152
<211> LENGTH: 110
<212> TYPE: PRT
<213> ORGANISM: Homo sapiens

<400> SEQUENCE: 152

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Thr Asn Arg Pro Ser Gly Val Ser Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys His Ser Tyr Asp Arg Ser
                85                  90                  95

Leu Ser Gly Ser Val Phe Gly Gly Gly Thr Lys Leu Thr Val
            100                 105                 110

<210> SEQ ID NO 153
<211> LENGTH: 73
<212> TYPE: PRT
<213> ORGANISM: Artificial
<220> FEATURE:
<223> OTHER INFORMATION: IGHV3-21 germl.

<400> SEQUENCE: 153

```
Gly Phe Thr Phe Ser Ser Tyr Ser Met Asn Trp Val Arg Gln Ala Pro
1               5                   10                  15

Gly Lys Gly Leu Glu Trp Val Ser Ser Ile Ser Ser Ser Ser Ser Tyr
            20                  25                  30

Ile Tyr Tyr Ala Asp Ser Val Lys Gly Arg Phe Thr Ile Ser Arg Asp
        35                  40                  45

Asn Ala Lys Asn Ser Leu Tyr Leu Gln Met Asn Ser Leu Arg Ala Glu
    50                  55                  60

Asp Thr Ala Val Tyr Tyr Cys Ala Arg
65                  70
```

<210> SEQ ID NO 154
<211> LENGTH: 99
<212> TYPE: PRT
<213> ORGANISM: Artificial
<220> FEATURE:
<223> OTHER INFORMATION: IGLV1-40 germl.

<400> SEQUENCE: 154

```
Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly
```

<210> SEQ ID NO 155
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 155

```
gag gtg cag ctg gtg gag tct ggg gga aat gtg gtc aag cct ggg acg     48
Glu Val Gln Leu Val Glu Ser Gly Gly Asn Val Val Lys Pro Gly Thr
1               5                   10                  15 tcc ctg aga ctg tcc tgt gca gcg act gga ttc aac ttc cat aac tac     96
Ser Leu Arg Leu Ser Cys Ala Ala Thr Gly Phe Asn Phe His Asn Tyr
            20                  25                  30 ggc atg aac tgg gtc cgc cag gct cca ggc aag ggg ctg gag tgg gtg    144
Gly Met Asn Trp Val Arg Gln Ala Pro Gly Lys Gly Leu Glu Trp Val
        35                  40                  45 gcg gtt gtt tgg tat gat gga agt aag aaa tac tat gca gac tcc gtg    192
Ala Val Val Trp Tyr Asp Gly Ser Lys Lys Tyr Tyr Ala Asp Ser Val
    50                  55                  60 acg ggc cga ttc gcc atc tcc aga gac aat tcc aag aac act ctg tat    240
Thr Gly Arg Phe Ala Ile Ser Arg Asp Asn Ser Lys Asn Thr Leu Tyr
65                  70                  75                  80 ctg caa atg aac agc ctg aga gtc gag gac acg gct gtt tat tat tgt    288
Leu Gln Met Asn Ser Leu Arg Val Glu Asp Thr Ala Val Tyr Tyr Cys
```

```
                    85                  90                  95
gtg aga gat aaa gtg gga ccg act ccc tac ttt gac tcc tgg ggc cag        336
Val Arg Asp Lys Val Gly Pro Thr Pro Tyr Phe Asp Ser Trp Gly Gln
            100                 105                 110 gga acc ctg gtc acc gtc tcg agt                                        360
Gly Thr Leu Val Thr Val Ser Ser
            115                 120

<210> SEQ ID NO 156
<211> LENGTH: 120
<212> TYPE: PRT
<213> ORGANISM: Homo sapiens

<400> SEQUENCE: 156

Glu Val Gln Leu Val Glu Ser Gly Gly Asn Val Val Lys Pro Gly Thr
1               5                   10                  15

Ser Leu Arg Leu Ser Cys Ala Ala Thr Gly Phe Asn Phe His Asn Tyr
            20                  25                  30

Gly Met Asn Trp Val Arg Gln Ala Pro Gly Lys Gly Leu Glu Trp Val
        35                  40                  45

Ala Val Val Trp Tyr Asp Gly Ser Lys Lys Tyr Tyr Ala Asp Ser Val
    50                  55                  60

Thr Gly Arg Phe Ala Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Arg Asp Lys Val Gly Pro Thr Pro Tyr Phe Asp Ser Trp Gly Gln
            100                 105                 110

Gly Thr Leu Val Thr Val Ser Ser
            115                 120

<210> SEQ ID NO 157
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 157 tcc tat gtg ctg act cag ccc ccc tcg gtg tca ctg gcc cca gga ggg        48
Ser Tyr Val Leu Thr Gln Pro Pro Ser Val Ser Leu Ala Pro Gly Gly
1               5                   10                  15 acg gcc gcg atc acc tgt gga aga aac aac att gga agt gaa act gtg        96
Thr Ala Ala Ile Thr Cys Gly Arg Asn Asn Ile Gly Ser Glu Thr Val
            20                  25                  30 cac tgg tac cag cag aag cca ggc cag gcc cct gtg ctg gtc gtc tat        144
His Trp Tyr Gln Gln Lys Pro Gly Gln Ala Pro Val Leu Val Val Tyr
        35                  40                  45 gat gat gac gac cgg ccc tca ggg atc cct gag cga ttc tct ggc tcc        192
Asp Asp Asp Asp Arg Pro Ser Gly Ile Pro Glu Arg Phe Ser Gly Ser
    50                  55                  60 aac tct ggg aac acg gcc acc ctg acc atc agc agg gtc gag gcc ggg        240
Asn Ser Gly Asn Thr Ala Thr Leu Thr Ile Ser Arg Val Glu Ala Gly
65                  70                  75                  80 gat gag gcc gac tat tac tgt cag gtg tgg gat agg agt aat tat cat        288
Asp Glu Ala Asp Tyr Tyr Cys Gln Val Trp Asp Arg Ser Asn Tyr His
                85                  90                  95 cag gta ttc ggc gga ggg acc aag ctg acc gtc                            321
Gln Val Phe Gly Gly Gly Thr Lys Leu Thr Val
```

<210> SEQ ID NO 158
<211> LENGTH: 107
<212> TYPE: PRT
<213> ORGANISM: Homo sapiens

<400> SEQUENCE: 158

Ser Tyr Val Leu Thr Gln Pro Pro Ser Val Ser Leu Ala Pro Gly Gly
1               5                   10                  15

Thr Ala Ala Ile Thr Cys Gly Arg Asn Asn Ile Gly Ser Glu Thr Val
            20                  25                  30

His Trp Tyr Gln Gln Lys Pro Gly Gln Ala Pro Val Leu Val Val Tyr
        35                  40                  45

Asp Asp Asp Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Arg Ser Asn Tyr His
                85                  90                  95

Gln Val Phe Gly Gly Gly Thr Lys Leu Thr Val
            100                 105

<210> SEQ ID NO 159
<211> LENGTH: 98
<212> TYPE: PRT
<213> ORGANISM: Artificial
<220> FEATURE:
<223> OTHER INFORMATION: IGHV3-33 germl.

<400> SEQUENCE: 159

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 160
<211> LENGTH: 98
<212> TYPE: PRT
<213> ORGANISM: Artificial
<220> FEATURE:
<223> OTHER INFORMATION: IGLV3-21 germl.

<400> SEQUENCE: 160

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

```
Asp Asp Ser Asp Arg Pro Ser Gly Ile Pro Glu Arg Phe Ser Gly Ser
        50              55              60

Asn Ser Gly Asn Thr Ala Thr Leu Thr Ile Ser Arg Val Glu Ala Gly
 65              70              75              80

Asp Glu Ala Asp Tyr Tyr Cys Gln Val Trp Asp Ser Ser Asp His
                85              90              95

Gln Val
```